US009212197B2

(12) United States Patent
Kottas et al.

(10) Patent No.: US 9,212,197 B2
(45) Date of Patent: Dec. 15, 2015

(54) PHOSPHORESCENT HETEROLEPTIC PHENYLBENZIMIDAZOLE DOPANTS

(75) Inventors: Gregg Kottas, Ewing, NJ (US); Chuanjun Xia, Lawrenceville, NJ (US); Zeinab Elshenawy, Holland, PA (US); Nasrin Ansari, Monmouth Junction, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 826 days.

(21) Appl. No.: 13/111,490

(22) Filed: May 19, 2011

(65) Prior Publication Data
US 2012/0292600 A1   Nov. 22, 2012

(51) Int. Cl.
*H01L 51/54* (2006.01)
*C09K 11/06* (2006.01)
*C07F 15/00* (2006.01)
*H01L 51/00* (2006.01)
*H01L 51/50* (2006.01)

(52) U.S. Cl.
CPC .............. *C07F 15/0033* (2013.01); *C09K 11/06* (2013.01); *H01L 51/0085* (2013.01); *C09K 2211/1029* (2013.01); *C09K 2211/1044* (2013.01); *C09K 2211/185* (2013.01); *H01L 51/5016* (2013.01)

(58) Field of Classification Search
CPC . C07F 15/0033; H01L 51/0085; H01L 51/50; H01L 51/5016; C09K 11/06; C09K 2211/1029; C09K 2211/1044; C09K 2211/185
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,893,743 B2 * | 5/2005 | Sato et al. ..................... | 428/690 |
| 6,902,830 B2 | 6/2005 | Thompson et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 8,367,223 B2 * | 2/2013 | Xia et al. ....................... | 428/690 |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

English language machine translation of JP 2009/059997 A, 2009.*
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," *Adv. Mater.*, 6(9):677-679 (1994).
Paulose, Betty Marie Jennifer S. et al., "First Examples of Alkenyl Pyridines as Organic Ligands for Phosphorescent Iridium Complexes," *Adv. Mater.*, 16(22):2003-2007 (2004).

(Continued)

*Primary Examiner* — Michael H Wilson
(74) *Attorney, Agent, or Firm* — Duane Morris LLP

(57) ABSTRACT

Novel phosphorescent heteroleptic iridium complexes with benzimidazole and phenylpyridine ligands are provided. These iridium complexes can improve OLED properties, and are useful in white light applications.

27 Claims, 3 Drawing Sheets

(56) References Cited

U.S. PATENT DOCUMENTS

| | | |
|---|---|---|
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0134789 A1* | 5/2009 | Ise ............................. 313/504 |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2010/0141127 A1 | 6/2010 | Xia et al. |
| 2010/0244004 A1 | 9/2010 | Xia et al. |

FOREIGN PATENT DOCUMENTS

| | | | |
|---|---|---|---|
| EP | 2034538 | 3/2009 | |
| JP | 200511610 | 1/2005 | |
| JP | 2007123392 | 5/2007 | |
| JP | 2007254297 | 10/2007 | |
| JP | 2009/059997 A * | 3/2009 | ............. H01L 51/50 |
| JP | 2008074939 | 10/2009 | |
| WO | WO 0139234 | 5/2001 | |
| WO | WO 0202714 | 1/2002 | |
| WO | WO 0215645 | 2/2002 | |
| WO | WO 03040257 | 5/2003 | |
| WO | WO 03060956 | 7/2003 | |
| WO | WO 2004093207 | 10/2004 | |
| WO | WO 2004107822 | 12/2004 | |
| WO | WO 2005014551 | 2/2005 | |
| WO | WO 2005019373 | 3/2005 | |
| WO | WO 2005030900 | 4/2005 | |
| WO | WO 2005089025 | 9/2005 | |
| WO | WO 2005123873 | 12/2005 | |
| WO | WO 2006009024 | 1/2006 | |
| WO | WO 2006056418 | 6/2006 | |
| WO | WO 2006072002 | 7/2006 | |
| WO | WO 2006082742 | 8/2006 | |
| WO | WO 2006098120 | 9/2006 | |
| WO | WO 2006100298 | 9/2006 | |
| WO | WO 2006103874 | 10/2006 | |
| WO | WO 2006114966 | 11/2006 | |
| WO | WO 2006132173 | 12/2006 | |
| WO | WO 2007002683 | 1/2007 | |
| WO | WO 2007004380 | 1/2007 | |
| WO | WO 2007063796 | 6/2007 | |
| WO | WO 2007063754 | 8/2007 | |
| WO | WO 2008101842 | 8/2008 | |
| WO | WO 2008132085 | 11/2008 | |
| WO | WO 2009000673 | 12/2008 | |
| WO | WO 2009003898 | 1/2009 | |
| WO | WO 2009008311 | 1/2009 | |
| WO | WO 2009018009 | 2/2009 | |
| WO | WO 2009050290 | 4/2009 | |
| WO | WO 2008056746 | 5/2009 | |
| WO | WO 2009021126 | 5/2009 | |
| WO | WO 2009062578 | 5/2009 | |
| WO | WO 2009063833 | 5/2009 | |
| WO | WO 2009066778 | 5/2009 | |
| WO | WO 2009066779 | 5/2009 | |
| WO | WO 2009086028 | 7/2009 | |
| WO | WO 2009100991 | 8/2009 | |

OTHER PUBLICATIONS

Tung, Yung-Liang et al., "Organic Light-Emitting Diodes Based on Charge-Neutral $Ru^{II}$ PHosphorescent Emitters," Adv. Mater., 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Wong, Wai-Yeung, "Multifunctional Iridium Complexes Based on Carbazole Modules as Highly Efficient Electrophosphors," Angew. Chem. Int Ed., 45:7800-7803 (2006).

Tang, C.W. and VanSlyke, S.A., "Organic Electroluminescent Diodes," Appl. Phys. Lett., 51(12):913-915 (1987).

Adachi, Chihaya et al., "Organic Electroluminescent Device Having a Hole Conductor as an Emitting Layer," Appl. Phys. Lett., 55(15):1489-1491 (1989).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Gao, Zhiqiang et al., "Bright-Blue Electroluminescence From a Silyl-Substituted ter-(phenylene-vinylene) derivative," Appl. Phys. Lett., 74(6):865-867 (1999).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Hung, L.S. et al., "Anode Modification in Organic Light-Emitting Diodes by Low-Frequency Plasma Polymerization of $CHF_3$," Appl. Phys. Lett., 78(5):673-675 (2001).

Ikai, Masamichi and Tokito, Shizuo, "Highly Efficient Phosphorescence From Organic Light-Emitting Devices with an Exciton-Block Layers" Appl. Phys. Lett., 79(2):156-158 (2001).

Wang, Y. et al., "Highly Efficient Electroluminescent Materials Based on Fluorinated Organometallic Iridium Compounds," Appl. Phys. Lett., 79(4):449-451 (2001).

Kwong, Raymond C. et al., "High Operational Stability of Electrophosphorescent Devices," Appl. Phys. Lett., 81(1):162-164 (2002).

Holmes, R.J. et al., "Blue Organic Electrophosphorescence Using Exothermic Host-Guest Energy Transfer," Appl. Phys. Lett., 82(15):2422-2424 (2003).

Sotoyama, Wataru et al., "Efficient Organic Light-Emitting Diodes with Phosphorescent Platinum Complexes Containing $N^AC^AN$-Coordinating Tridentate Ligand," Appl. Phys. Lett., 86:153505-1-153505-3 (2005).

Okumoto, Kenji et al., "Green Fluorescent Organic Light-Emitting Device with External Quantum Efficiency of Nearly 10%," Appl. Phys. Lett., 89:063504-1-063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Aonuma, Masaki et al., "Material Design of Hole Transport Materials Capable of Thick-Film Formation in Organic Light Emitting Diodes," Appl. Phys. Lett., 90:183503-1-183503-3 (2007).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

Adachi, Chihaya et al., "High-Efficiency Red Electrophosphorescence Devices," Appl. Phys. Lett., 78(11):1622-1624 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Hamada, Yuji et al., "High Luminance in Organic Electroluminescent Devices with Bis(10-hydroxybenzo[h]quinolinato)beryllium as an Emitter," Chem. Lett., 905-906 (1993).

(56) References Cited

OTHER PUBLICATIONS

Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).

Mi, Bao-Xiu et al., "Thermally Stable Hole-Transporting Material for Organic Light-Emitting Diode: an Isoindole Derivative," *Chem. Mater.*, 15(16):3148-3151 (2003).

Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).

Niu, Yu-Hua et al., "Highly Efficient Electrophosphorescent Devices with Saturated Red Emission from a Neutral Osmium Complex," *Chem. Mater.*, 17(13):3532-3536 (2005).

Lo, Shih-Chun et al., "Blue Phosphorescence from Iridium(III) Complexes at Room Temperature," *Chem. Mater.*, 18(21):5119-5129 (2006).

Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cyclometalated Iridium Complexes," *Inorg. Chem.*, 40(7):1704-1711 (2001).

Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).

Noda, Tetsuya and Shirota, Yasuhiko, "5,5'-Bis(dimesitylboryl)-2,2'-bithiophene and 5,5''-Bis(dimesitylboryl)-2,2':5',2''-terthiophene as a Novel Family of Electron-Transporting Amorphous Molecular Materials," *J. Am. Chem. Soc.*, 120 (37):9714-9715 (1998).

Sakamoto, Youichi et al., "Synthesis, Characterization, and Electron-Transport Property of Perfluorinated Phenylene Dendrimers," *J. Am. Chem. Soc.*, 122(8)1832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yasuhiko et al., "Starburst Molecules Based on π-Electron Systems as Materials for Organic Electroluminescent Devices," *Journal of Luminescence*, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al., 1,2,4-Triazole Derivative as an Electron Transport Layer in Organic Electroluminescent Devices, *Jpn. J. Appl. Phys.*, 32:L917-L920 (1993).

Van Slyke, S. A. et al., "Organic Electroluminescent Devices with Improved Stability," *Appl. Phys. Lett.*, 69(15):2160-2162 (1996).

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes of Poly(3-Hexylthiophene): Electro-Optical Characteristics Related to Structure," *Synthetic Metals*, 87:171-177 (1997).

Hu, Nan-Xing et al., "Novel High $T_9$ Hole-Transport Molecules Based on Indolo[3,2-b]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

Baldo et al., "Highly Efficient Phosphorescent Emission from Organic Electroluminescent Devices," *Nature*, vol. 395, 151-154, (1998).

Baldo et al., "Very high-efficiency green organic light-emitting devices based on electrophosphorescence," Appl. Phys. Lett., vol. 75, No. 3, 4-6 (1999).

\* cited by examiner

Formula I

PHOSPHORESCENT HETEROLEPTIC PHENYLBENZIMIDAZOLE DOPANTS

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds suitable for incorporation into OLED devices, specifically the compounds comprise heteroleptic iridium complexes.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

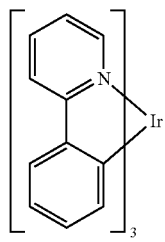

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A compound comprising a heteroleptic iridium complex having the formula:

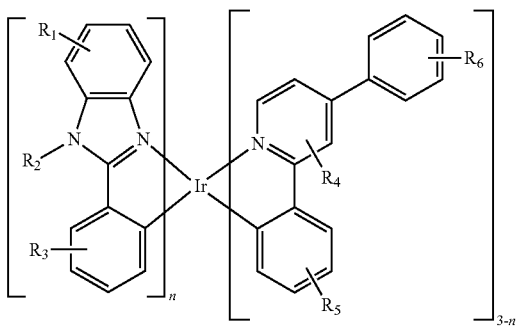

Formula I, is provided. $R_1$, $R_3$, $R_4$, $R_5$ and $R_6$ represent mono-, di-, tri- or tetra-substitution. $R_1$, $R_2$, $R_3$, $R_4$, $R_5$ and $R_6$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Additionally, $R_1$, $R_3$, $R_4$, $R_5$ and $R_6$ are optionally fused and may be further substituted, and n is 1 or 2.

In one aspect, n is 2. In another aspect, n is 1.

In one aspect, $R_2$ is aryl or substituted aryl. In another aspect, $R_2$ is a 2,6-disubstituted aryl. In one aspect, $R_2$ is alkyl. In another aspect, $R_2$ is

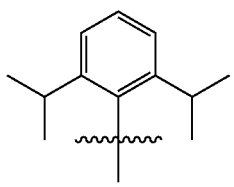

In one aspect, $R_3$, $R_4$, $R_5$ and $R_6$ are each independently selected from the group consisting of hydrogen and alkyl, and wherein at least one of $R_3$, $R_4$, $R_5$ and $R_6$ is alkyl. In one aspect, $R_5$ is aryl. In another aspect, $R_6$ is aryl.

In one aspect, $R_1$, $R_3$, and $R_5$ are hydrogen.

Specific non-limiting examples of a compound of Formula I are provided. In one aspect, the compound is selected from the group consisting of Compound 1-Compound 100.

A first device is also provided. The first device comprises a first organic light emitting device, further comprising an anode, a cathode, and an organic layer, disposed between the anode and the cathode, comprising a compound having the formula:

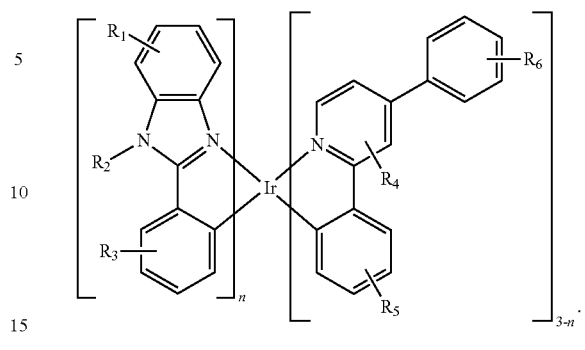

Formula I $R_1$, $R_3$, $R_4$, $R_5$ and $R_6$ represent mono-, di-, tri- or tetra-substitution. $R_1$, $R_2$, $R_3$, $R_4$, $R_5$ and $R_6$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Additionally, $R_1$, $R_3$, $R_4$, $R_5$ and $R_6$ are optionally fused and may be further substituted, and n is 1 or 2.

In one aspect, the organic layer is an emissive layer and the compound is an emissive dopant. In one aspect, the organic layer is an emissive layer and the compound is a non-emissive dopant. In another aspect, the organic layer further comprises a host.

In one aspect, the host comprises a triphenylene containing benzo-fused thiophene or benzo-fused furan, wherein any substituent in the compound is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CHC_nH_{2n+1}$, $Ar_1$, $Ar_1-Ar_2$, $C_nH_{2n}-Ar_1$, or no substitution. $Ar_1$ and $Ar_2$ are independently selected from the group consisting of benzene, biphenyl, naphthalene, triphenylene, carbazole, and heteroaromatic analogs thereof, and n is from 1 to 10.

In one embodiment, the host has the formula:

Compound B

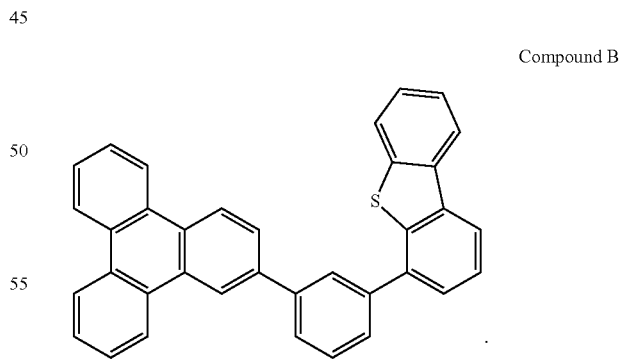

In one aspect, the host is a metal complex.

In one aspect, the first device is a consumer product. In another aspect, the first device is an organic light-emitting device. In one aspect, the first device further comprises a second emissive dopant having a peak wavelength of between 400 to 500 nanometers. In one aspect, the second emissive dopant is a fluorescent emitter. In another aspect, the second emissive dopant is a phosphorescent emitter.

In one aspect, the first device comprises a lighting panel. In one aspect, the first device further comprises a first organic light-emitting device comprising a compound of Formula I and a second light-emitting device separate from the first organic light-emitting device comprising an emissive dopant having a peak wavelength of between 400 to 500 nanometers. In another embodiment, the first device comprises an organic light-emitting device having a first emissive layer comprising a compound of Formula I and a second emissive layer comprising an emissive dopant having a peak wavelength of between 400 to 500 nanometers.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
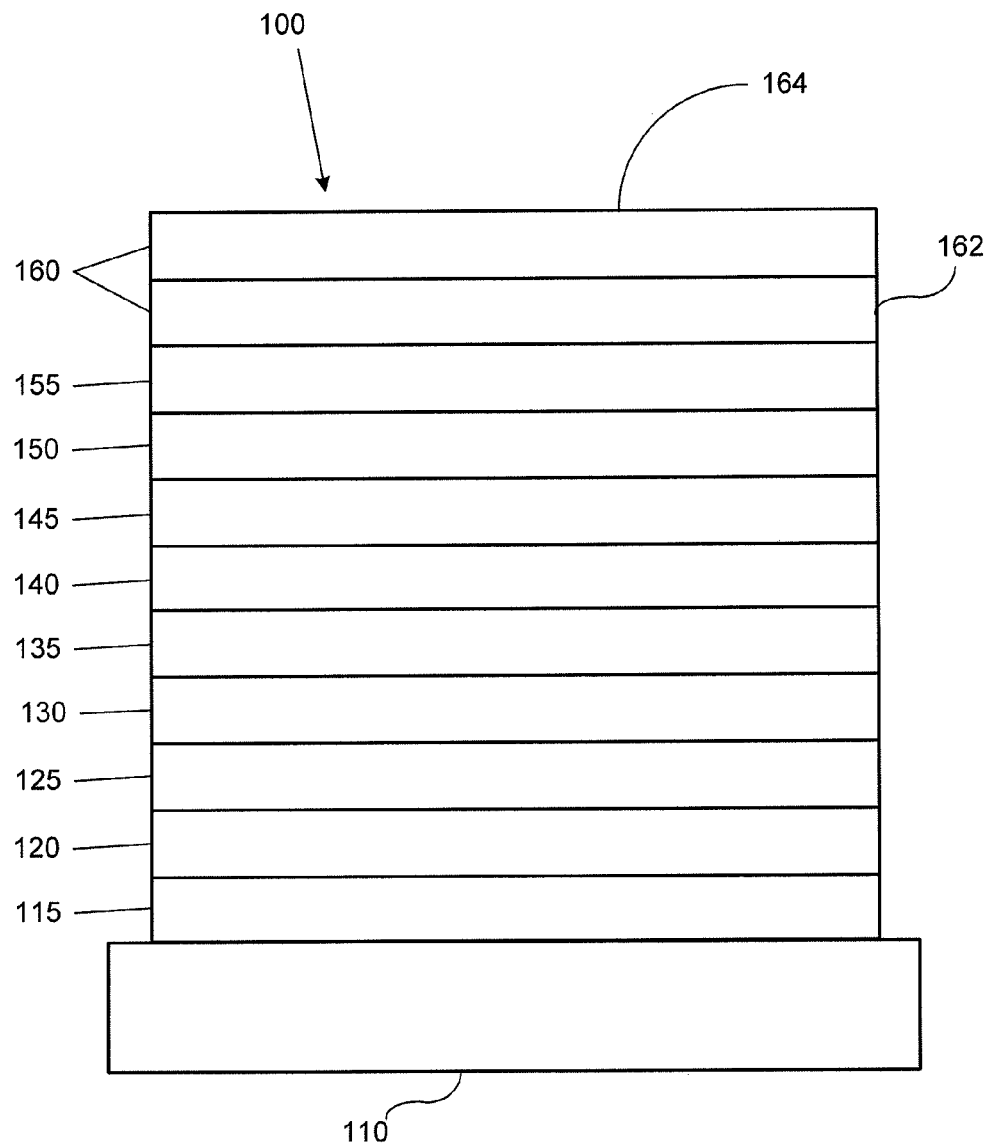
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
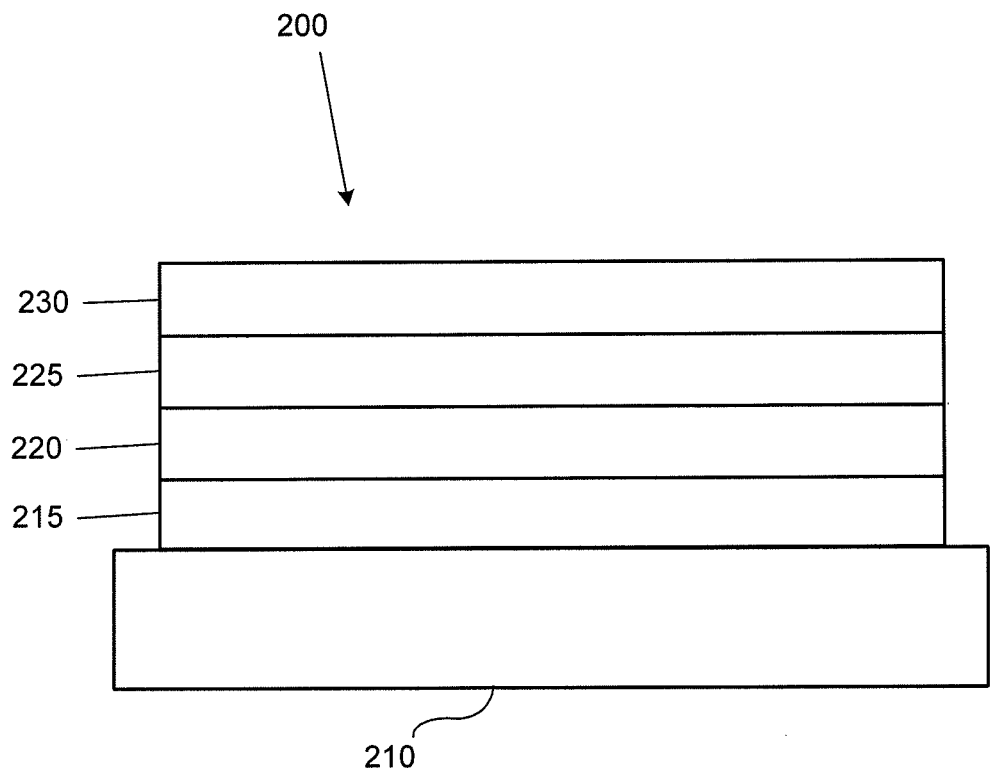
FIG. 2 shows an inverted organic light emitting device that does not have a separate electron transport layer.
Figure 3:
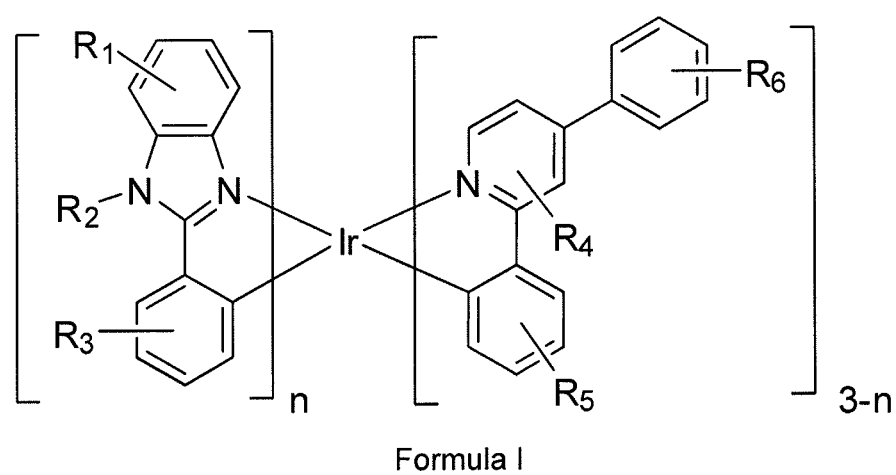
FIG. 3 shows a compound of Formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

A compound comprising a heteroleptic iridium complex having the formula:

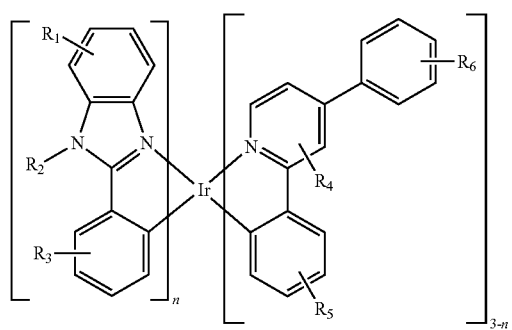

Formula I, is provided. $R_1$, $R_3$, $R_4$, $R_5$ and $R_6$ represent mono-, di-, tri- or tetra-substitution. $R_1$, $R_2$, $R_3$, $R_4$, $R_5$ and $R_6$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Additionally, $R_1$, $R_3$, $R_4$, $R_5$ and $R_6$ are optionally fused and may be further substituted, and n is 1 or 2.

In one embodiment, n is 2. In another embodiment, n is 1.

In one embodiment, $R_2$ is aryl or substituted aryl. In another embodiment, $R_2$ is a 2,6-disubstituted aryl. In one embodiment, $R_2$ is alkyl. In another embodiment, $R_2$ is

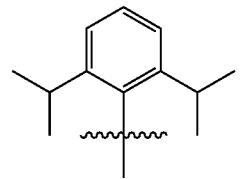

Compounds of Formula I were found to have broad yellow emission profiles, which is useful for both display and lighting applications where white light is necessary. Compounds of Formula I are also readily sublimed, enabling efficient purification and subsequent incorporation into OLEDs. In some instances, having alkyl substitution at $R_6$ can decrease the sublimation temperatures of compounds of Formula I without affecting the stability of the complex. Appropriate substitution at the $R_2$ position can increase the stability of compounds of Formula I. Without being bound by theory, it is believed that the use of 2,6-disubstituted aryl moieties can be advantageous due to increased steric bulk around the iridium center, which decreases the solid state packing of the compound, resulting in higher quantum efficiency and improved sublimation properties.

In one embodiment, $R_3$, $R_4$, $R_5$ and $R_6$ are each independently selected from the group consisting of hydrogen and alkyl, and wherein at least one of $R_3$, $R_4$, $R_5$ and $R_6$ is alkyl. In one embodiment, $R_5$ is aryl. In another embodiment, $R_6$ is aryl.

In one embodiment, $R_1$, $R_3$, and $R_5$ are hydrogen.

Specific non-limiting examples of a compound of Formula I are provided. In one embodiment, the compound is selected from the group consisting of:

Compound 1
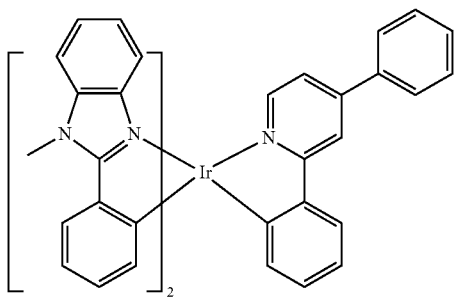
Compound 2
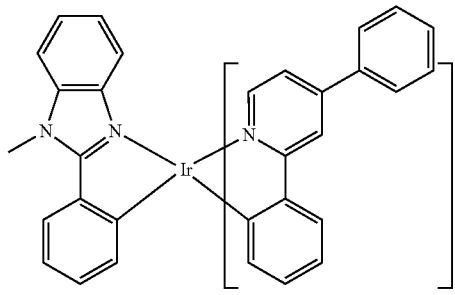
Compound 3
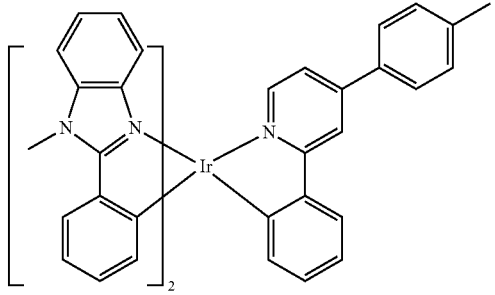
Compound 4
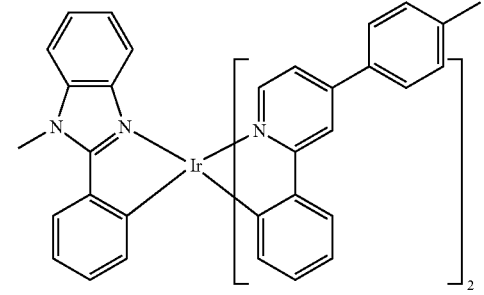
Compound 5
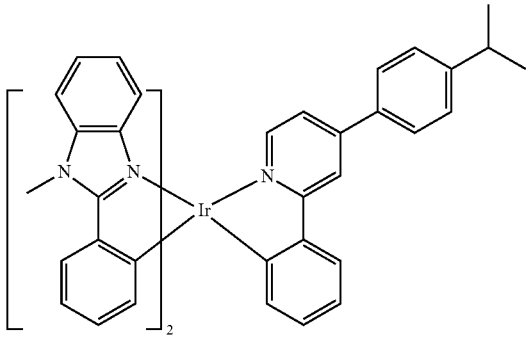
-continued
Compound 6
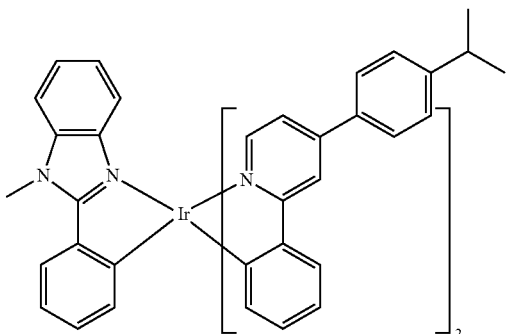
Compound 7
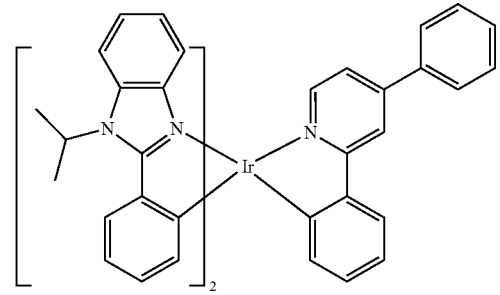
Compound 8
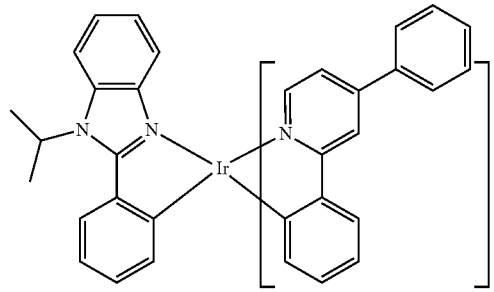
Compound 9
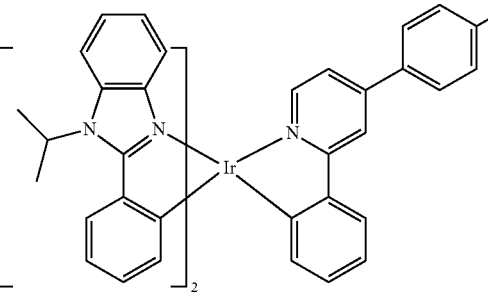
Compound 10
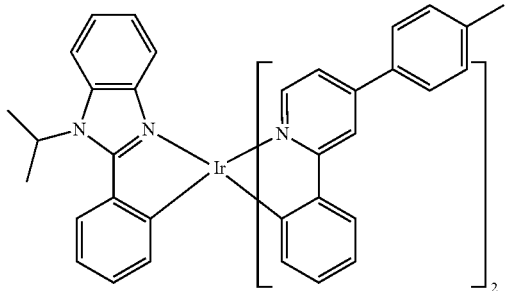

Compound 11
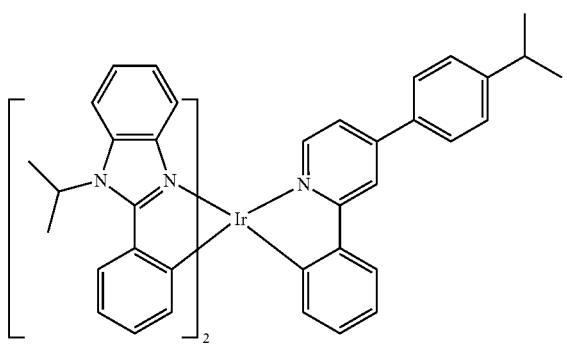
Compound 12
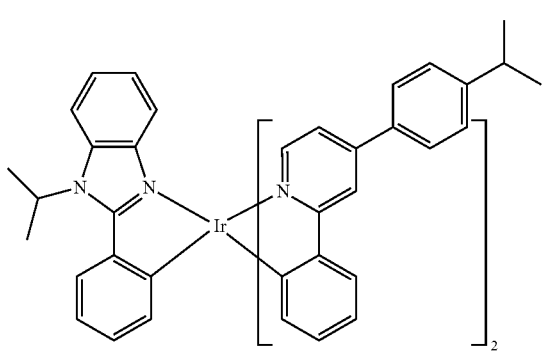
Compound 13
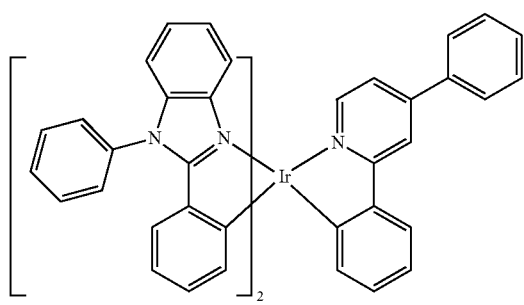
Compound 14
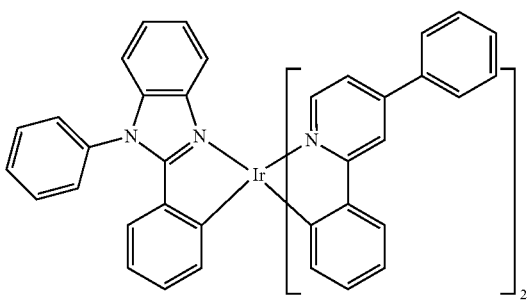
Compound 14
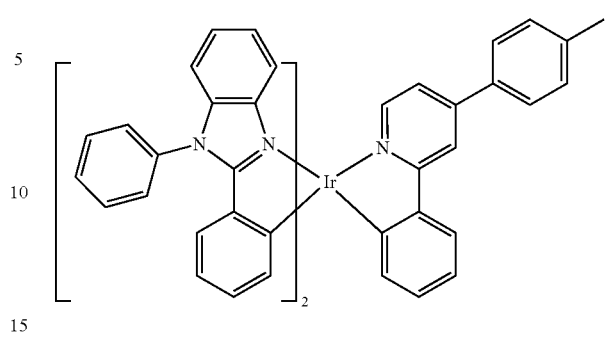
Compound 15
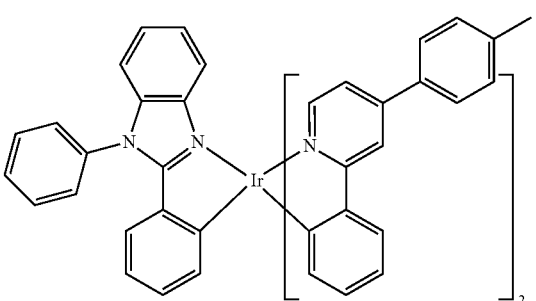
Compound 16
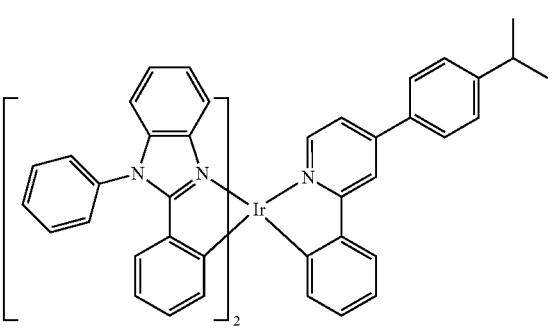
Compound 17
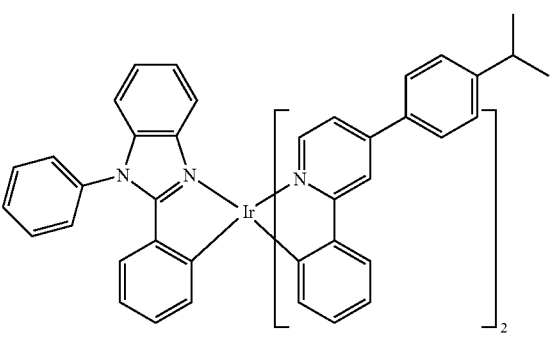

Compound 18
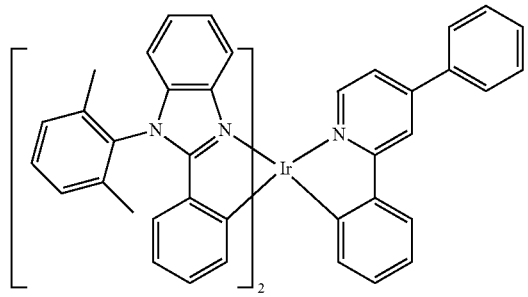
Compound 19
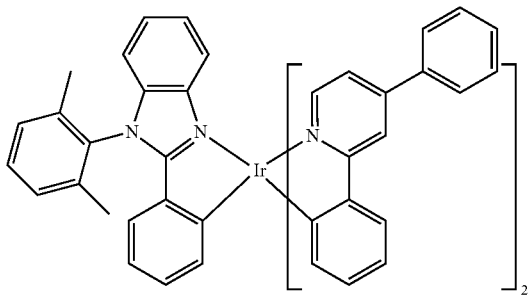
Compound 20
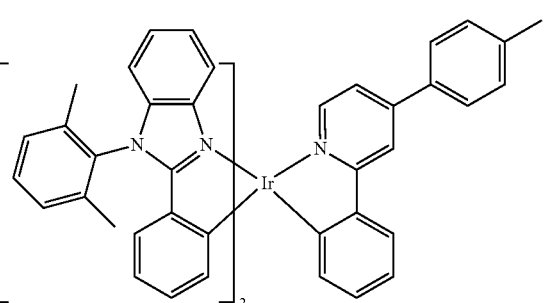
Compound 21
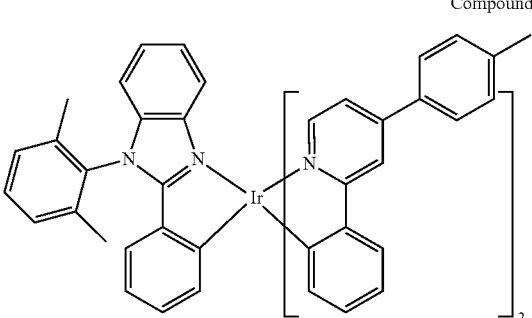
Compound 22
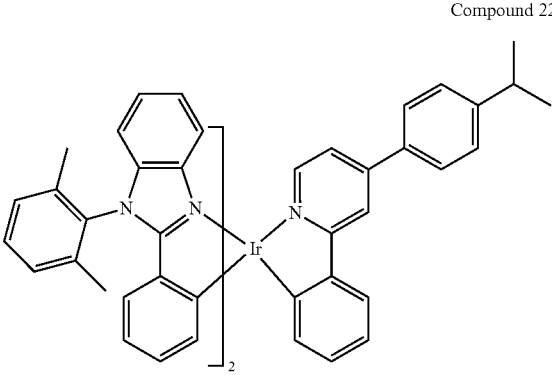
Compound 23
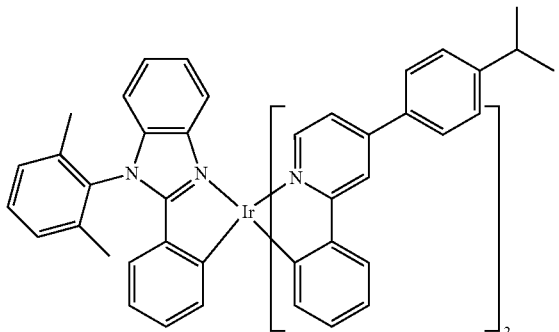
Compound 24
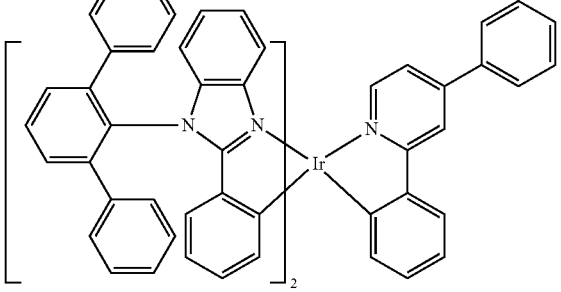
Compound 25
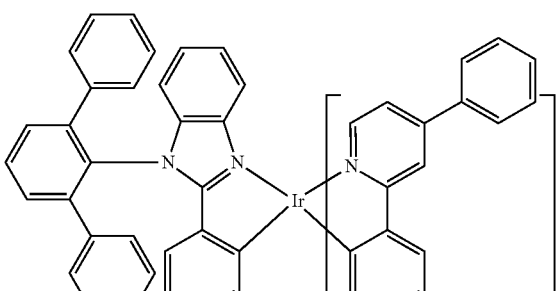
Compound 26
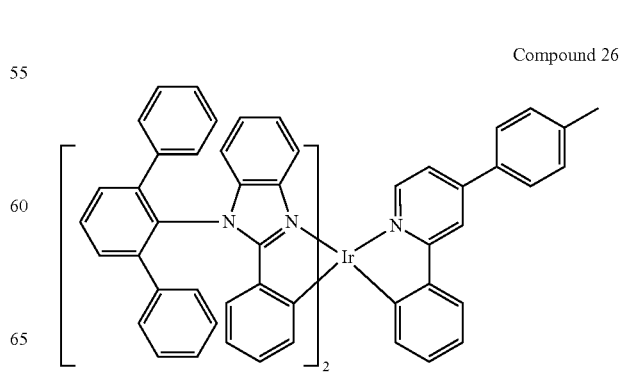

Compound 27
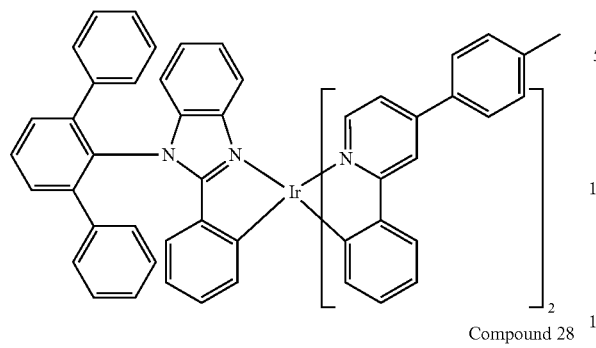
Compound 28
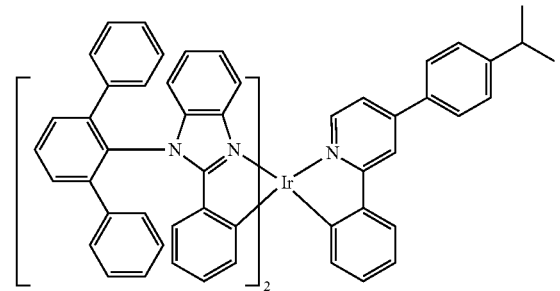
Compound 29
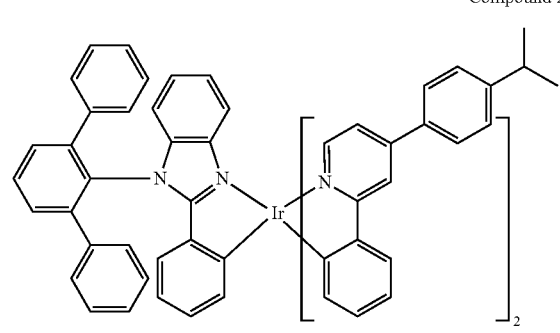
Compound 30
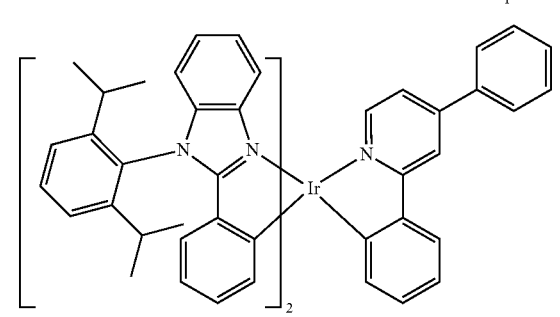
Compound 31
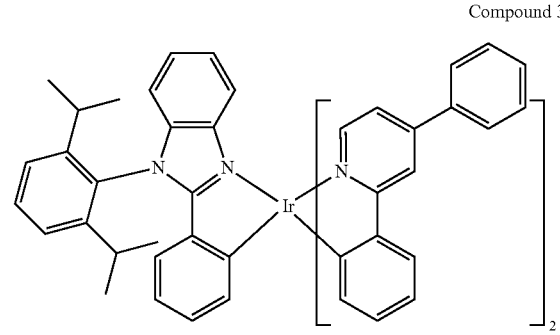
Compound 32
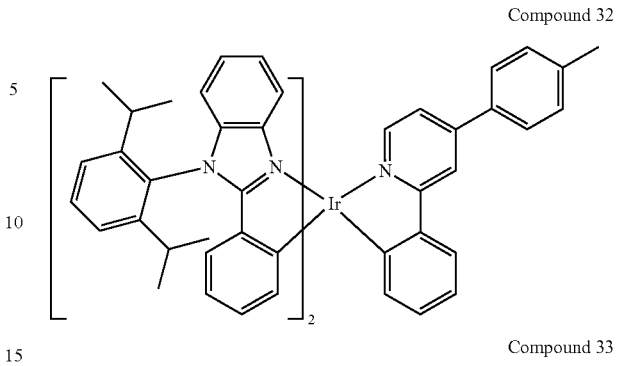
Compound 33
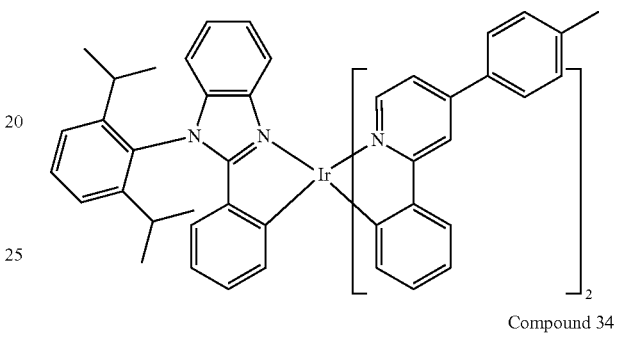
Compound 34
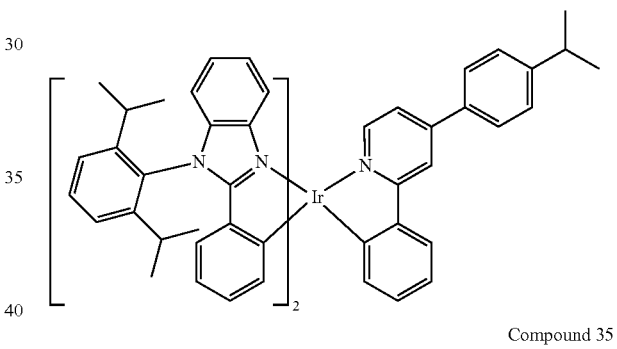
Compound 35
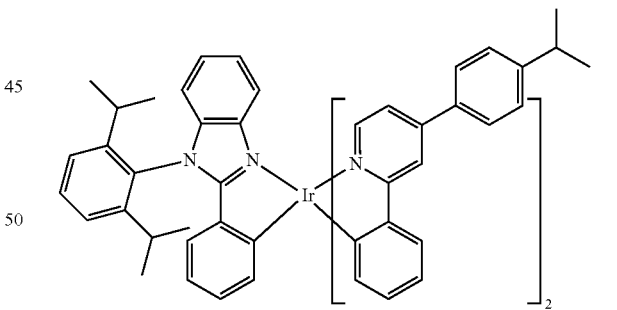
Compound 36
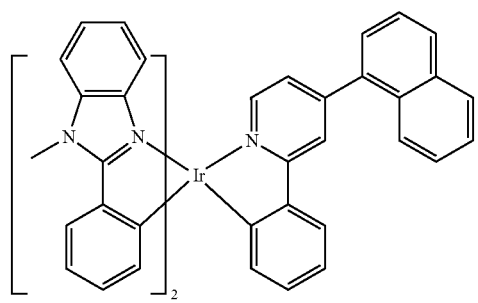

Compound 37
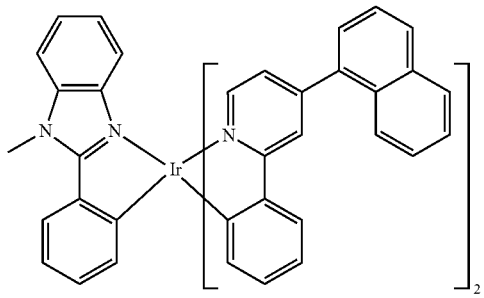
Compound 38
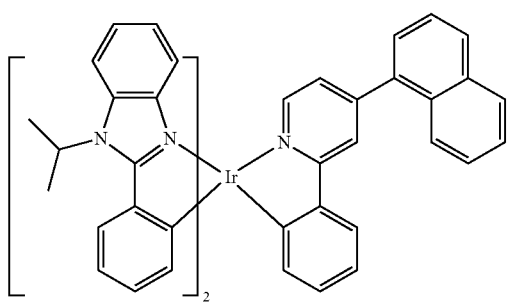
Compound 39
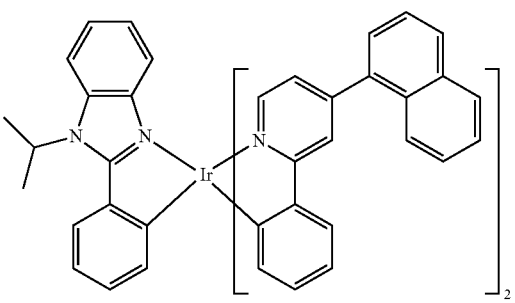
Compound 40
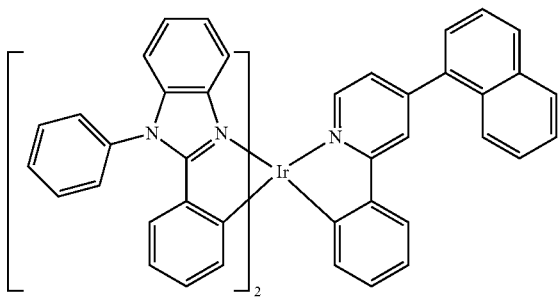
Compound 41
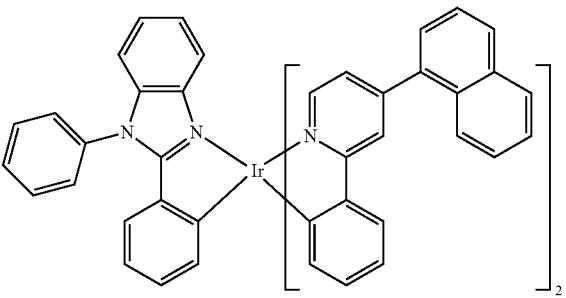
Compound 42
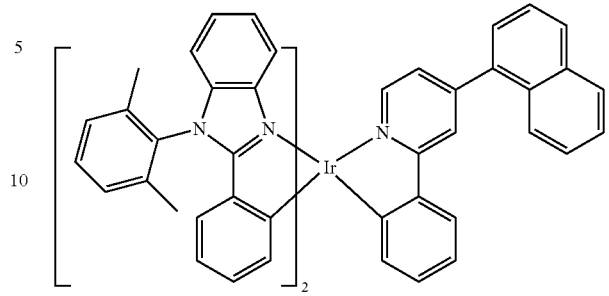
Compound 43
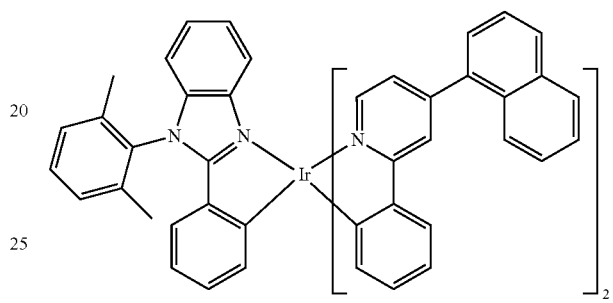
Compound 44
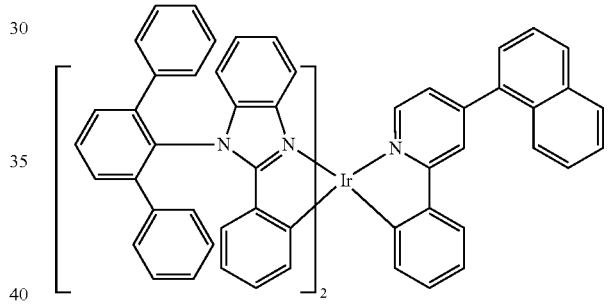
Compound 45
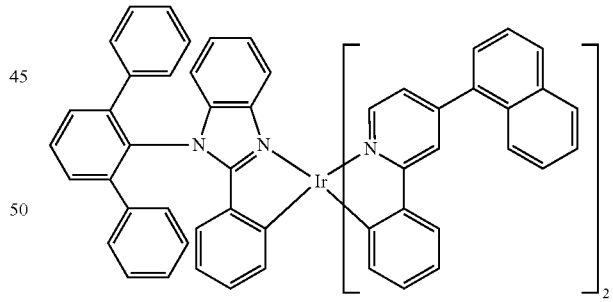
Compound 46
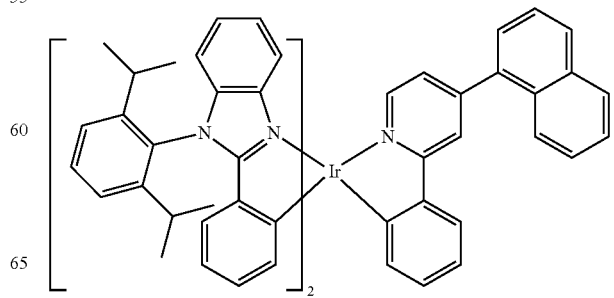

Compound 47
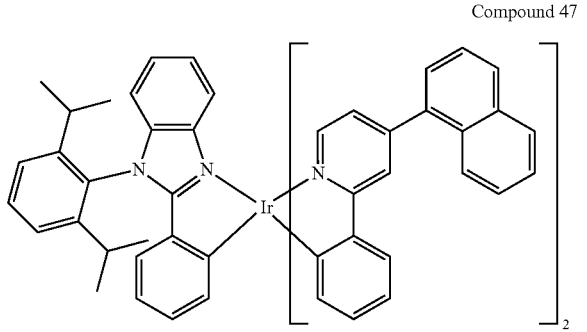
Compound 52
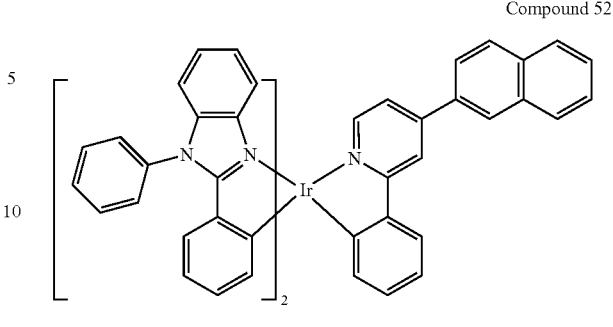
Compound 48
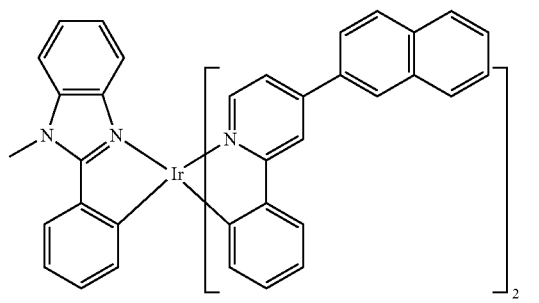
Compound 53
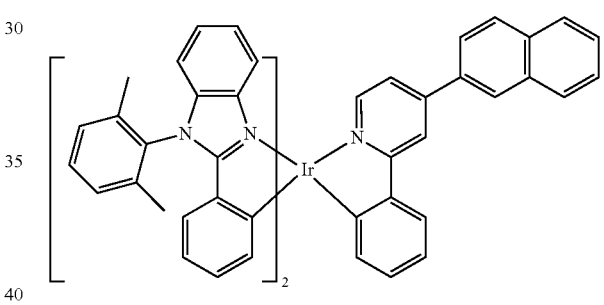
Compound 49
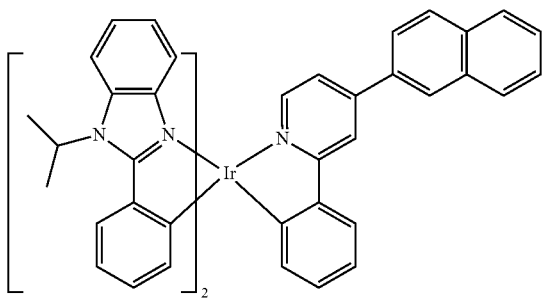
Compound 54
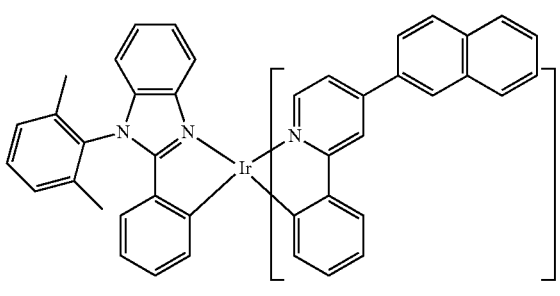
Compound 50
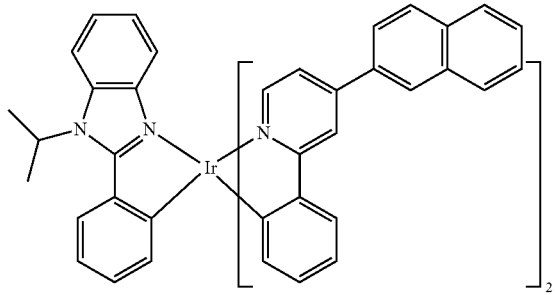
Compound 55
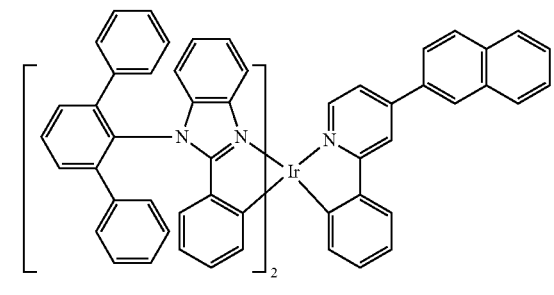
Compound 51
Compound 56

Compound 57
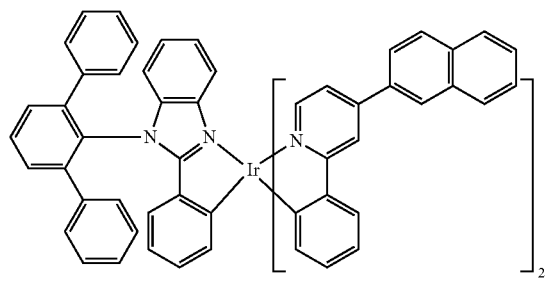
Compound 58
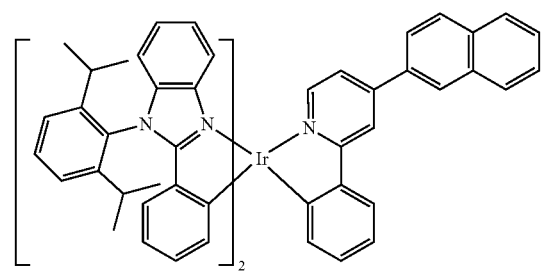
Compound 59
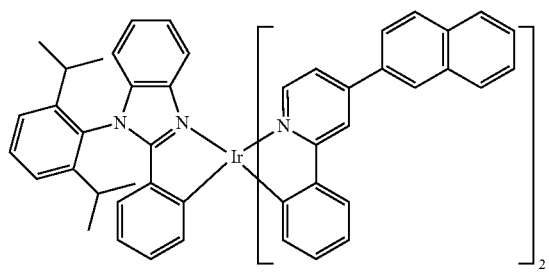
Compound 60
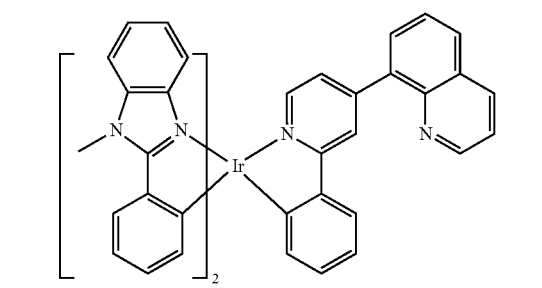
Compound 61
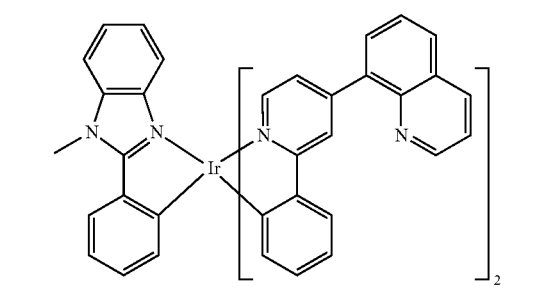
Compound 62
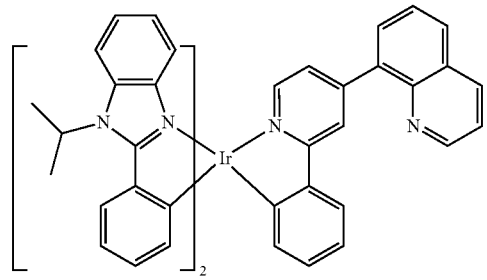
Compound 63
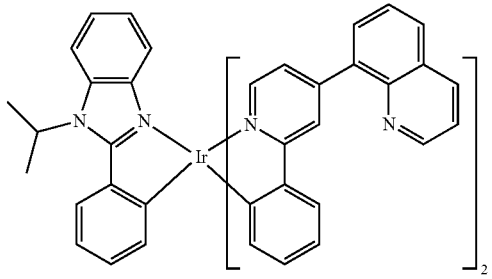
Compound 64
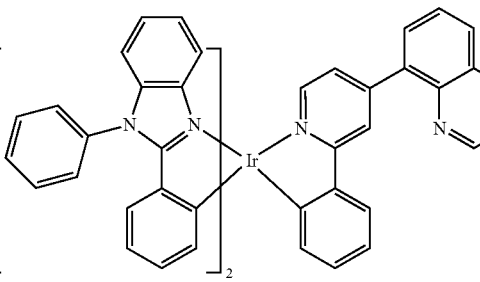
Compound 65
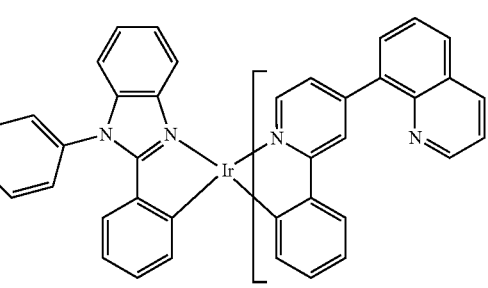
Compound 66
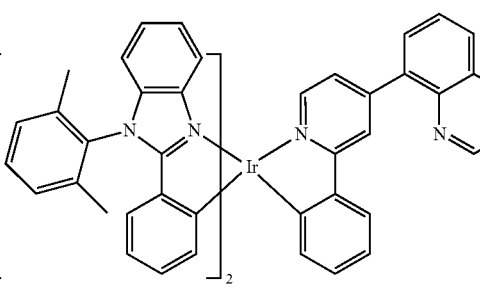

Compound 67
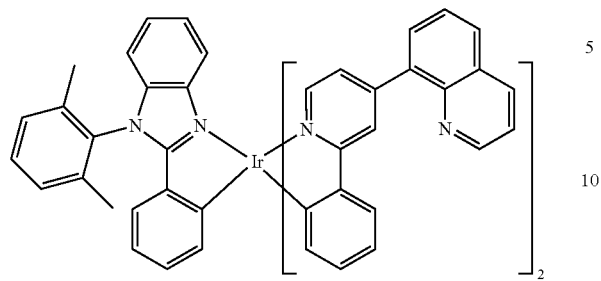
Compound 68
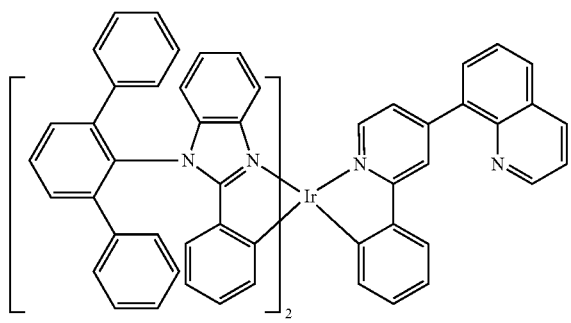
Compound 69
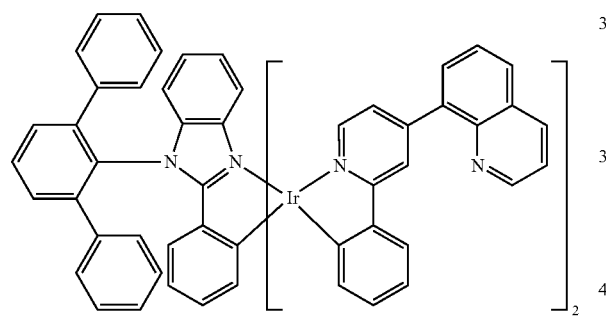
Compound 70
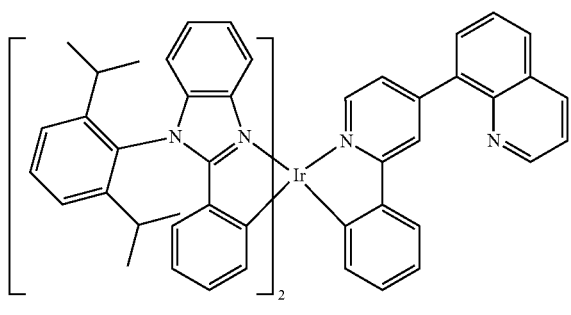
Compound 71
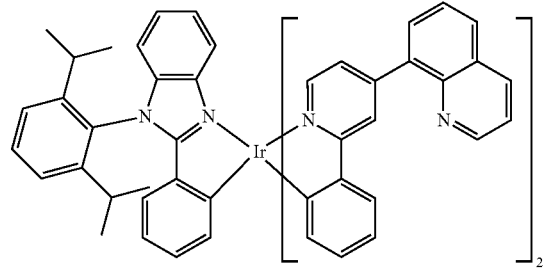
Compound 72
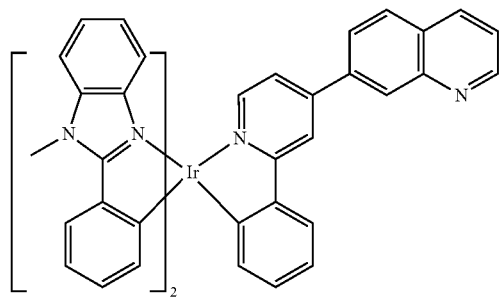
Compound 73
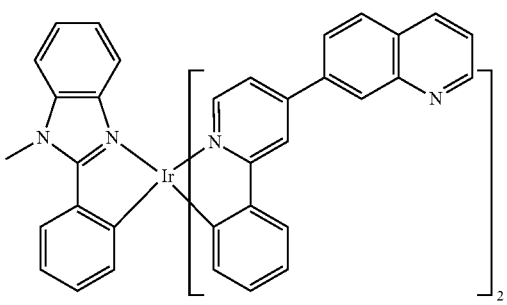
Compound 74
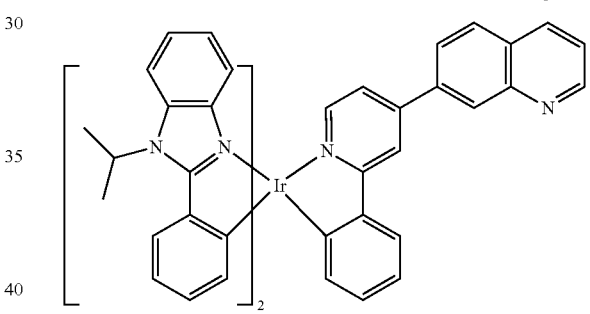
Compound 75
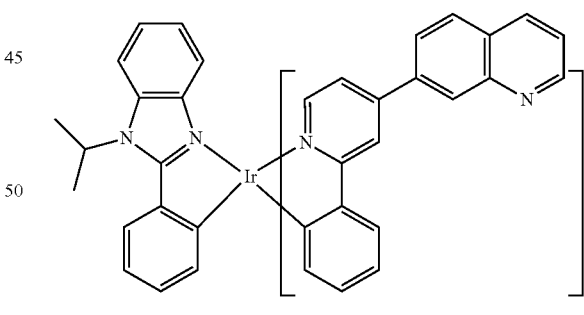
Compound 76
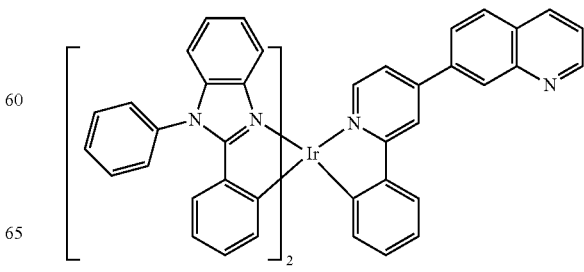

Compound 77
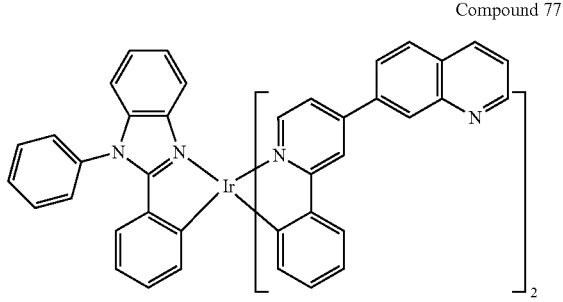
Compound 78
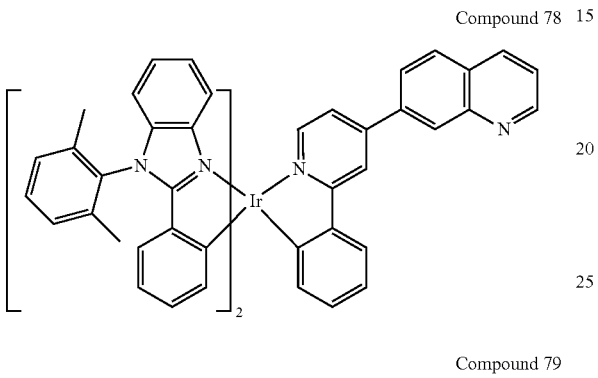
Compound 79
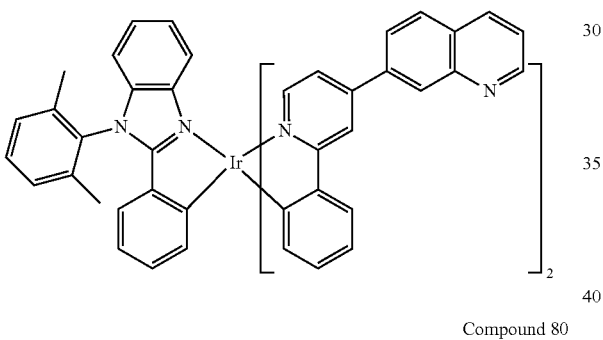
Compound 80
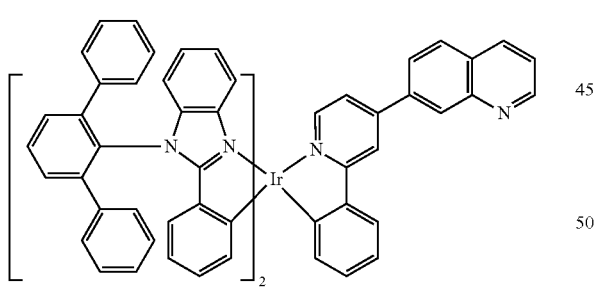
Compound 81
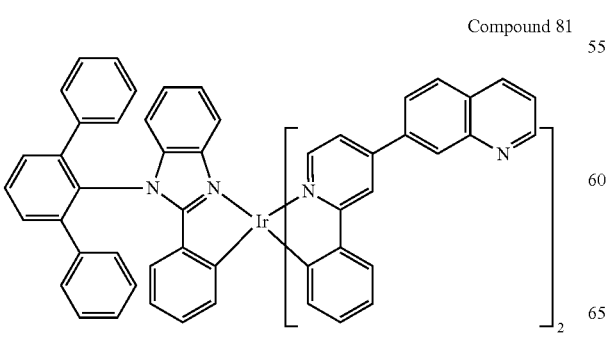
Compound 83
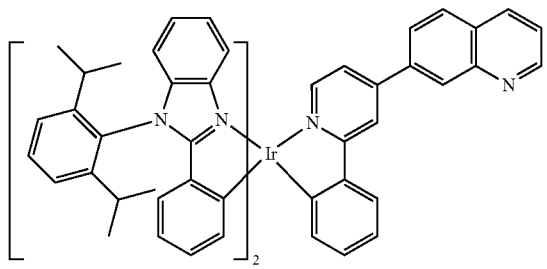
Compound 84
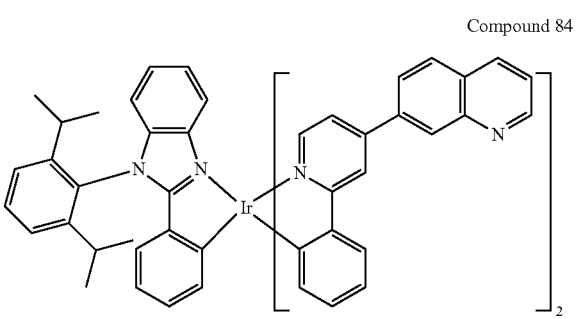
Compound 85
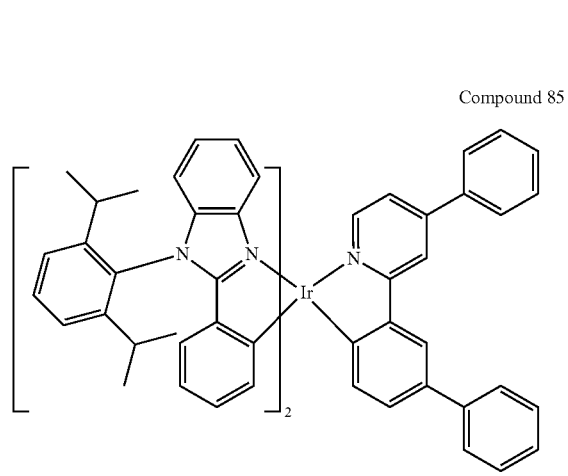
Compound 86
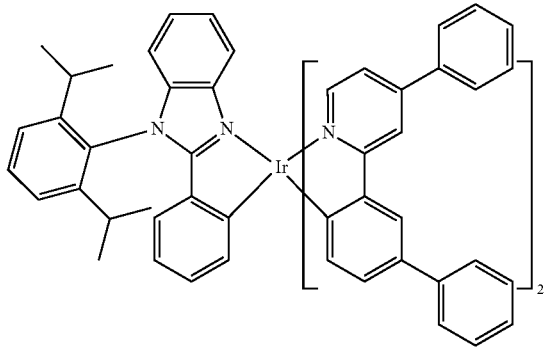

-continued
Compound 87
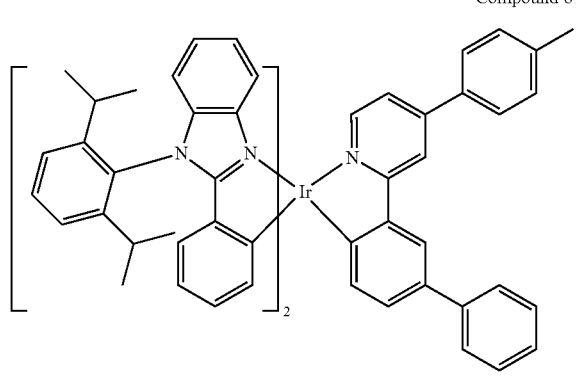
Compound 88
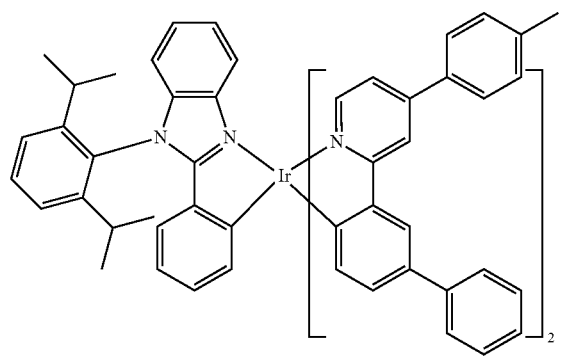
Compound 89
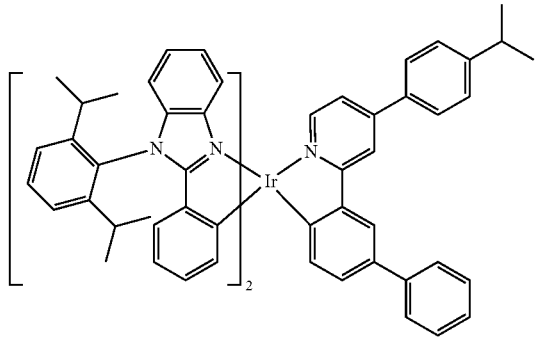
Compound 90
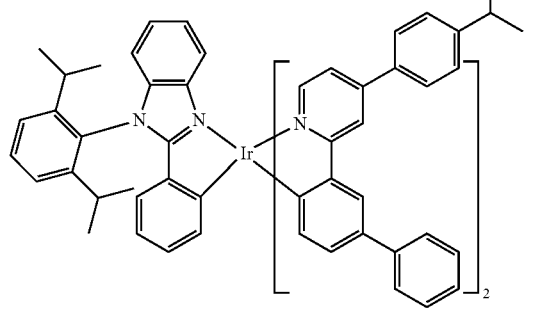
-continued
Compound 91
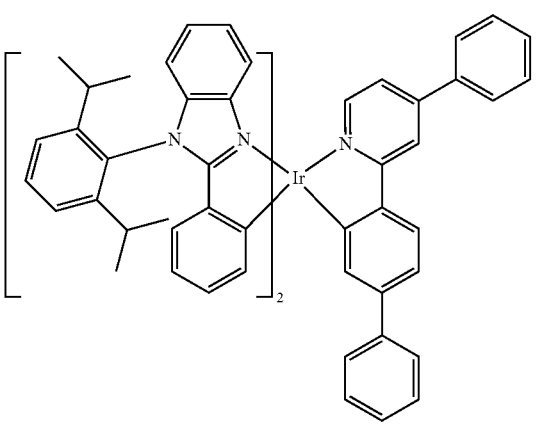
Compound 92
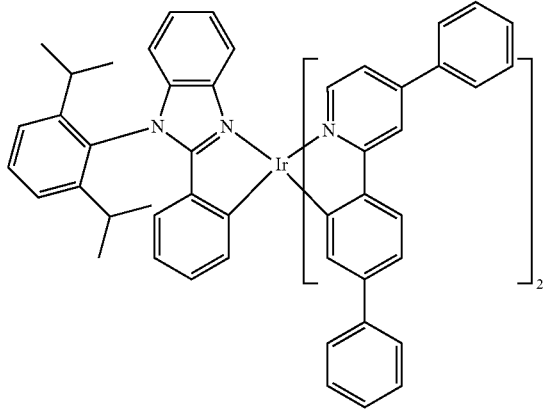
Compound 93
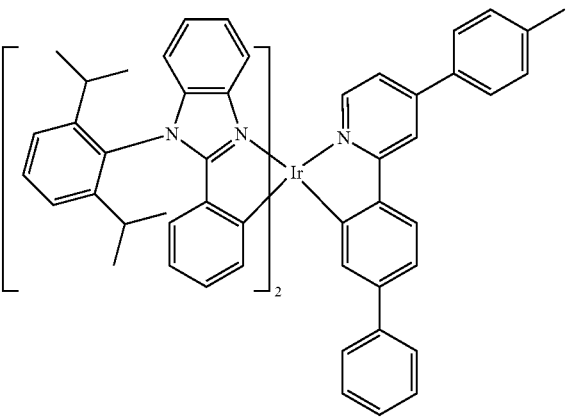

Compound 94
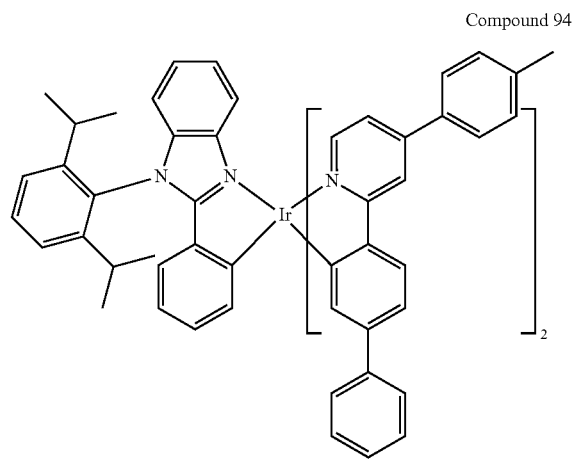
Compound 97
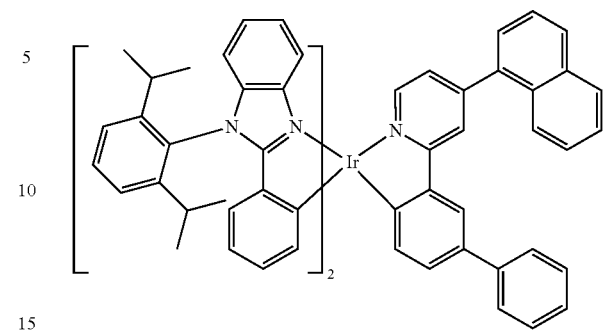
Compound 95
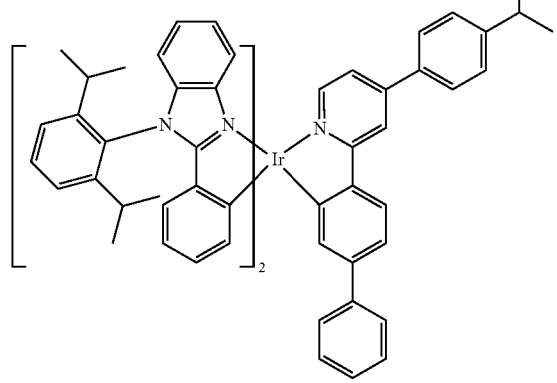
Compound 97
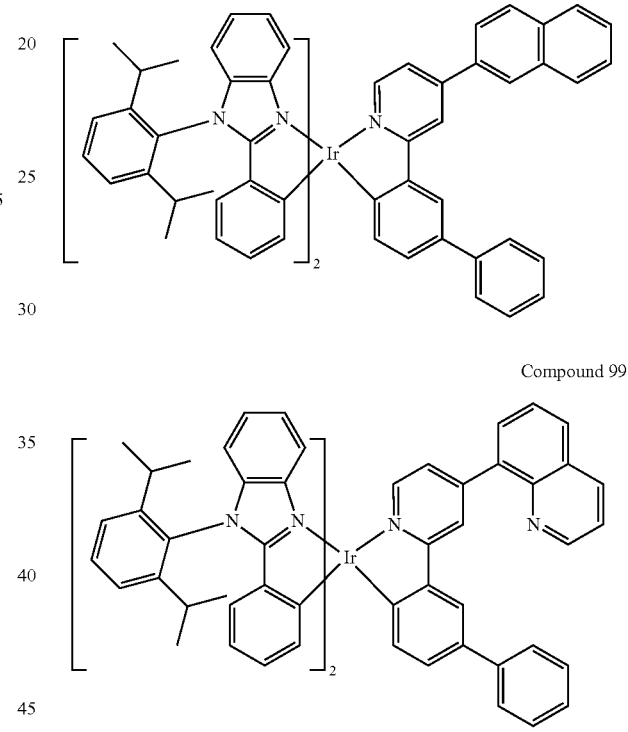
Compound 99
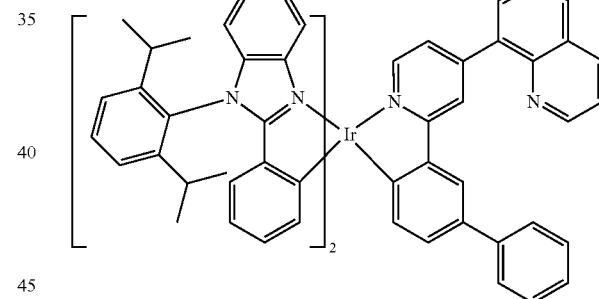
Compound 96
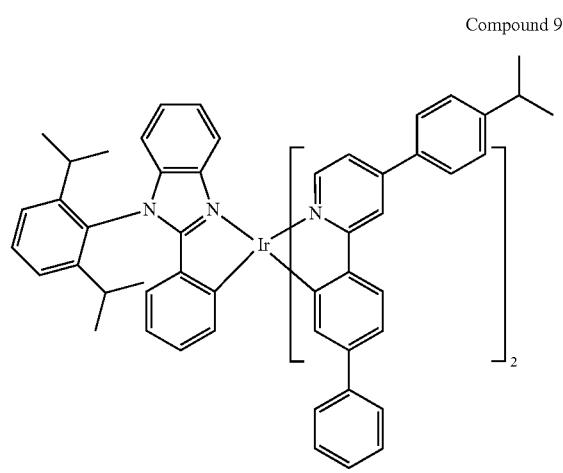
Compound 100
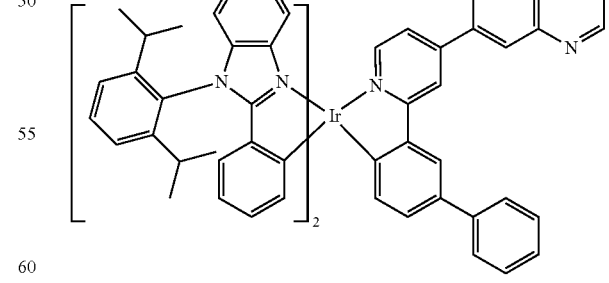
A first device is also provided. The first device comprises a first organic light emitting device, further comprising an anode, a cathode, and an organic layer, disposed between the anode and the cathode, comprising a compound having the formula:

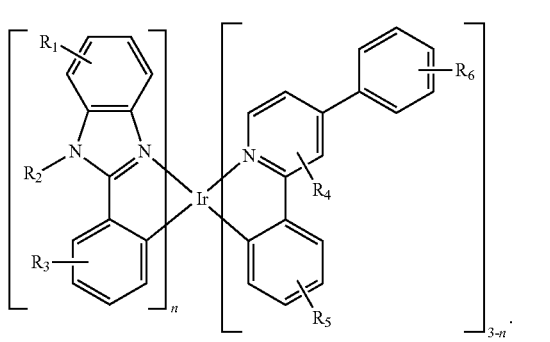

Formula I $R_1$, $R_3$, $R_4$, $R_5$ and $R_6$ represent mono-, di-, tri- or tetra-substitution. $R_1$, $R_2$, $R_3$, $R_4$, $R_5$ and $R_6$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Additionally, $R_1$, $R_3$, $R_4$, $R_5$ and $R_6$ are optionally fused and may be further substituted, and n is 1 or 2.

In one embodiment, the organic layer is an emissive layer and the compound is an emissive dopant. In one embodiment, the organic layer is an emissive layer and the compound is a non-emissive dopant. In another embodiment, the organic layer further comprises a host.

In one embodiment, the host comprises a triphenylene containing benzo-fused thiophene or benzo-fused furan, wherein any substituent in the compound is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CHC_nH_{2n+1}$, $Ar_1$, $Ar_1-Ar_2$, $C_nH_{2n}-Ar_1$, or no substitution. $Ar_1$ and $Ar_2$ are independently selected from the group consisting of benzene, biphenyl, naphthalene, triphenylene, carbazole, and heteroaromatic analogs thereof, and n is from 1 to 10.

In one embodiment, the host has the formula:

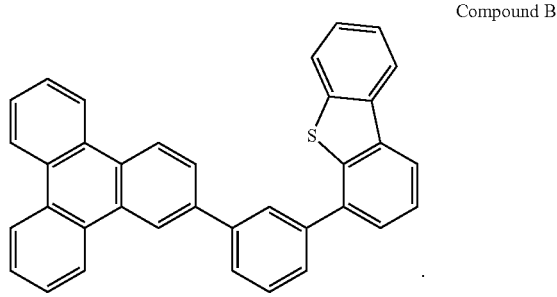 [SMILES: c1cc(-c2ccc3c4ccccc4c4ccccc4c3c2)cc(-c2cccc3c2sc2ccccc23)c1]

Compound B

In one embodiment, the host is a metal complex.

As discussed above, OLEDs that incorporate compounds of Formula I have broad yellow emission profiles, as well as high quantum efficiencies and long commercial lifetimes. A device capable of broad yellow emission is particularly desirable in white illumination sources.

The quality of white illumination sources can be fully described by a simple set of parameters. The color of the light source is given by its CIE chromaticity coordinates x and y (1931 2-degree standard observer CIE chromaticity). The CIE coordinates are typically represented on a two dimensional plot. Monochromatic colors fall on the perimeter of the horseshoe shaped curve starting with blue in the lower left, running through the colors of the spectrum in a clockwise direction to red in the lower right. The CIE coordinates of a light source of given energy and spectral shape will fall within the area of the curve. Summing light at all wavelengths uniformly gives the white or neutral point, found at the center of the diagram (CIE x,y-coordinates, 0.33, 0.33). Mixing light from two or more sources gives light whose color is represented by the intensity weighted average of the CIE coordinates of the independent sources. Thus, mixing light from two or more sources can be used to generate white light.

When considering the use of these white light sources for illumination, the CIE color rendering index (CRI) may be considered in addition to the CIE coordinates of the source. The CRI gives an indication of how well the light source will render colors of objects it illuminates. A perfect match of a given source to the standard illuminant gives a CRI of 100. Though a CRI value of at least 70 may be acceptable for certain applications, a preferred white light source may have a CRI of about 80 or higher.

The compounds of Formula I have yellow emission profiles with significant red and green components. The addition of a blue emitter, i.e. an emitter with a peak wavelength of between 400 to 500 nanometers, together with appropriate filters on OLEDs incorporating the compound of Formula I allows for the reproduction of the RGB spectrum. In some embodiments, OLEDs that incorporate compounds of Formula I are used for color displays (or lighting applications) using only two types of emissive compounds: a yellow emitter of Formula I and a blue emitter. A color display using only two emissive compounds: a broad yellow emitter of Formula I and a blue emitter, may employ a color filter to selectively pass the red, green, and blue color components of a display. The red and green components can both come from a broad yellow emitter of Formula I.

In one embodiment, the first device is a consumer product. In another embodiment, the first device is an organic light-emitting device. In one embodiment, the first device further comprises a second emissive dopant having a peak wavelength of between 400 to 500 nanometers. In one embodiment, the second emissive dopant is a fluorescent emitter. In another embodiment, the second emissive dopant is a phosphorescent emitter.

In one embodiment, the first device comprises a lighting panel. In one embodiment, the first device further comprises a first organic light-emitting device comprising a compound of Formula I and a second light-emitting device separate from the first organic light-emitting device comprising an emissive dopant having a peak wavelength of between 400 to 500 nanometers. The first and second light-emitting devices can be placed in any suitable spatial arrangement, depending on the needs of the desired display or lighting application.

In another embodiment, the first device comprises an organic-light emitting device having a first emissive layer comprising a compound of Formula I and a second emissive layer comprising an emissive dopant having a peak wavelength of between 400 to 500 nanometers. In this embodiment, the compound of Formula I and a blue emitter are located within the same OLED stack. The first emissive layer and the second emissive layer may have one or more other layers in between them.

Device Examples

All example devices were fabricated by high vacuum ($<10^{-7}$ Torr) thermal evaporation. The anode electrode is 1200 Å of indium tin oxide (ITO). The cathode consisted of 10 Å of LiF followed by 1,000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

The organic stack of the device examples consisted of sequentially, from the ITO surface, 100 Å of Compound A as the hole injection layer (HIL), 300 Å of 4,4'-bis[N-(1-naphthyl)-N-phenylamino]biphenyl (alpha-NPD) as the hole transporting layer (HTL), 300 Å of 10-15 wt % of compound of Formula I doped in with Compound B as host as the emissive layer (EML), 50 Å or 100 Å of Compound B as blocking layer (BL), 400 Å of Alq (tris-8-hydroxyquinoline aluminum) as the electron transport layer (ETL).

The device results and data are summarized in Tables 1 and 2 from those devices. As used herein, NPD, Alq, Compound A, Compound B, and Compound X have the following structures:

Compound A

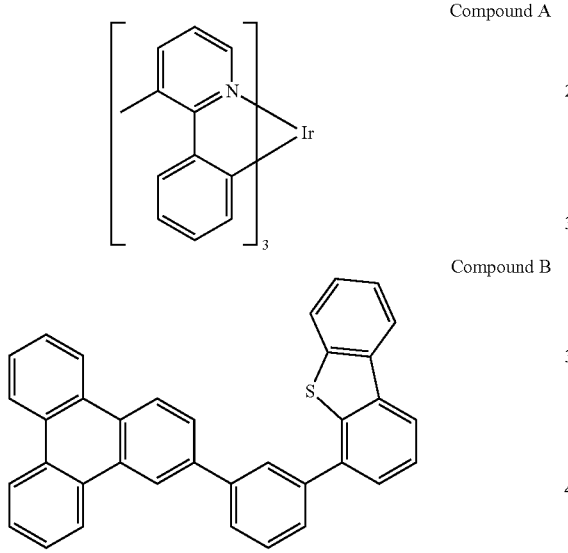

Compound B

Compound X

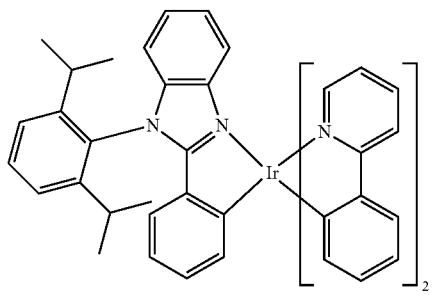

NPD

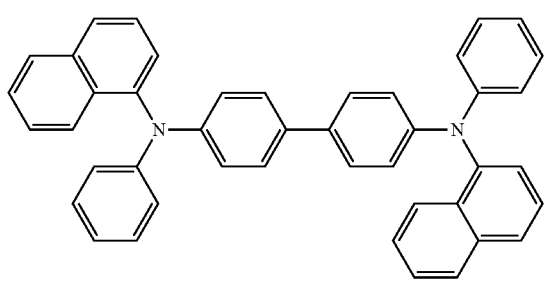

Alq

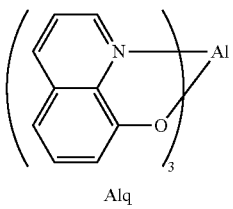

TABLE 1

VTE Phosphorescent OLEDs

| Example | HIL | HTL | EML (300 Å, doping %) | | ETL 2 | ETL 1 |
|---|---|---|---|---|---|---|
| Example 1 Comp. 58 | Compound A 100 Å | NPD 300 Å | Compound B | Compound 58 10% | Compound B 50 Å | Alq 400 Å |
| Example 2 Comp. 30 | Compound A 100 Å | NPD 300 Å | Compound B | Compound 30 10% | Compound B 50 Å | Alq 400 Å |
| Comparative Example Comp. X | Compound A 100 Å | NPD 300 Å | Compound B | Compound X 10% | Compound B 100 Å | Alq 400 Å |

TABLE 2

VTE Device Data

| Example | x | y | $\lambda_{max}$ | FWHM (nm) | Voltage (V) | LE (Cd/A) | EQE (%) | PE (lm/W) | LT80% (h) |
|---|---|---|---|---|---|---|---|---|---|
| Example 1 Comp. 58 | 0.504 | 0.491 | 572 | 78 | 6.1 | 59.1 | 20.3 | 30.3 | 505 |

TABLE 2-continued

VTE Device Data

| Example | x | y | $\lambda_{max}$ | FWHM (nm) | Voltage (V) | LE (Cd/A) | EQE (%) | PE (lm/W) | LT80% (h) |
|---|---|---|---|---|---|---|---|---|---|
| Example 2 Comp. 30 | 0.450 | 0.540 | 558 | 74 | 5.9 | 58.7 | 17.4 | 31.4 | 280 |
| Comparative Example Comp. X | 0.325 | 0.620 | 519 | 72 | 5.7 | 50.5 | 14.0 | 27.6 | 270 |

The device data show that Compounds of Formula I are effective yellow emitters with broad line shape (desirable for use in white light devices), with high efficiency and commercially useful lifetimes. Comparative Example Compound X is a green emitter, emitting at a peak wavelength of 519 nm, with a FWHM (full width at half max) of 72 nm. By adding an additional phenyl ring to the pyridine ring, Compound 58 emitted at 572 nm and Compound 30 emitted at 558 nm, showing a red-shift in their emission spectra while broadening the emission to a FWHM of 78 nm and 74 nm respectively, which make them useful broad emitters for white light applications. In addition, compounds of Formula I have higher efficiencies [Compound 58 (59.1 cd/A, 20.3%, 30.3 μm/W) and Compound 30 (58.7 μm/W, 17.4%, 31.4 lm/W)] versus the comparative example (50.5 cd/A, 14.0%, 27.6 μm/W) while maintaining comparable voltages. Finally, Compound 30 has a slightly higher device lifetime (280 h) than Comparative Compound X (270 h), while Compound 30 has a device lifetime almost twice as long (505 h).

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

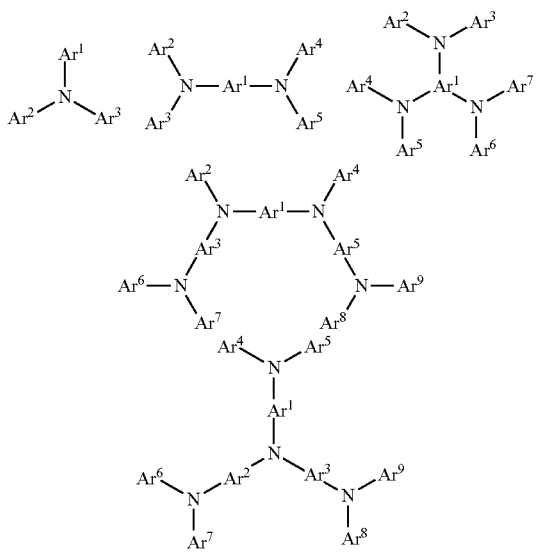

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

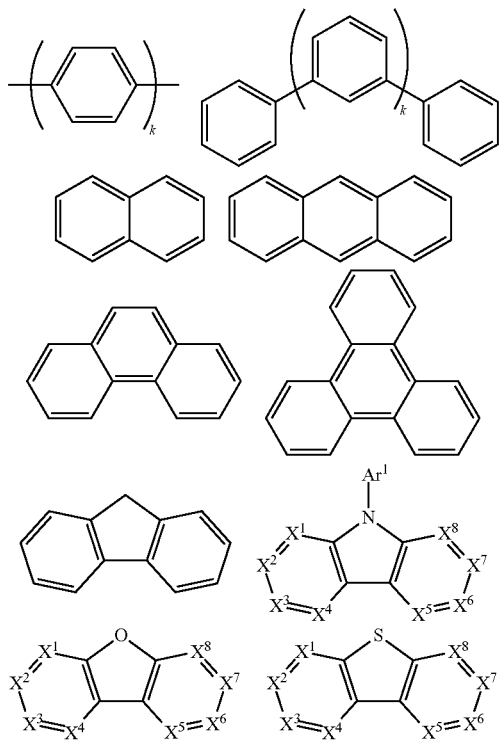

k is an integer from 1 to 20; $X^1$ to $X^8$ is C (including CH) or N; $Ar^1$ has the same group defined above.

Examples of metal complexes used in HIL or HTL include, but not limit to the following general formula:

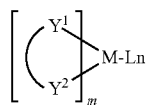

M is a metal, having an atomic weight greater than 40; $(Y^1-Y^2)$ is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1-Y^2)$ is a 2-phenylpyridine derivative.

In another aspect, $(Y^1-Y^2)$ is a carbene ligand.

In another aspect, M is selected from Ir, Pt, Os, and Zn.

In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host are preferred to have the following general formula:

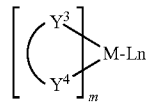

M is a metal; $(Y^3-Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

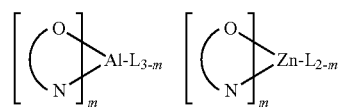

(O—N) is a bidentate ligand, having metal coordinated to atoms O and N.

In another aspect, M is selected from Ir and Pt.

In a further aspect, $(Y^3-Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

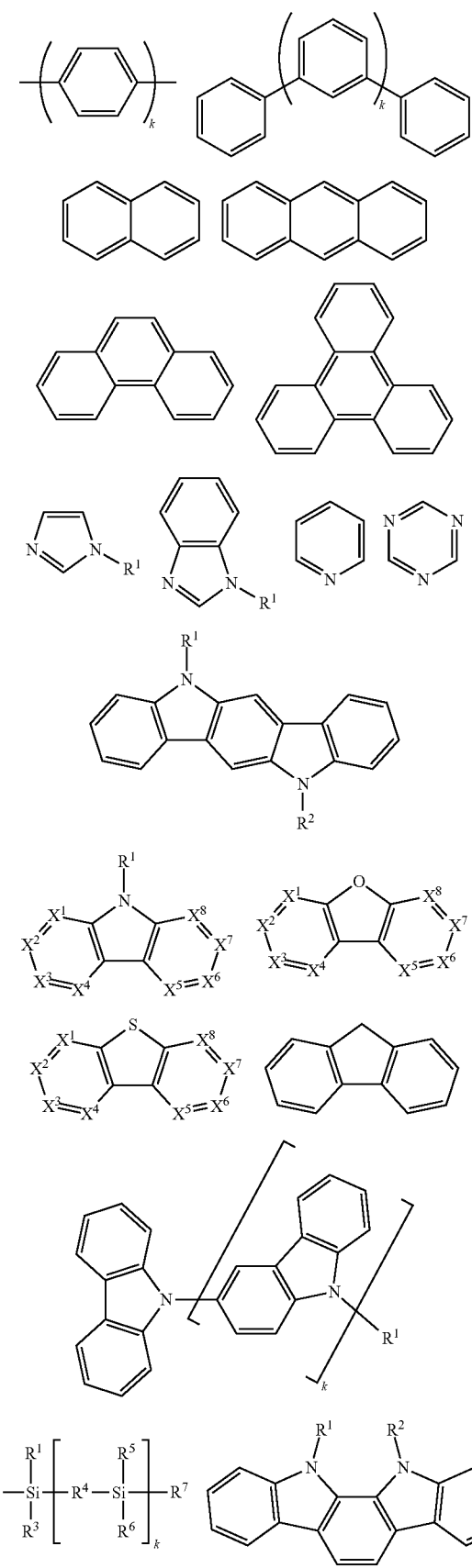

R[1] to R[7] is independently selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

k is an integer from 0 to 20.

X[1] to X[8] is selected from C (including CH) or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule used as host described above.

In another aspect, compound used in HBL contains at least one of the following groups in the molecule:

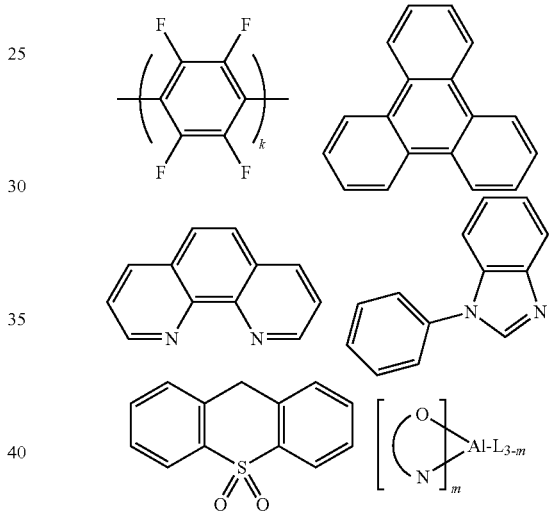

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

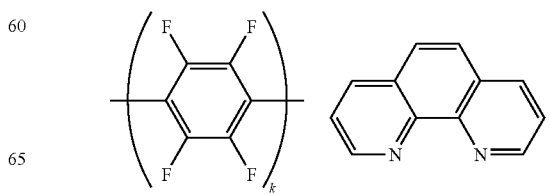

-continued

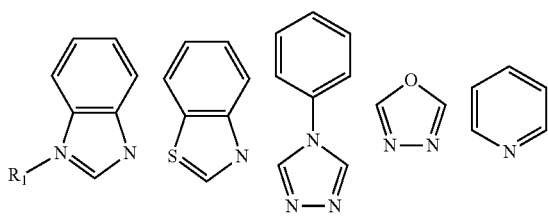

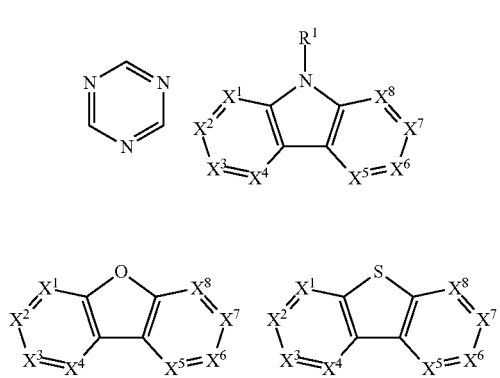

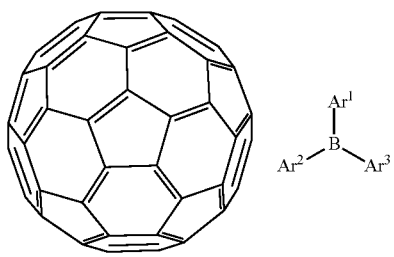

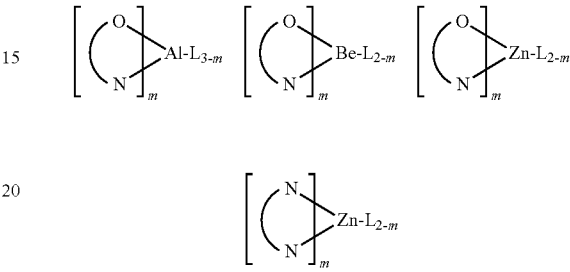

$R^1$ is selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from C (including CH) or N.

In another aspect, the metal complexes used in ETL contains, but not limit to the following general formula:

$$\left[ \left( \overset{O}{\underset{N}{\frown}} \right) Al\text{-}L_{3-m} \right]_m \quad \left[ \left( \overset{O}{\underset{N}{\frown}} \right) Be\text{-}L_{2-m} \right]_m \quad \left[ \left( \overset{O}{\underset{N}{\frown}} \right) Zn\text{-}L_{2-m} \right]_m$$

$$\left[ \left( \overset{N}{\underset{N}{\frown}} \right) Zn\text{-}L_{2-m} \right]_m$$

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 3 below. Table 3 lists non-limiting classes of materials, non-limiting examples of compounds for each class, and references that disclose the materials.

TABLE 3

| MATERIAL | EXAMPLES OF MATERIAL | PUBLICATIONS |
|---|---|---|
| Hole injection materials | | |
| Phthalocyanine and porphryin compounds | | Appl. Phys. Lett. 69, 2160 (1996) |

TABLE 3-continued
| MATERIAL | EXAMPLES OF MATERIAL | PUBLICATIONS |
|---|---|---|
| Starburst triarylamines | 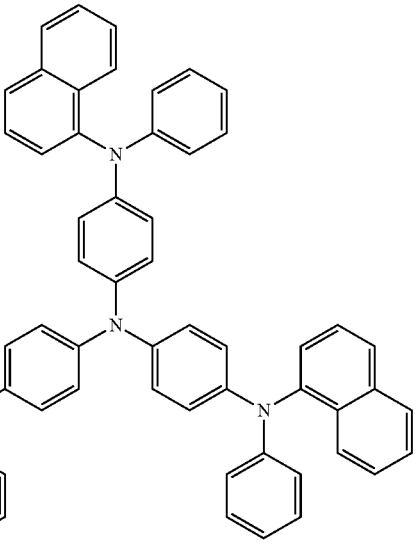 | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polythiophene) | 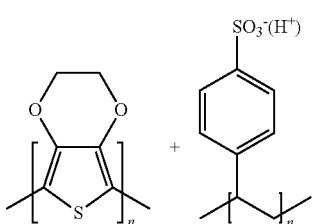 | Synth. Met. 87, 171 (1997) WO2007002683 |
| Phosphonic acid and sliane SAMs | 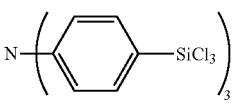 | US20030162053 |

TABLE 3-continued
| MATERIAL | EXAMPLES OF MATERIAL | PUBLICATIONS |
|---|---|---|
| Triarylamine or polythiophene polymers with conductivity dopants | 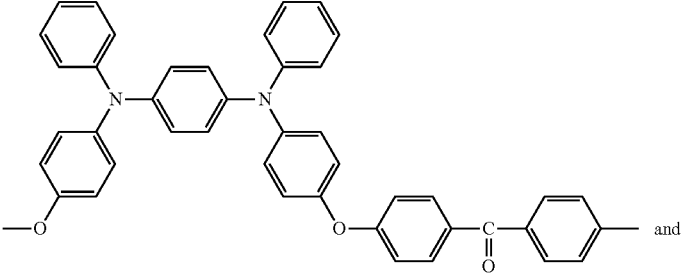 and 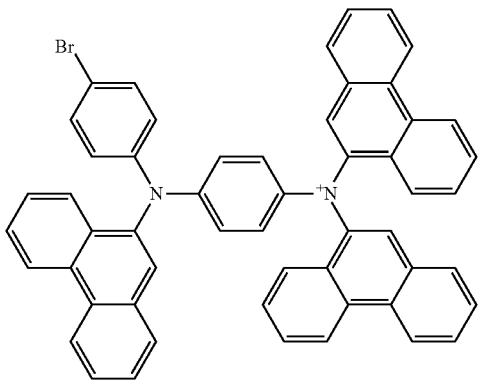 [SMILES: Brc1ccc(N(c2ccc([NH+](c3cc4ccccc4c4ccccc34)c3cc4ccccc4c4ccccc34)cc2)c2cc3ccccc3c3ccccc23)cc1] 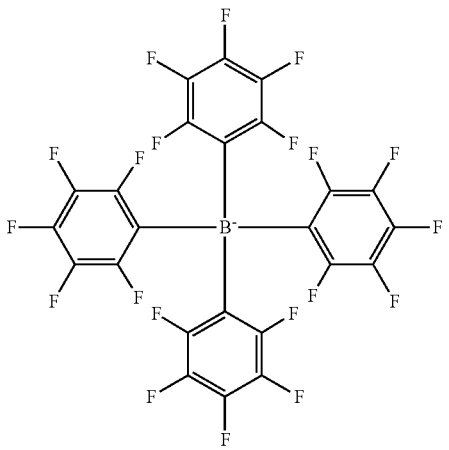 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |
| Arylamines complexed with metal oxides such as molybdenum and tungsten oxides | 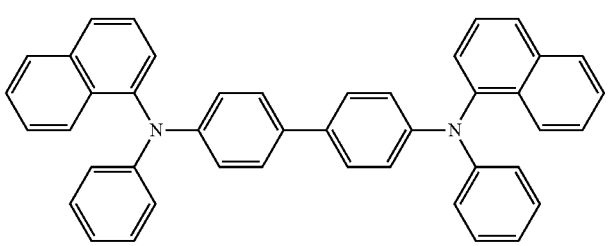 [SMILES: c1ccc(N(c2ccc(-c3ccc(N(c4ccccc4)c4cccc5ccccc45)cc3)cc2)c2cccc3ccccc23)cc1] + $MoO_x$ | SID Symposium Digest, 37, 923 (2006) WO2009018009 |

TABLE 3-continued

| MATERIAL | EXAMPLES OF MATERIAL | PUBLICATIONS |
|---|---|---|
| p-type semiconducting organic complexes | | US20020158242 |
| Metal organometallic complexes | | US20060240279 |
| Cross-linkable compounds | | US20080220265 |

Hole transporting materials

| | | |
|---|---|---|
| Triarylamines (e.g., TPD, α-NPD) | | Appl. Phys. Lett. 51, 913 (1987) |
| | | U.S. Pat. No. 5,061,569 |

US 9,212,197 B2
49 50
TABLE 3-continued
| MATERIAL | EXAMPLES OF MATERIAL | PUBLICATIONS |
|---|---|---|
| | 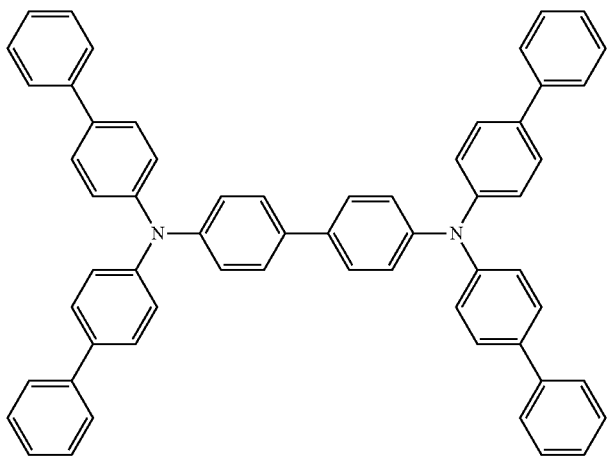 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 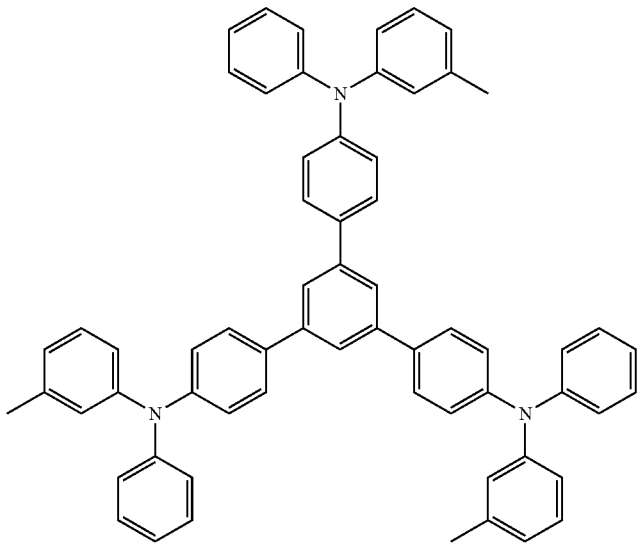 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 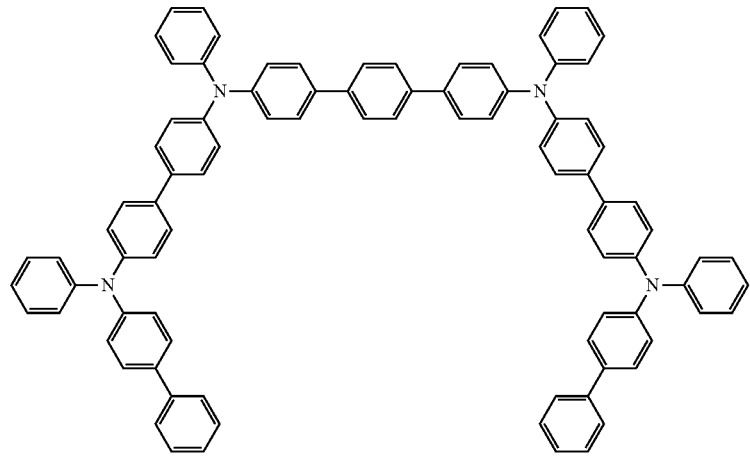 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE 3-continued

| MATERIAL | EXAMPLES OF MATERIAL | PUBLICATIONS |
|---|---|---|
| | (chemical structure) | Appl. Phys. Lett. 90, 183503 (2007) |
| Triarylamine on spirofluorene core | (chemical structure) | Synth. Met. 91, 209 (1997) |
| Arylamine carbazole compounds | (chemical structure) | Adv. Mater. 6, 677 (1994), US20080124572 |
| Triarylamine with (di)benzothiophene/ (di)benzofuran | (chemical structure) | US20070278938, US20080106190 |

TABLE 3-continued

| MATERIAL | EXAMPLES OF MATERIAL | PUBLICATIONS |
| --- | --- | --- |
| Indolo-carbazoles | | Synth. Met. 111, 421 (2000) |
| Isoindole compounds | | Chem. Mater. 15, 3148 (2003) |
| Metal carbene complexes | | US20080018221 |

Phosphorescent OLED host materials
Red hosts

| | | |
| --- | --- | --- |
| Arylcarbazoles | | Appl. Phys. Lett. 78, 1622 (2001) |

TABLE 3-continued
| MATERIAL | EXAMPLES OF MATERIAL | PUBLICATIONS |
|---|---|---|
| Metal 8-hydroxy-quinolates (e.g., Alq$_3$, BAlq) | 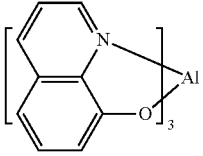 | Nature 395, 151 (1998) |
| | 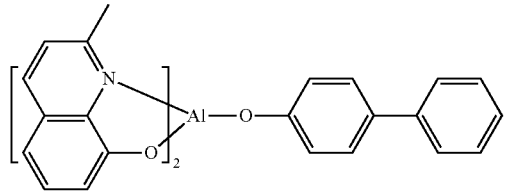 | US20060202194 |
| | 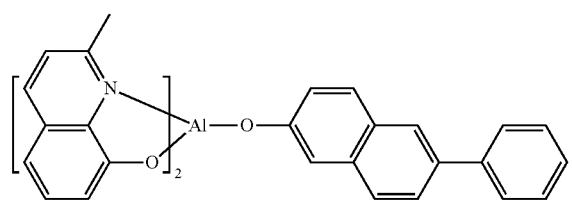 | WO2005014551 |
| | 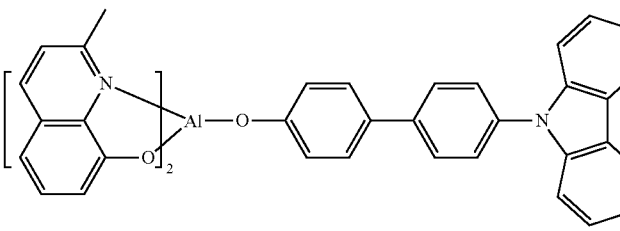 | WO2006072002 |
| Metal phenoxy-benzothiazole compounds | 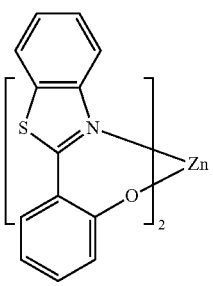 | Appl. Phys. Lett. 90, 123509 (2007) |
| Conjugated oligomers and polymers (e.g., poly-fluorene) | 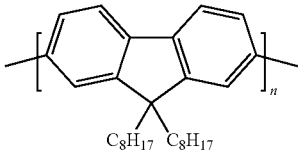 | Org. Electron. 1, 15 (2000) |
| Aromatic fused rings | 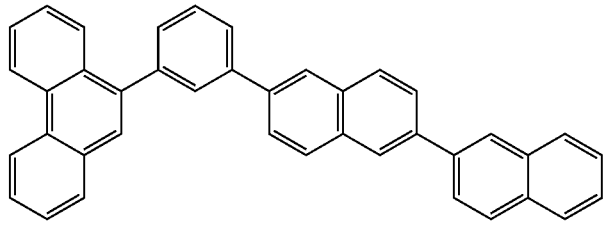 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |

TABLE 3-continued

| MATERIAL | EXAMPLES OF MATERIAL | PUBLICATIONS |
|---|---|---|
| Zinc complexes | | WO2009062578 |
| Green hosts | | |
| Arylcarbazoles | | Appl. Phys. Lett. 78, 1622 (2001) |
| | | US20030175553 |
| | | WO2001039234 |
| Aryltriphenylene compounds | | US20060280965 |

TABLE 3-continued
| MATERIAL | EXAMPLES OF MATERIAL | PUBLICATIONS |
|---|---|---|
| | 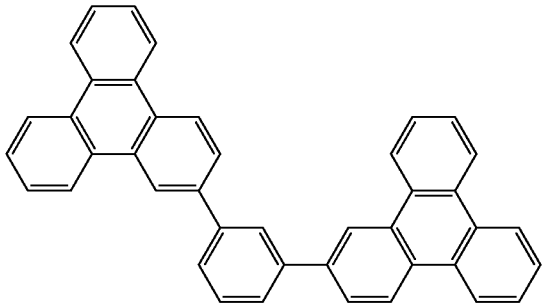 [SMILES: c1cc(-c2ccc3c4ccccc4c4ccccc4c3c2)cc(-c2ccc3c4ccccc4c4ccccc4c3c2)c1] | US20060280965 |
| | 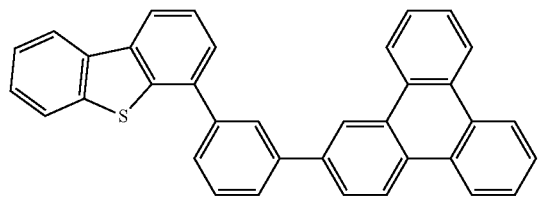 [SMILES: c1cc(-c2ccc3c4ccccc4c4ccccc4c3c2)cc(-c2cccc3c2sc2ccccc23)c1] | WO2009021126 |
| Donor acceptor type molecules | 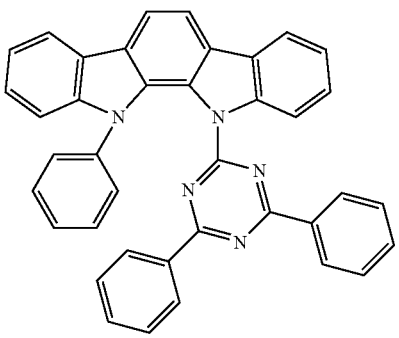 [SMILES: c1ccc(-c2nc(-c3ccccc3)nc(-n3c4ccccc4c4ccc5c6ccccc6n(-c6ccccc6)c5c43)n2)cc1] | WO2008056746 |
| Aza-carbazole/ DBT/DBF | 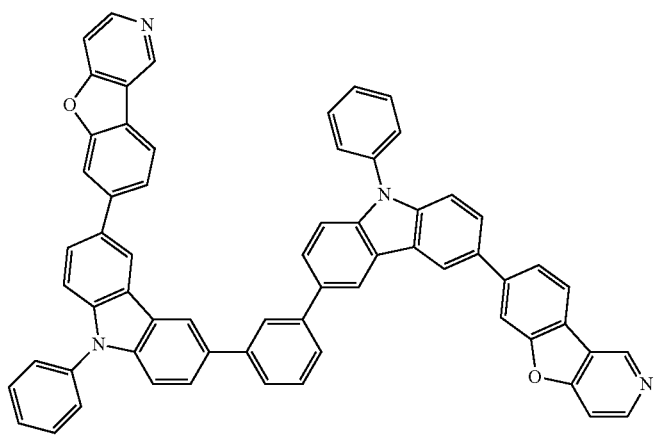 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| Polymers (e.g., PVK) | 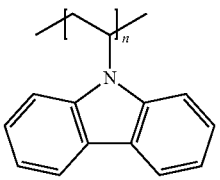 | Appl. Phys. Lett. 77, 2280 (2000) |

TABLE 3-continued
| MATERIAL | EXAMPLES OF MATERIAL | PUBLICATIONS |
|---|---|---|
| Spirofluorene compounds | 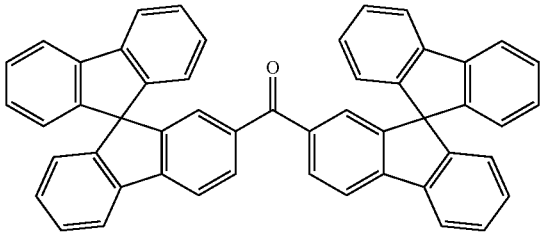 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxy-benzooxazole compounds | 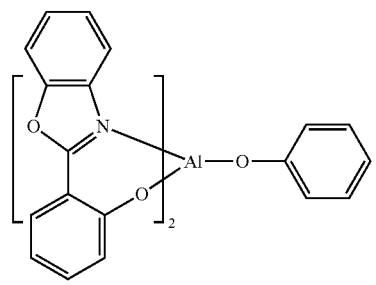 | WO2005089025 |
| | 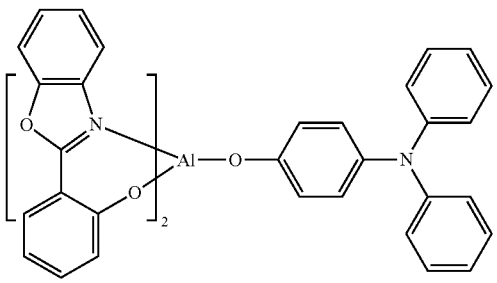 | WO2006132173 |
| | 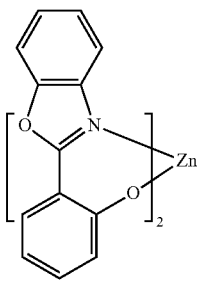 | JP200511610 |
| Spirofluorene-carbazole compounds | 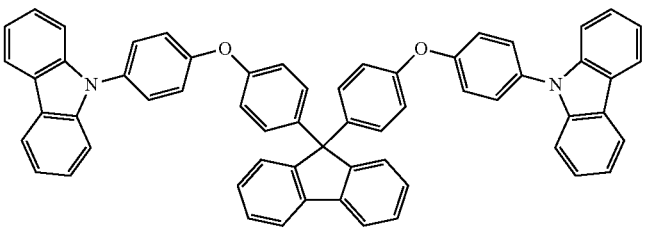 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |

TABLE 3-continued
| MATERIAL | EXAMPLES OF MATERIAL | PUBLICATIONS |
|---|---|---|
| | 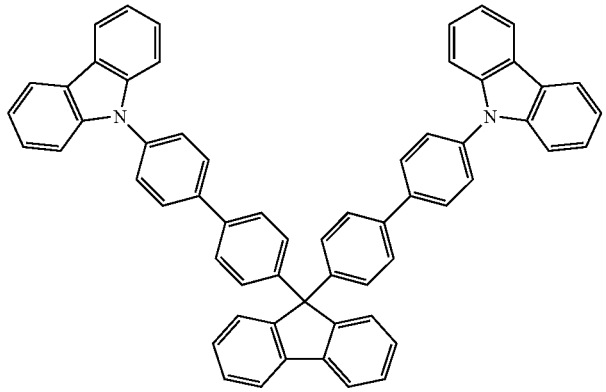 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocabazoles | 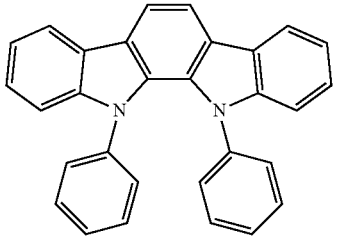 [SMILES: c1ccc(-n2c3ccccc3c3ccc4c5ccccc5n(-c5ccccc5)c4c32)cc1] | WO2007063796 |
| | 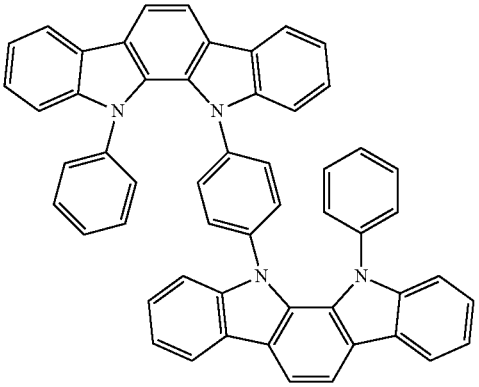 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 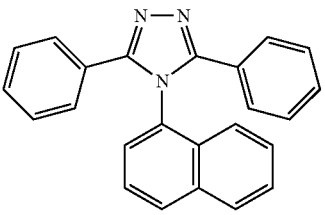 [SMILES: c1ccc(-c2nnc(-c3ccccc3)n2-c2cccc3ccccc23)cc1] | J. Appl. Phys. 90, 5048 (2001) |
| | 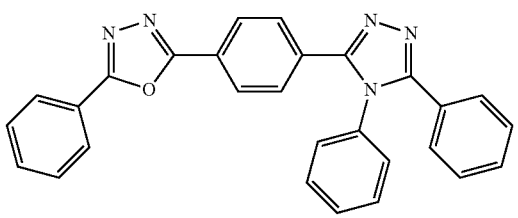 [SMILES: c1ccc(-c2nnc(-c3ccc(-c4nnc(-c5ccccc5)n4-c4ccccc4)cc3)o2)cc1] | WO2004107822 |

TABLE 3-continued
| MATERIAL | EXAMPLES OF MATERIAL | PUBLICATIONS |
|---|---|---|
| Tetraphenylene complexes | 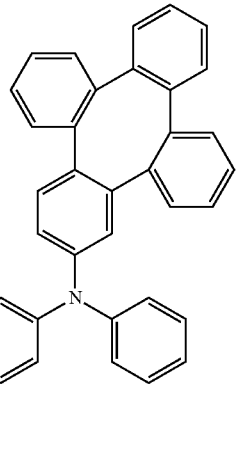 | US20050112407 |
| Metal phenoxy-pyridine compounds | 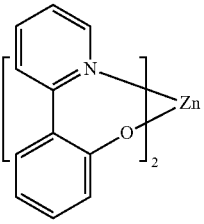 | WO2005030900 |
| Metal coordination complexes (e.g., Zn, Al with N^N ligands) | 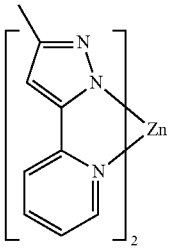 | US20040137268, US20040137267 |
Blue hosts
| | | |
|---|---|---|
| Arylcarbazoles | 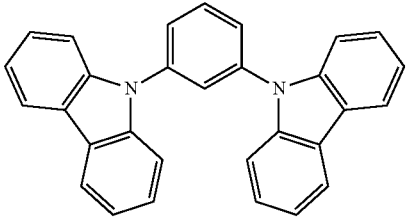 [SMILES: c1cc(-n2c3ccccc3c3ccccc32)cc(-n2c3ccccc3c3ccccc32)c1] | Appl. Phys. Lett, 82, 2422 (2003) |
| | 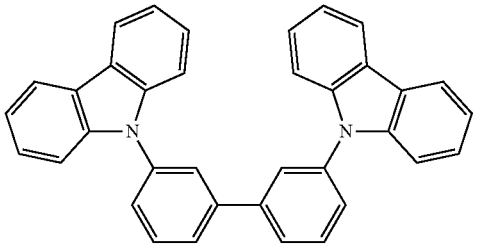 [SMILES: c1cc(-c2cccc(-n3c4ccccc4c4ccccc43)c2)cc(-n2c3ccccc3c3ccccc32)c1] | US20070190359 |

TABLE 3-continued
| MATERIAL | EXAMPLES OF MATERIAL | PUBLICATIONS |
|---|---|---|
| Dibenzothiophene/Dibenzofuran-carbazole compounds | 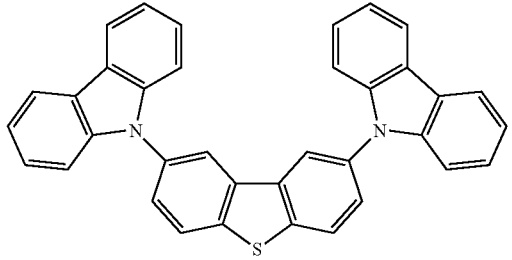 [SMILES: c1ccc2c(c1)c1ccccc1n2-c1ccc2sc3ccc(-n4c5ccccc5c5ccccc54)cc3c2c1] | WO2006114966, US20090167162 |
| | 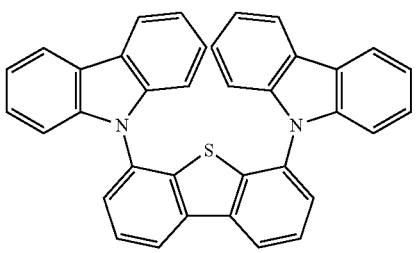 [SMILES: c1cc(-n2c3ccccc3c3ccccc32)c2sc3c(-n4c5ccccc5c5ccccc54)cccc3c2c1] | US20090167162 |
| | 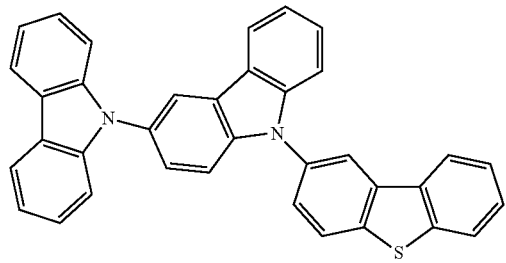 [SMILES: c1ccc2c(c1)sc1ccc(-n3c4ccccc4c4cc(-n5c6ccccc6c6ccccc65)ccc43)cc12] | WO2009086028 |
| | 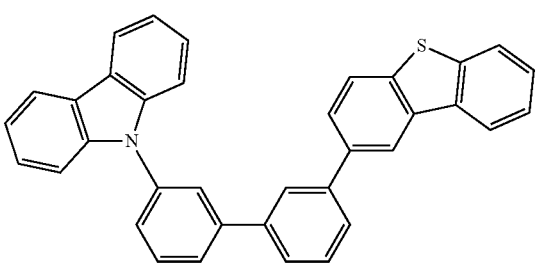 | US20090030202, US20090017330 |
| Silicon aryl compounds | 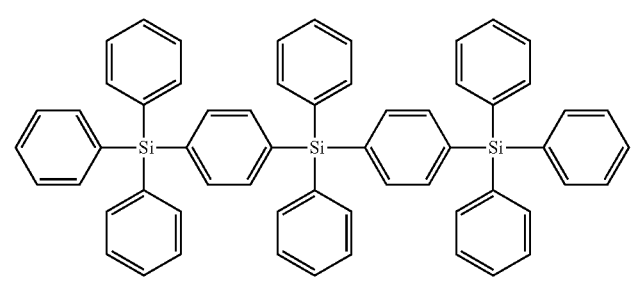 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 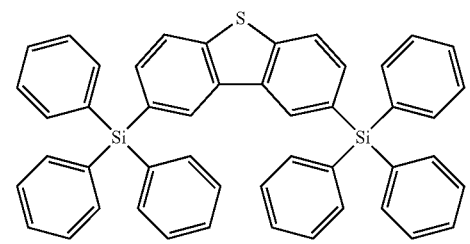 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 3-continued
| MATERIAL | EXAMPLES OF MATERIAL | PUBLICATIONS |
|---|---|---|
| Silicon/Germanium aryl compounds | 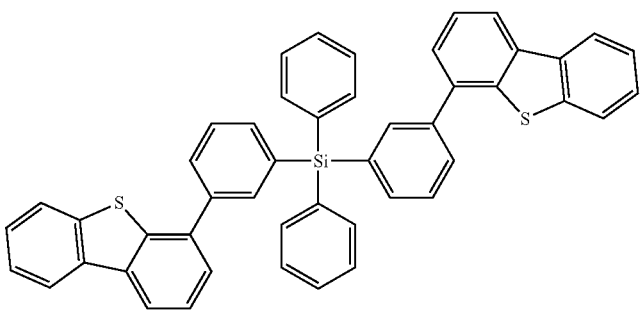 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 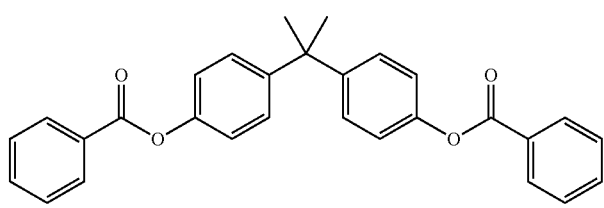 [SMILES: CC(C)(c1ccc(OC(=O)c2ccccc2)cc1)c1ccc(OC(=O)c2ccccc2)cc1] | WO2006100298 |
| High triplet metal organometallic complex | 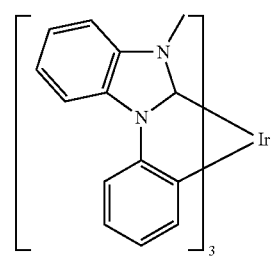 | U.S. Pat. No. 7,154,114 |
Phosphorescent dopants
Red dopants
| | | |
|---|---|---|
| Heavy metal porphyrins (e.g., PtOEP) | 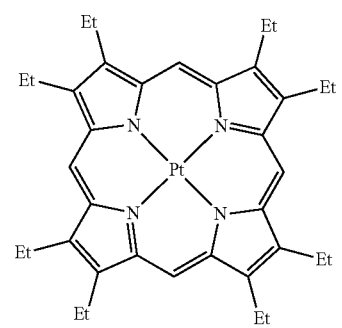 | Nature 395, 151 (1998) |
| Iridium (III) organometallic complexes | 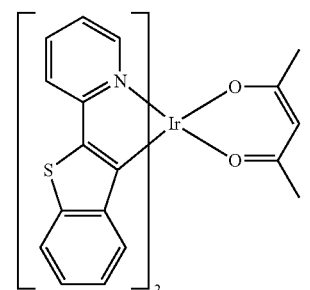 | Appl. Phys. Lett. 78, 1622 (2001) |

TABLE 3-continued

| MATERIAL | EXAMPLES OF MATERIAL | PUBLICATIONS |
|---|---|---|
| | | US2006835469 |
| | | US2006835469 |
| | | US20060202194 |
| | | US20060202194 |
| | | US20070087321 |

| MATERIAL | EXAMPLES OF MATERIAL | PUBLICATIONS |
|---|---|---|
| | | US20070087321 |
| | | Adv. Mater. 19, 739 (2007) |
| | | WO2009100991 |
| | | WO2008101842 |
| Platinum (II) organometallic complexes | | WO2003040257 |

TABLE 3-continued
| MATERIAL | EXAMPLES OF MATERIAL | PUBLICATIONS |
| --- | --- | --- |
| Osminum (III) complexes | 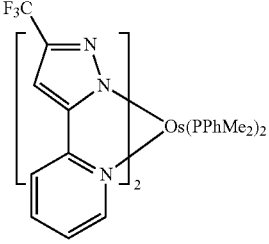 | Chem. Mater. 17, 3532 (2005) |
| Ruthenium (II) complexes | 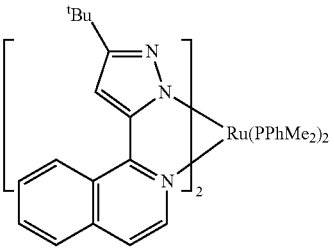 | Adv. Mater. 17, 1059 (2005) |
| Rhenium (I), (II), and (III) complexes | 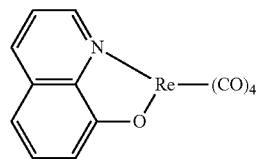 | US20050244673 |
Green dopants
| | | |
| --- | --- | --- |
| Iridium (III) organometallic complexes | 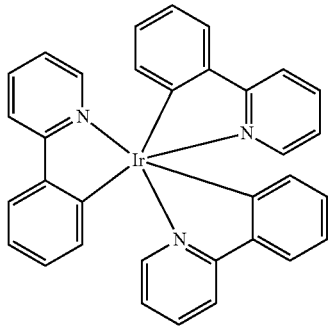
and its derivatives | Inorg. Chem. 40, 1704 (2001) |
| | 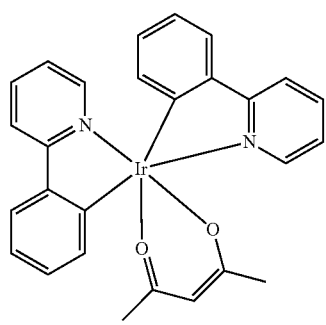 | US20020034656 |

TABLE 3-continued
| MATERIAL | EXAMPLES OF MATERIAL | PUBLICATIONS |
|---|---|---|
| | 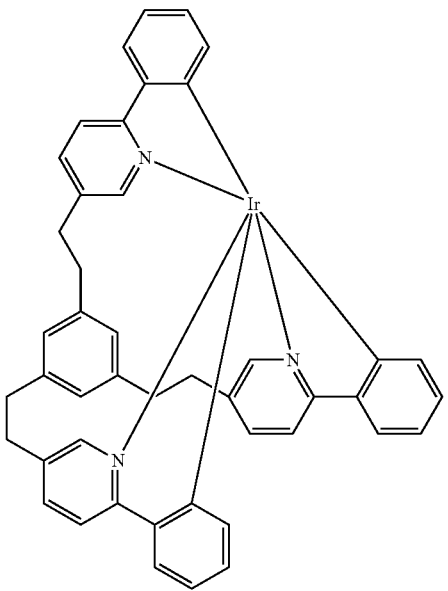 | U.S. Pat. No. 7,332,232 |
| | 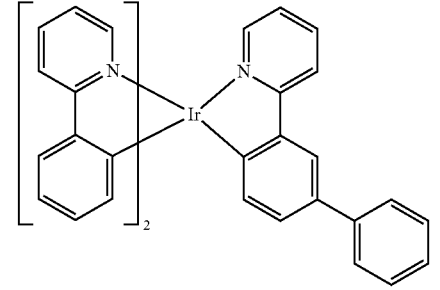 | US20090108737 |
| | 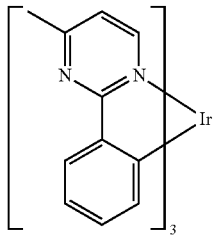 | US20090039776 |
| | 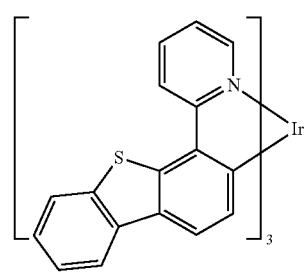 | U.S. Pat. No. 6,921,915 |

TABLE 3-continued

| MATERIAL | EXAMPLES OF MATERIAL | PUBLICATIONS |
| --- | --- | --- |
| | | U.S. Pat. No. 6,687,266 |
| | | Chem. Mater. 16, 2480 (2004) |
| | | US20070190359 |
| | | US 20060008670 JP2007123392 |
| | | Adv. Mater. 16, 2003 (2004) |

TABLE 3-continued

| MATERIAL | EXAMPLES OF MATERIAL | PUBLICATIONS |
|---|---|---|
| | | Angew. Chem. Int. Ed. 2006, 45, 7800 |
| | | WO2009050290 |
| | | US20090165846 |
| | | US20080015355 |
| Monomer for polymeric metal organometallic compounds | | U.S. Pat. No. 7,250,226, U.S. Pat. No. 7,396,598 |

TABLE 3-continued

| MATERIAL | EXAMPLES OF MATERIAL | PUBLICATIONS |
|---|---|---|
| Pt (II) organo-metallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |
| | | US20060263635 |

TABLE 3-continued

| MATERIAL | EXAMPLES OF MATERIAL | PUBLICATIONS |
| --- | --- | --- |
| Cu complexes | | WO2009000673 |
| Gold complexes | | Chem. Commun. 2906 (2005) |
| Rhenium (III) complexes | | Inorg. Chem. 42, 1248 (2003) |
| Deuterated organometallic complexes | | US20030138657 |

TABLE 3-continued
| MATERIAL | EXAMPLES OF MATERIAL | PUBLICATIONS |
|---|---|---|
| Organometallic complexes with two or more metal centers | 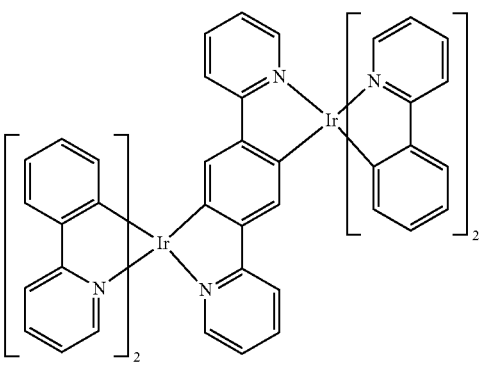 | US20030152802 |
| | 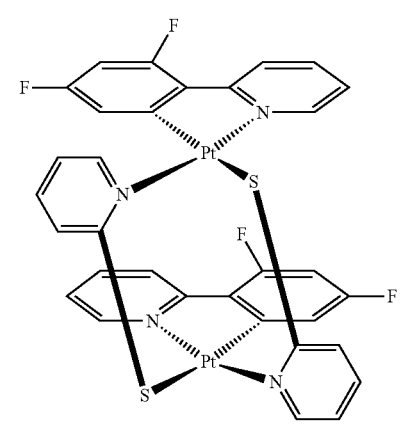 | U.S. Pat. No. 7,090,928 |
Blue dopants
| | | |
|---|---|---|
| Iridium (III) organometallic complexes | 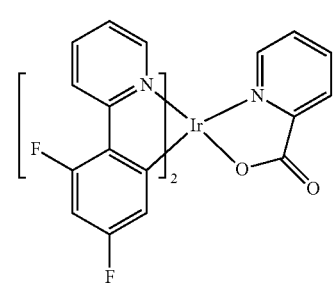 | WO2002002714 |
| | 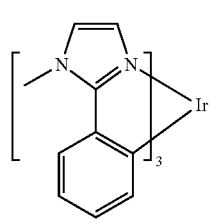 | WO2006009024 |
| | 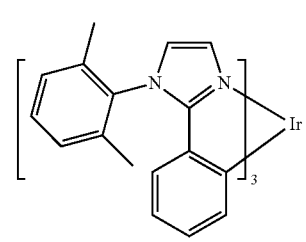 | US20060251923 |

TABLE 3-continued
| MATERIAL | EXAMPLES OF MATERIAL | PUBLICATIONS |
|---|---|---|
| | 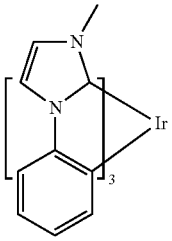 | U.S. Pat. No. 7,393,599, WO2006056418, US20050260441, WO2005019373 |
| | 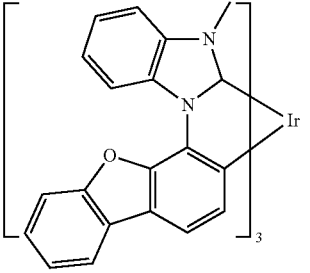 | U.S. Pat. No. 7,534,505 |
| | 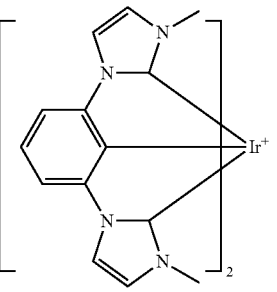 | U.S. Pat. No. 7,445,855 |
| | 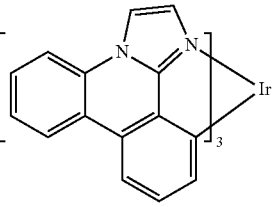 | US20070190359, US20080297033 |
| | 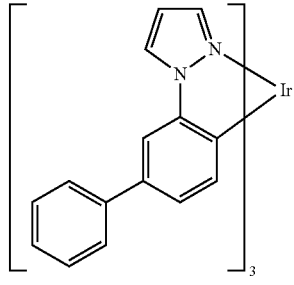 | U.S. Pat. No. 7,338,722 |
| | 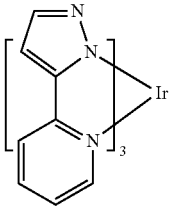 | US20020134984 |

TABLE 3-continued

| MATERIAL | EXAMPLES OF MATERIAL | PUBLICATIONS |
|---|---|---|
| | | Angew. Chem. Int. Ed. 47, 1 (2008) |
| | | Chem. Mater. 18, 5119 (2006) |
| | | Inorg. Chem. 46, 4308 (2007) |
| | | WO2005123873 |
| | | WO2005123873 |
| | | WO2007004380 |

TABLE 3-continued

| MATERIAL | EXAMPLES OF MATERIAL | PUBLICATIONS |
|---|---|---|
| | | WO2006082742 |
| Osmium (II) complexes | | U.S. Pat. No. 7,279,704 |
| | | Organometallics 23, 3745 (2004) |
| Gold complexes | | Appl. Phys. Lett. 74, 1361 (1999) |
| Platinum (II) complexes | | WO2006098120, WO2006103874 |

Exciton/hole blocking layer materials

TABLE 3-continued
| MATERIAL | EXAMPLES OF MATERIAL | PUBLICATIONS |
|---|---|---|
| Bathocuprine compounds (e.g., BCP, BPhen) | 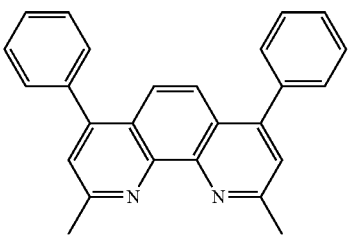 [SMILES: Cc1cc(-c2ccccc2)c2ccc3c(-c4ccccc4)cc(C)nc3c2n1] | Appl. Phys. Lett. 75, 4 (1999) |
| | 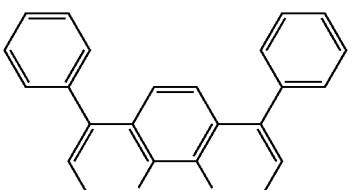 | Appl. Phys. Lett. 79, 449 (2001) |
| Metal 8-hydroxy-quinolates (e.g., BAlq) | 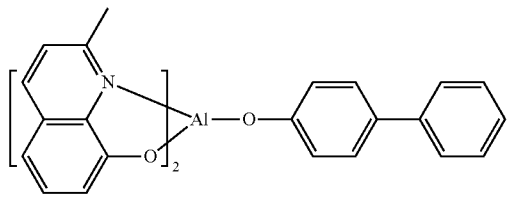 | Appl. Phys. Lett. 81, 162 (2002) |
| 5-member ring electron deficient heterocycles such as triazole, oxadiazole, imidazole, benzoimidazole | 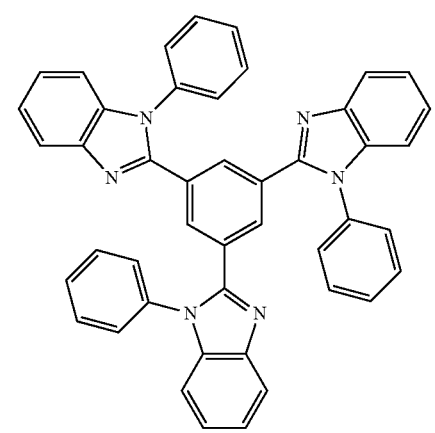 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 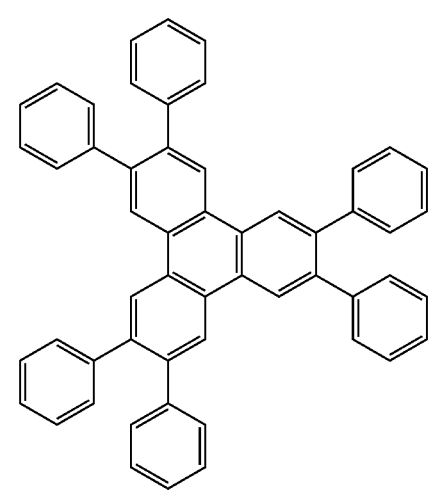 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

| MATERIAL | EXAMPLES OF MATERIAL | PUBLICATIONS |
|---|---|---|
| Fluorinated aromatic compounds | 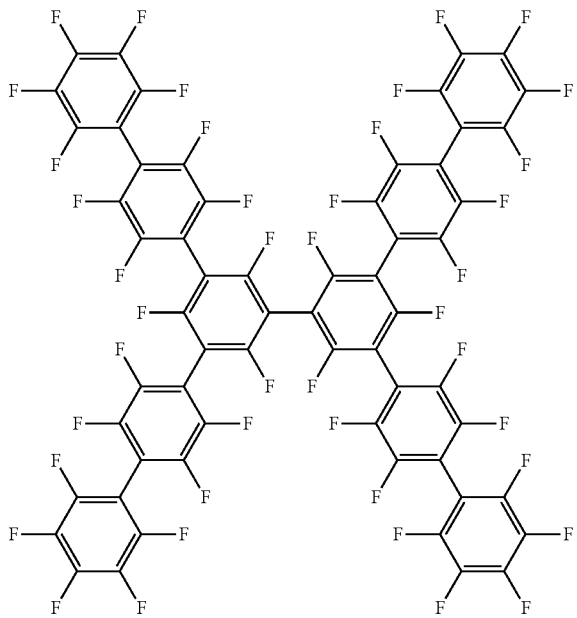 [SMILES: Fc1c(F)c(F)c(-c2c(F)c(F)c(-c3c(F)c(-c4c(F)c(F)c(-c5c(F)c(F)c(F)c(F)c5F)c(F)c4F)c(F)c(-c4c(F)c(-c5c(F)c(F)c(-c6c(F)c(F)c(F)c(F)c6F)c(F)c5F)c(F)c(-c5c(F)c(F)c(-c6c(F)c(F)c(F)c(F)c6F)c(F)c5F)c4F)c3F)c(F)c2F)c(F)c1F] | Appl. Phys. Lett. 79, 156 (2001) |
| Phenothiazine-S-oxide | 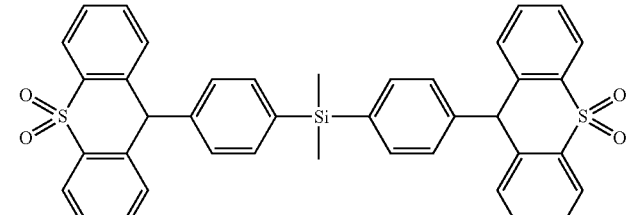 | WO2008132085 |
Electron transporting materials
| | | |
|---|---|---|
| Anthracene-benzoimidazole compounds | 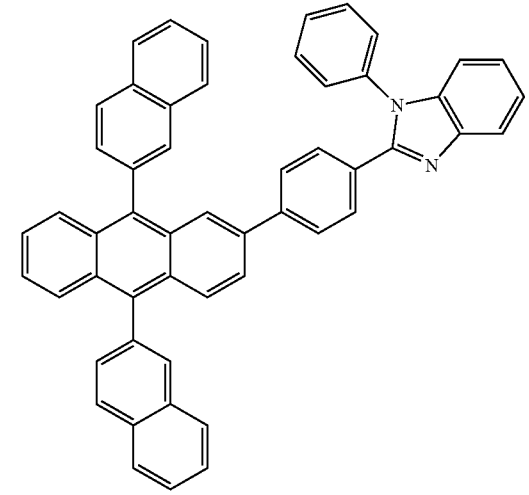 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |

TABLE 3-continued

| MATERIAL | EXAMPLES OF MATERIAL | PUBLICATIONS |
| --- | --- | --- |
| | | US20090179554 |
| Aza triphenylene derivatives | | US20090115316 |
| Anthracene-benzothiazole compounds | | Appl. Phys. Lett. 89, 063504 (2006) |
| Metal 8-hydroxy-quinolates (e.g., Alq$_3$, Zrq$_4$) | | Appl. Phys. Lett. 51, 913 (1987) U.S. Pat. No. 7,230,107 |
| Metal hydroxy-benoquinolates | | Chem. Lett. 5, 905 (1993) |
| Bathocuprine compounds such as BCP, BPhen, etc | | Appl. Phys. Lett. 91, 263503 (2007) |

TABLE 3-continued
| MATERIAL | EXAMPLES OF MATERIAL | PUBLICATIONS |
|---|---|---|
| | 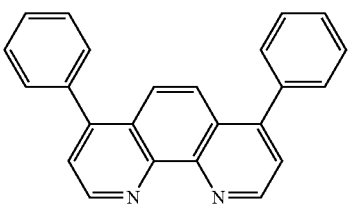 [SMILES: c1ccc(-c2ccnc3c2ccc2c(-c4ccccc4)ccnc23)cc1] | Appl. Phys. Lett. 79, 449 (2001) |
| 5-member ring electron deficient heterocycles (e.g.,triazole, oxadiazole, imidazole, benzoimidazole) | 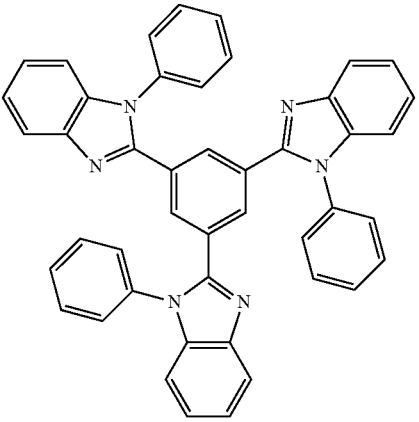 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 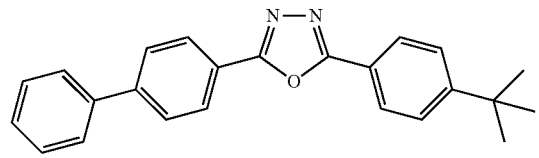 [SMILES: CC(C)(C)c1ccc(-c2nnc(-c3ccc(-c4ccccc4)cc3)o2)cc1] | Appl. Phys. Lett. 55, 1489 (1989) |
| | 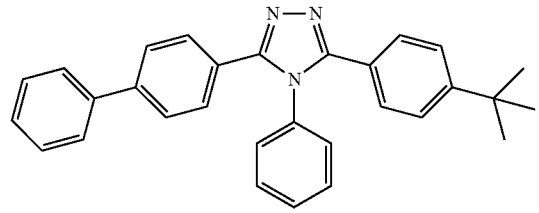 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 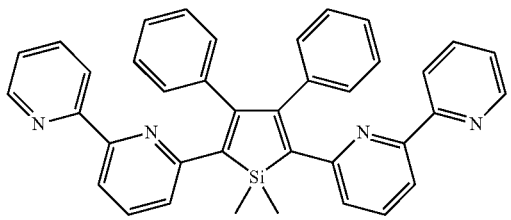 [SMILES: C[Si]1(C)C(c2cccc(-c3ccccn3)n2)=C(c2ccccc2)C(c2ccccc2)=C1c1cccc(-c2ccccn2)n1] | Org. Electron, 4, 113 (2003) |
| Arylborane compounds | 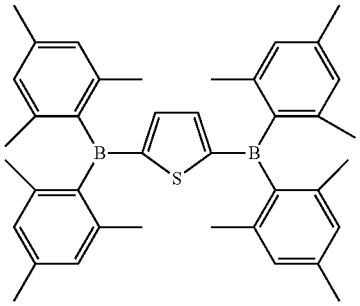 | J. Am. Chem. Soc. 120, 9714 (1998) |

TABLE 3-continued

| MATERIAL | EXAMPLES OF MATERIAL | PUBLICATIONS |
| --- | --- | --- |
| Fluorinated aromatic compounds | | J. Am. Chem. Soc. 122, 1832 (2000) |
| Fullerene (e.g., C60) | | US20090101870 |
| Triazine complexes | | US20040036077 |
| Zn (N^N) complexes | | U.S. Pat. No. 6,528,187 |

EXPERIMENTAL

Chemical abbreviations used throughout this document are as follows: Cy is cyclohexyl, dba is dibenzylideneacetone, EtOAc is ethyl acetate.

Example 1

Synthesis of Condensation Product of Benzaldehyde and N-(2,6-diisopropylphenyl)benzene-1,2-diamine

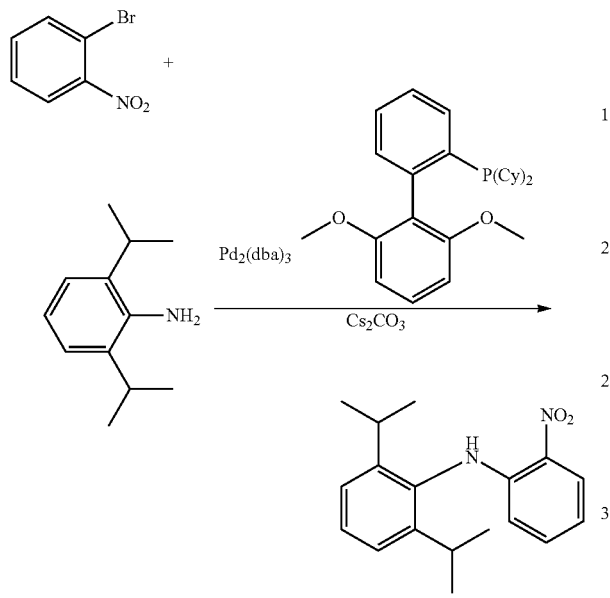

1-Bromo-2-nitrobenzene (15 g, 75 mmol), 2,6-diisopropylaniline (14.0 mL, 75 mmol) and cesium carbonate (41.5 g, 127 mmol) were mixed in 500 mL of toluene and the solution was bubbled with nitrogen for 20 min. Pd$_2$(dba)$_3$ (1.36 g, 1.49 mmol) and dicyclohexyl(2',6'-dimethoxy-[1,1'-biphenyl]-2-yl)phosphine (2.44 g, 5.94 mmol) were added and reaction mixture was heated to reflux for 18 h. After cooling, the organic layer separated and the aqueous layer was extracted with 3×50 mL dichloromethane and dried over sodium sulfate. After removing the solvent under reduced pressure, the crude product was chromatographed on silica gel with 10:90 (v/v) ethyl acetate:hexane and 20 g (72%) of the product was obtained. The product was confirmed by GC/MS, NMR and HPLC (99.96% pure)

2,6-Diisopropyl-N-(2-nitrophenyl) aniline (12 g, 40.2 mmol) was dissolved in 200 mL ethanol and palladium on carbon (0.642 g) was added. The reaction mixture was placed on the Parr hydrogenator for 1 h. The reaction mixture was filtered through a Celite® plug, washed with dichloromethane and evaporated. The crude product was chromatographed on silica gel with 10:90 (v/v) ethyl acetate:hexane and 10 g (93%) of the product was obtained. The product was confirmed by GC/MS and NMR.

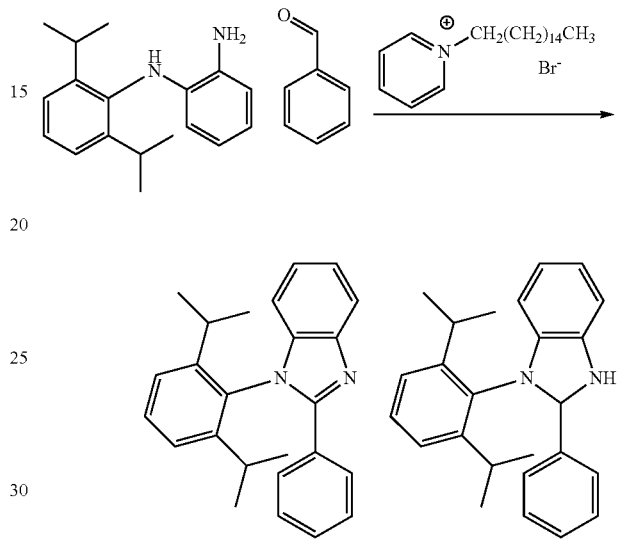

N-(2,6-Diisopropylphenyl)benzene-1,2-diamine (16.5 g, 61.5 mmol), benzaldehyde (9.8 mL, 92 mmol) and 1-hexadecylpyridinium bromide (1.2 g, 3.1 mmol) were dissolved in 50 mL THF and 500 mL water and stirred at room temperature overnight. By GC/MS the reaction mixture typically showed a mixture of the phenylbenzimidazole product and the phenyl-2,3-dihydro-1H-benzo[d]imidazole product (ca. 50:50). Brine (200 mL) was added and the reaction mixture extracted with EtOAc (3×300 mL), dried over sodium sulfate and evaporated. The total crude yield was 20 g (~91%) and was carried onto the next step.

Example 2

Reaction of Condensation Product of Benzaldehyde and N-(2,6-diisopropylphenyl)benzene-1,2-diamine with Manganese (IV) Oxide

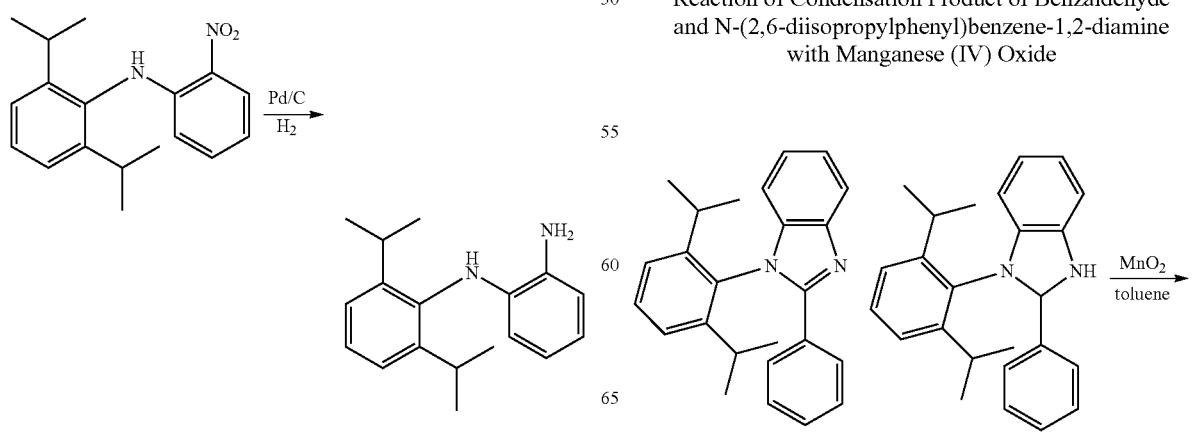

-continued

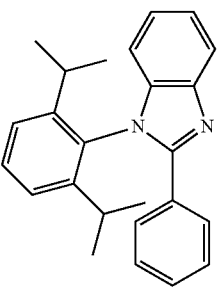

The mixture of the phenylbenzimidazole product and the phenyl-2,3-dihydro-1H-benzo[d]imidazole product (18 g, 50.5 mmol) obtained as in Example 1 was combined and manganese(IV) oxide (22 g, 252 mmol) in 300 mL of toluene. With vigorous stirring, the reaction was heated to reflux for 10 h, cooled, filtered through a plug of silica gel eluted with dichloromethane and evaporated. The crude product was chromatographed on silica gel with 0-3% ethyl acetate in dichloromethane and then recrystallized from hexane to give 14.7 g (82%) of the product. The product was confirmed by HPLC (>98%) and NMR. Yields ranged from 48-75%.

Example 3

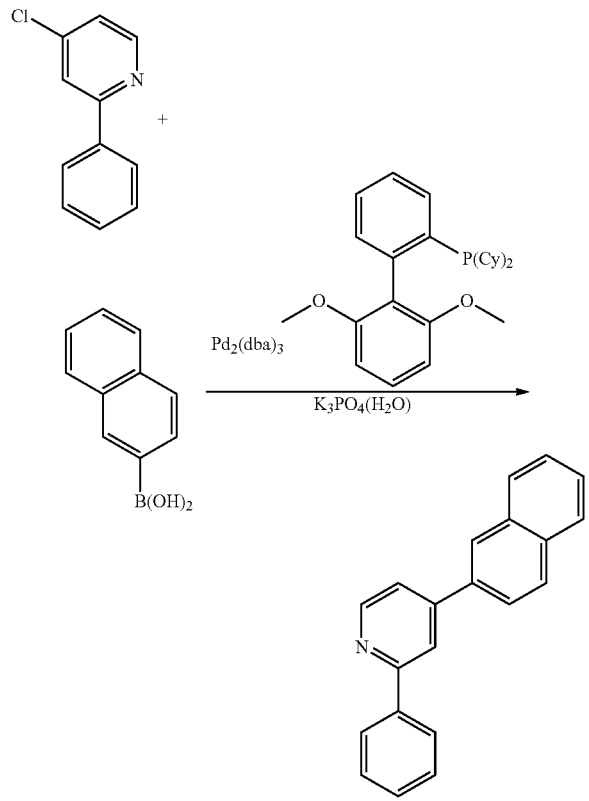

To a 1 L round bottom flask was added 4-chloro-2-phenylpyridine (3.31 g, 17.44 mmol), naphthalen-2-ylboronic acid (3.0 g, 17.44 mmol), dicyclohexyl(2',6'-dimethoxy-[1,1'-biphenyl]-2-yl)phosphine (0.286 g, 0.698 mmol) and potassium phosphate tribasic monohydrate (12.1 g, 52.3 mmol) with toluene 250 mL and water 25 mL. The reaction mixture was degassed with $N_2$ for 20 minutes. $Pd_2(dba)_3$ (0.319 g, 0.349 mmol) was added and the reaction mixture was refluxed for 18 h. After cooling, the aqueous layer was removed and toluene was evaporated under reduced pressure. The residue was dissolved in dichloromethane and passed through one inch silica gel plug on a fit, eluting with dichloromethane. The crude product was chromatographed on silica gel with 20-25% ethyl acetate in hexane to give 3 g (61%) of the product. The product was confirmed by HPLC (100% purity) and GC/MS.

Example 4

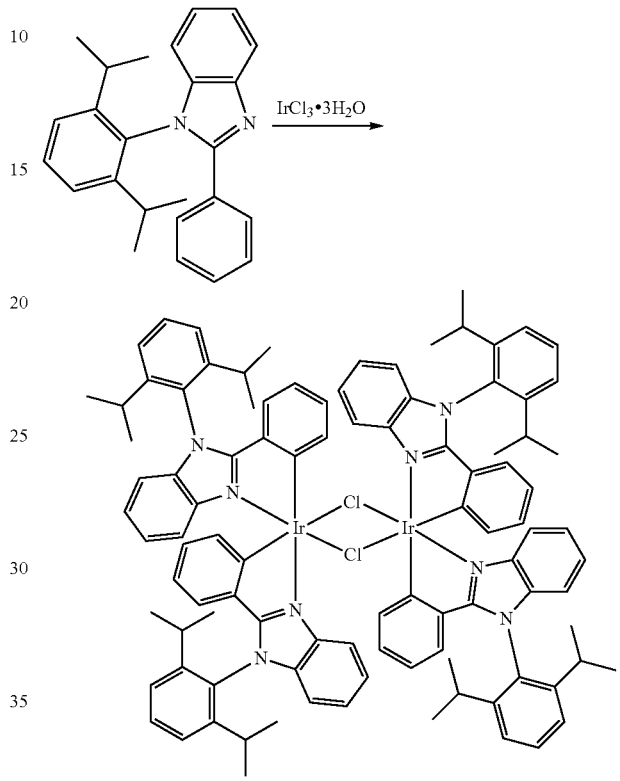

To a round-bottom flask was added 1-(2,6-diisopropylcyclohexa-2,4-dien-1-yl)-2-phenyl-1H-benzo[d]imidazole (6.0 g, 16.83 mmol) and iridium (III) chloride hydrate (1.98 g, 5.61 mmol) with 2-ethoxyethanol (100 mL) and water (33 mL) under $N_2$ atmosphere. The resulting reaction mixture was refluxed at 130° C. for 18 h. The yellow precipitate was filtered, washed with methanol (3-4 times) and hexane (3-4 times) to yield 5.2 g (98.8%) of a yellow solid after drying. The product was used without further purification.

Example 5

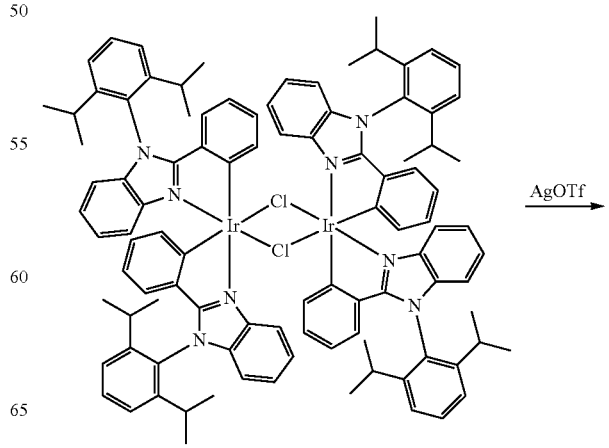

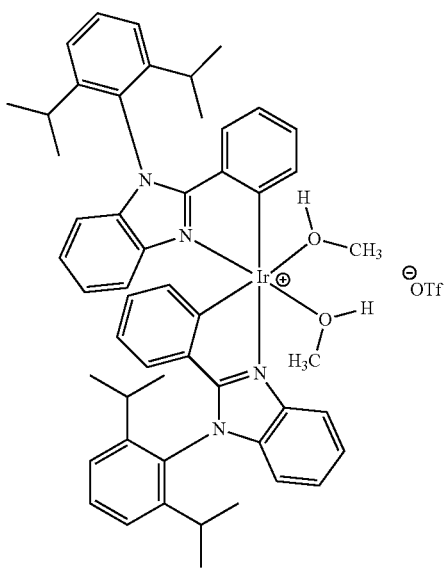

In a round-bottom flask, the iridium dimer complex obtained as in Example 4 (5.2 g, 2.78 mmol) was dissolved in 200 mL dichloromethane. In a separate flask, silver(I) triflate (1.5 g, 5.84 mmol) was dissolved in 250 mL of MeOH. This was added slowly to the dimer solution with continuous stirring at room temperature. The reaction mixture was stirred overnight in the dark, then filtered through a tightly packed Celite® bed to remove silver chloride precipitate. The solvent was removed under reduced pressure to give 6.0 g (100%) of a brownish green solid and used without further purification.

Example 6

Synthesis of Compound 58

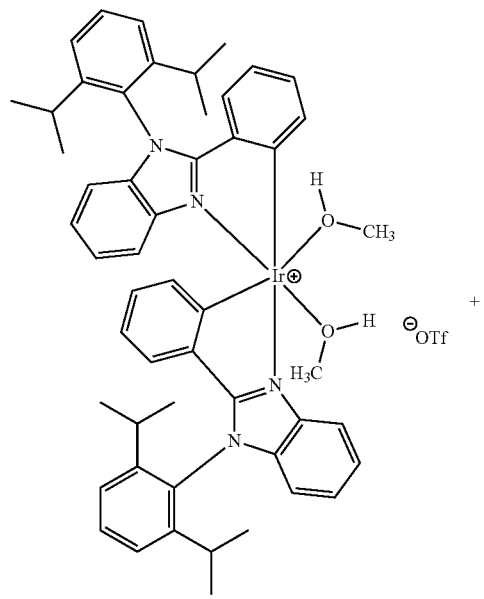

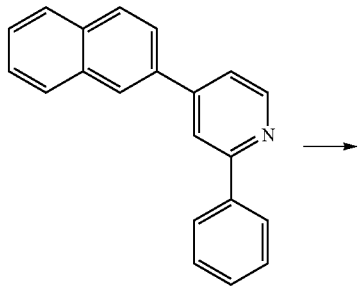

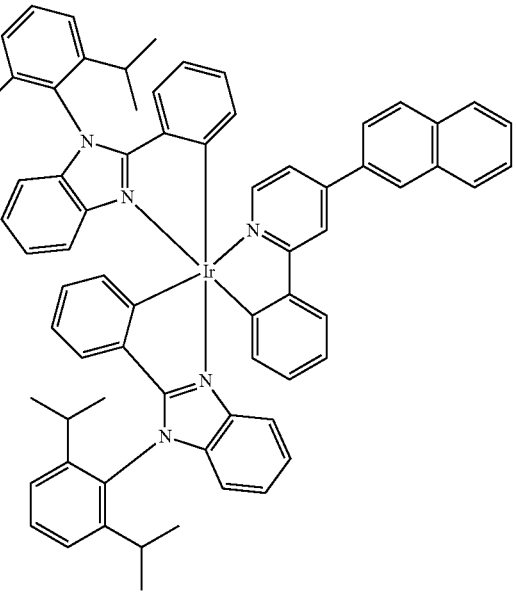

To a flask was added the iridium triflate complex obtained as in Example 5 (3.0 g, 2.7 mmol) and 4-(naphthalen-2-yl)-2-phenylpyridine (3.0 g, 10.7 mmol) obtained as in Example 3, 25 mL EtOH and 25 mL MeOH. The reaction mixture was refluxed for 18 h, with a yellow-orange precipitate forming. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The celite/silica plug was then washed with dichloromethane to dissolve the product. Half the volume of dichloromethane was removed under reduced pressure and isopropanol was added to precipitate the product, which was filtered and washed with methanol and hexane. The crude product was chromatographed on silica gel with 1/1 (v/v) dichloromethane/hexane and then sublimed to yield 1.4 g (44%) of product as a yellow solid. The product, Compound 58, was confirmed by HPLC (99.8% pure) and LC/MS.

Example 7

Synthesis of Compound 30

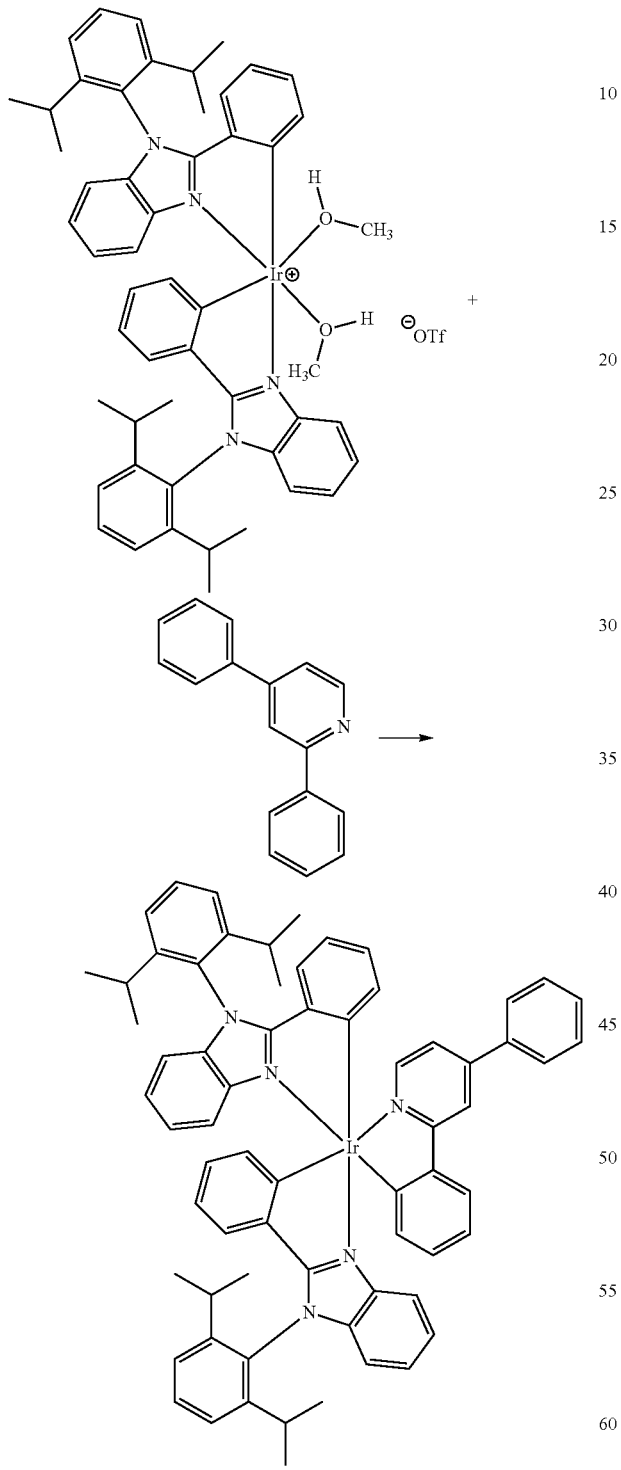

To a flask was added the iridium triflate complex (3.5 g, 3.2 mmol) and 2,4-diphenylpyridine (3.5 g, 15.13 mmol), 25 mL EtOH and 25 mL MeOH. The reaction mixture was refluxed for 18 h, with a yellow-orange precipitate forming. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The celite/silica plug was then washed with dichloromethane to dissolve the product. Half the volume of dichloromethane was removed under reduced pressure and isopropanol was added to precipitate the product, which was filtered and washed with methanol and hexane. The crude product was chromatographed on silica gel with 1/1 (v/v) dichloromethane/hexane and then sublimed to yield 1.9 g (54%) of product as a yellow solid. The product, Compound 30, was confirmed by HPLC (99.9% pure) and LC/MS.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A compound comprising a heteroleptic iridium complex having the formula:

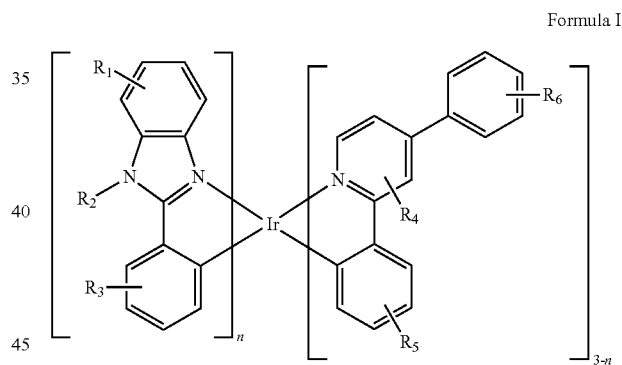

Formula I wherein $R_1$, $R_3$, $R_4$, $R_5$, and $R_6$ represent mono-, di-, tri- or tetra-substitution;

wherein $R_1$, $R_2$, $R_3$, $R_4$, $R_5$, and $R_6$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein $R_1$, $R_3$, $R_4$, $R_5$, and $R_6$ are optionally fused and may be further substituted;

wherein (1) $R_6$ is alkyl or heteroalkyl at a position para to a pyridine bonded to iridium, or (2) $R_6$ is fused and, optionally, further substituted, or (3) both conditions (1) and (2) are satisfied; and wherein n=1 or 2.

2. The compound of claim 1, wherein n=2.

3. The compound of claim 1, wherein n=1.

4. The compound of claim 1, wherein $R_2$ is aryl or substituted aryl.

5. The compound of claim 4, wherein $R_2$ is a 2,6-disubstituted aryl.

6. The compound of claim 5, wherein $R_2$ is

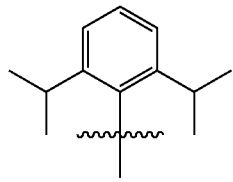

7. The compound of claim 1, wherein $R_2$ is alkyl.

8. The compound of claim 1, wherein $R_3$, $R_4$, $R_5$ and $R_6$ are each independently selected from the group consisting of hydrogen and alkyl, and wherein at least one of $R_3$, $R_4$, $R_5$ and $R_6$ is alkyl.

9. The compound of claim 1, wherein $R_5$ is aryl.

10. The compound of claim 1, wherein $R_6$ is fused to form a naphthyl or aza-naphthyl ring system.

11. The compound of claim 1, wherein $R_1$, $R_3$, and $R_5$ are hydrogen.

12. The compound of claim 1, wherein the compound is selected from the group consisting of:

Compound 3

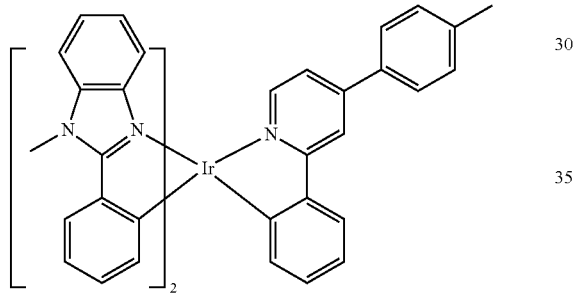

Compound 4

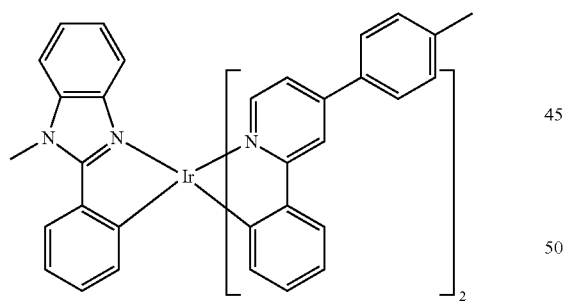

Compound 5

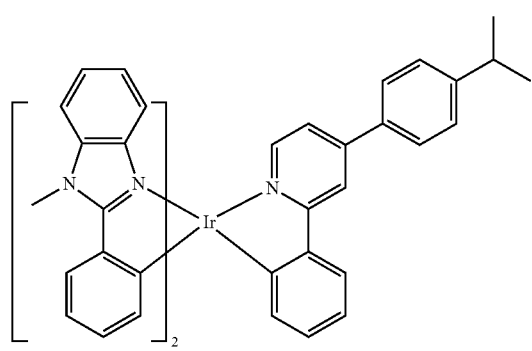

-continued

Compound 6

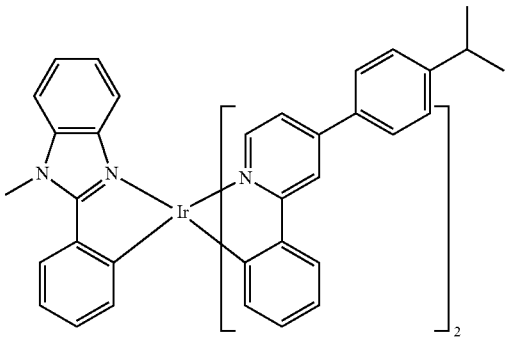

Compound 9

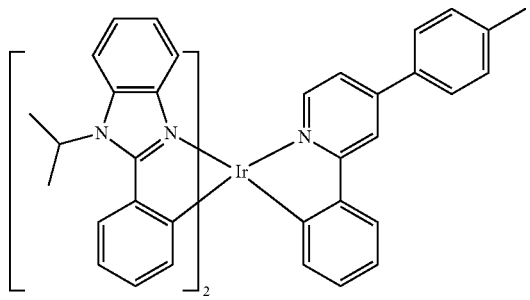

Compound 10

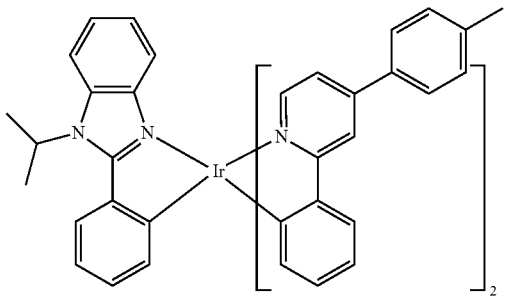

Compound 11

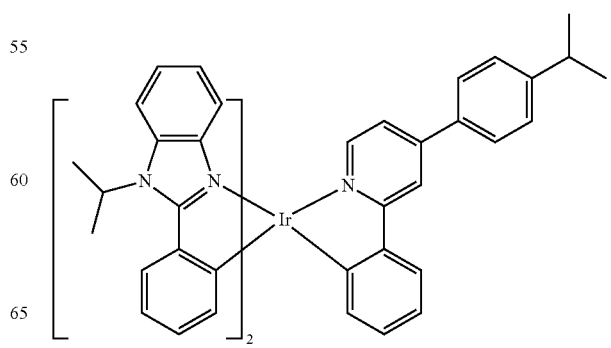

Compound 12
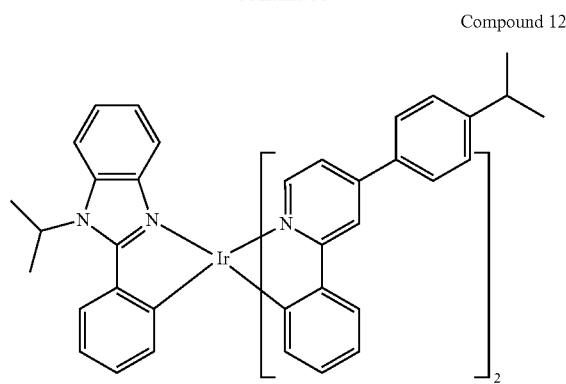
Compound 17
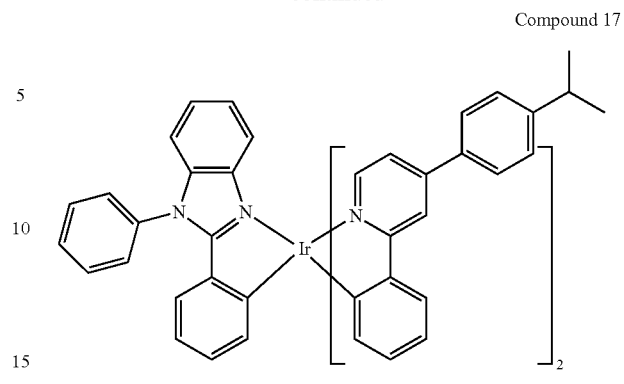
Compound 14
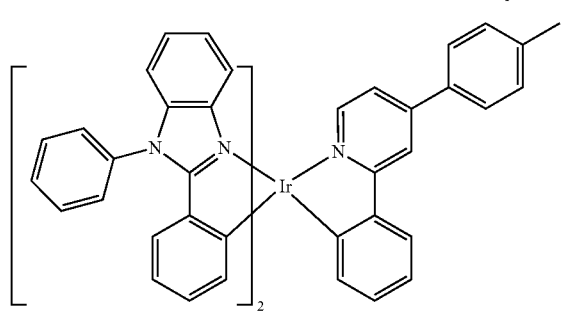
Compound 20
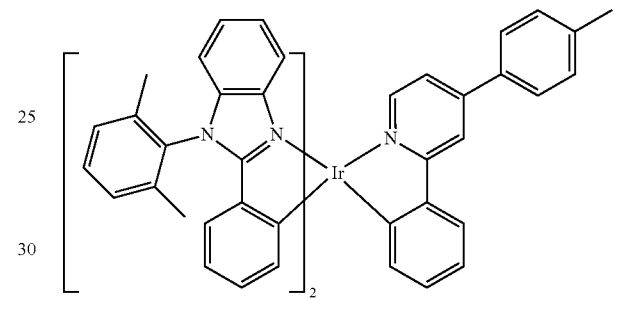
Compound 15
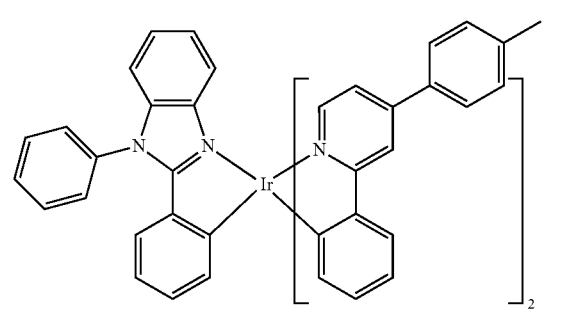
Compound 21
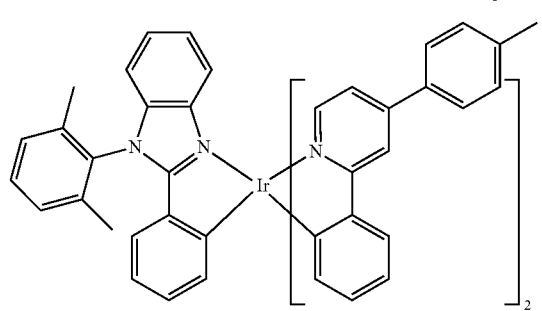
Compound 16
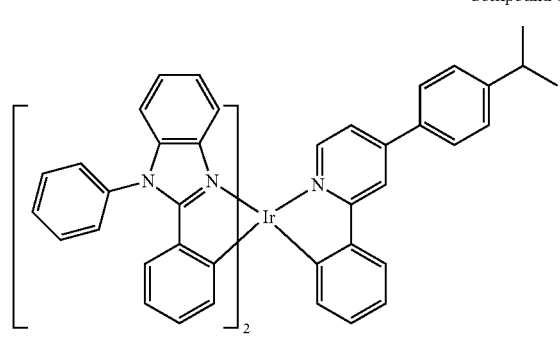
Compound 22
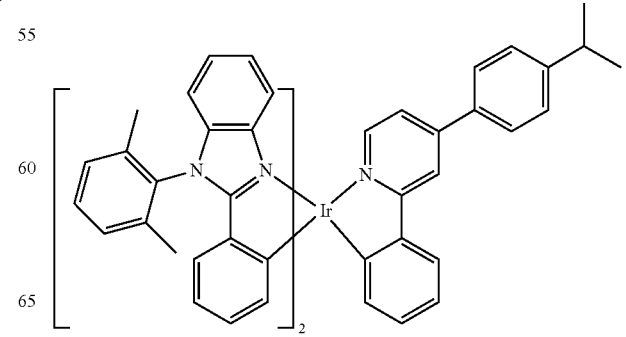

Compound 23
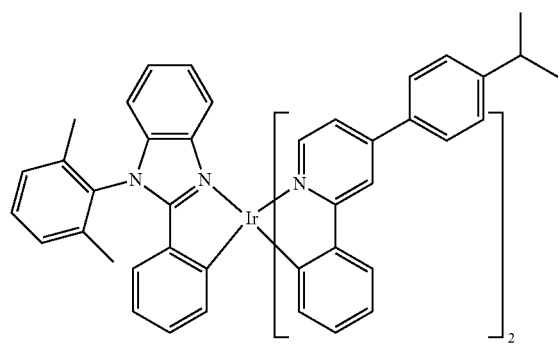
Compound 26
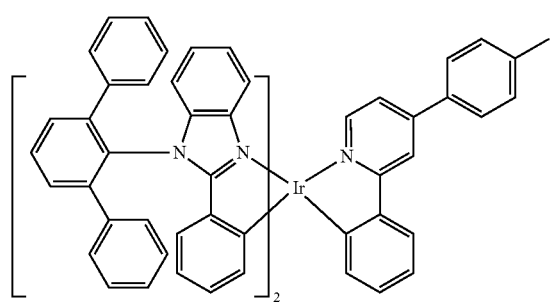
Compound 27
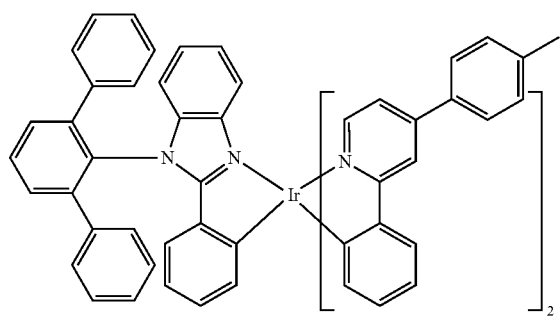
Compound 28
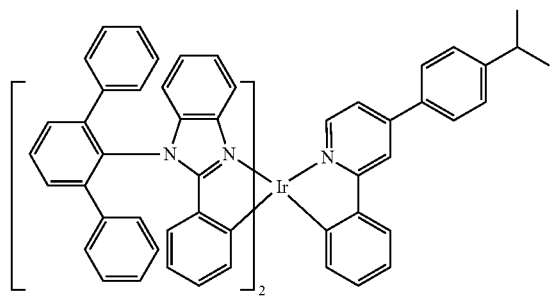
Compound 29
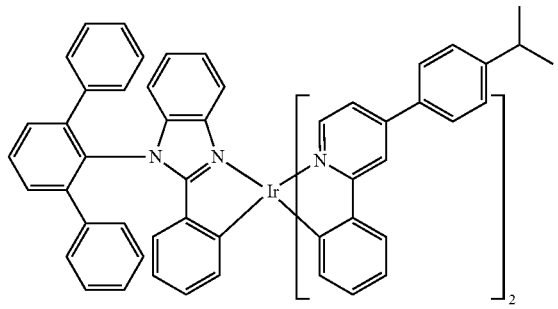
Compound 32
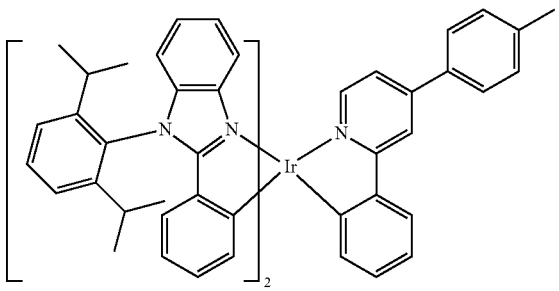
Compound 33
Compound 34
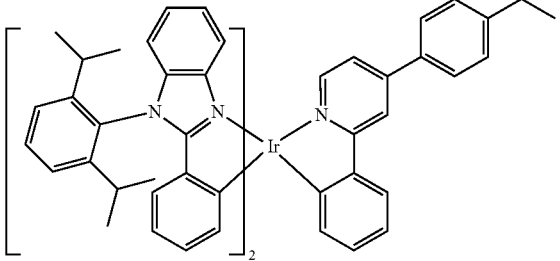
Compound 35

Compound 36
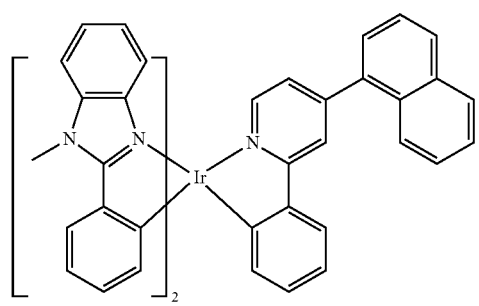
Compound 37
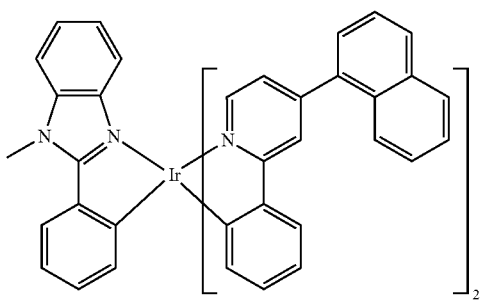
Compound 38
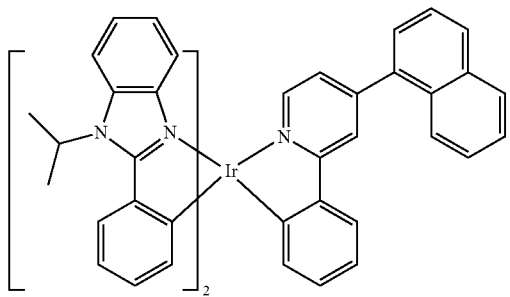
Compound 39
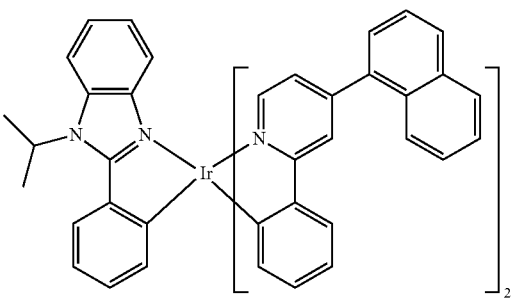
Compound 40
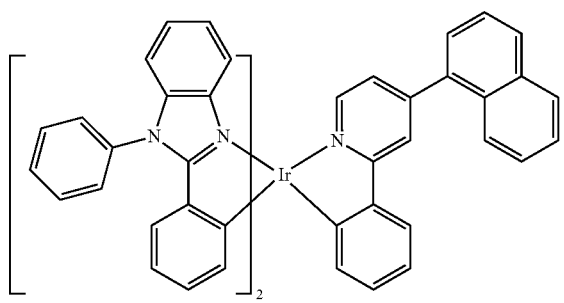
Compound 41
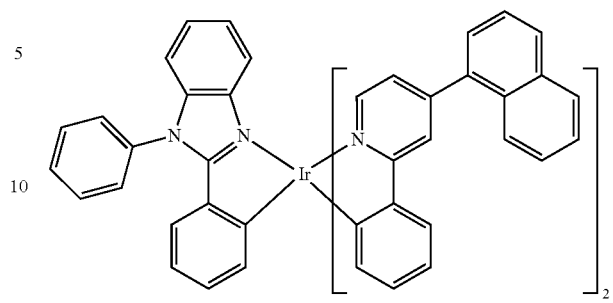
Compound 42
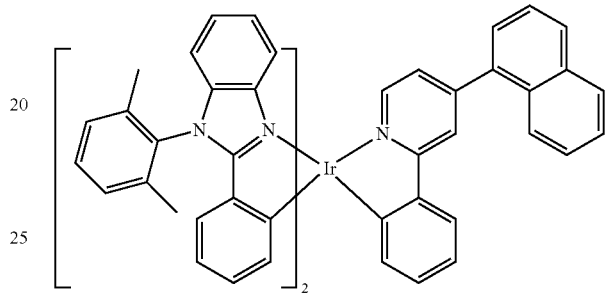
Compound 43
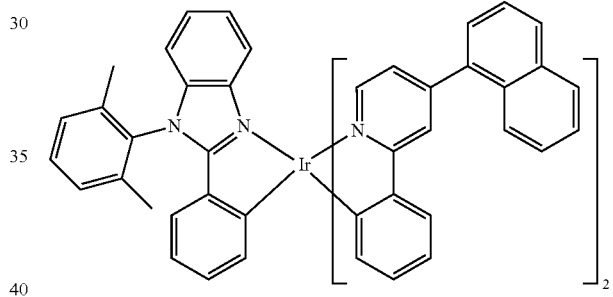
Compound 44
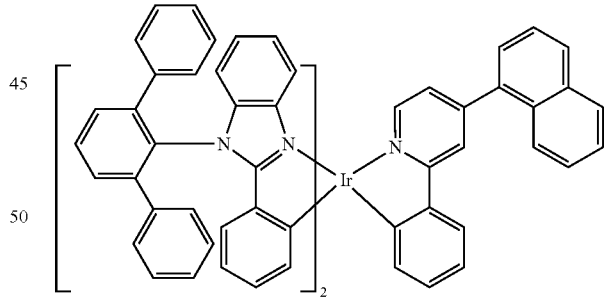
Compound 45
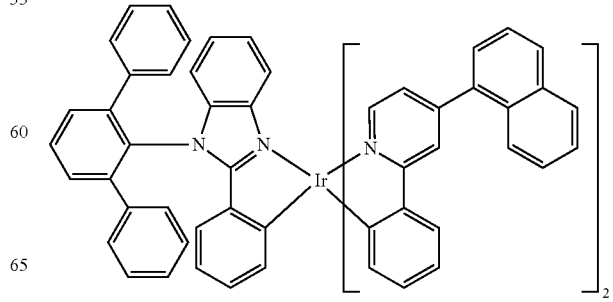

Compound 46
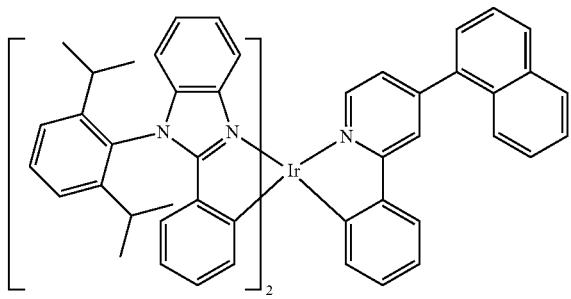
Compound 47
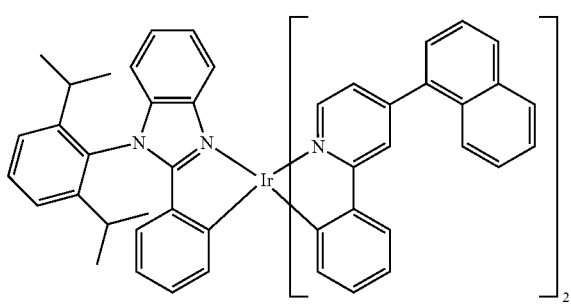
Compound 48
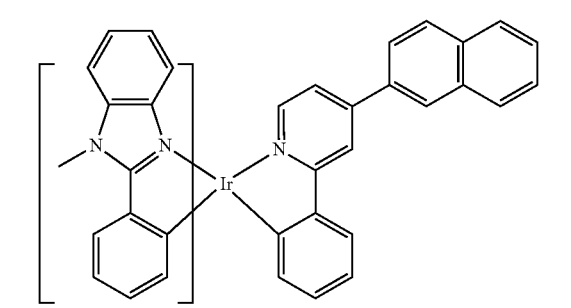
Compound 49
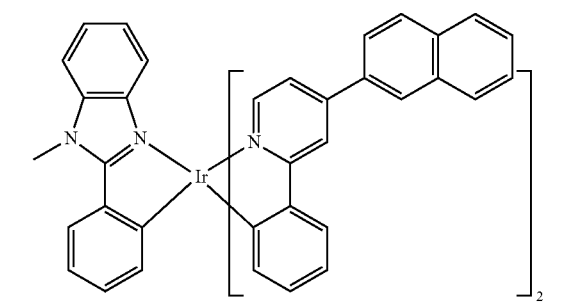
Compound 50
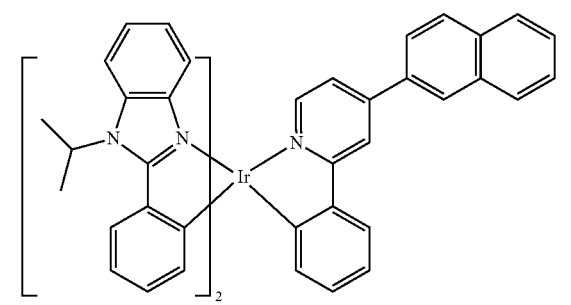
Compound 51
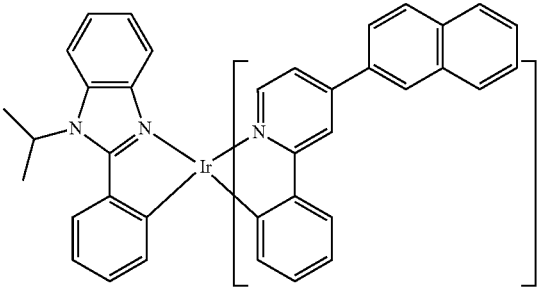
Compound 52
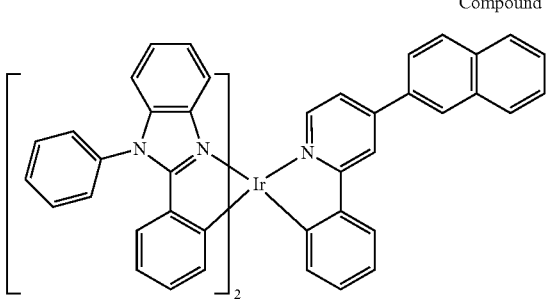
Compound 53
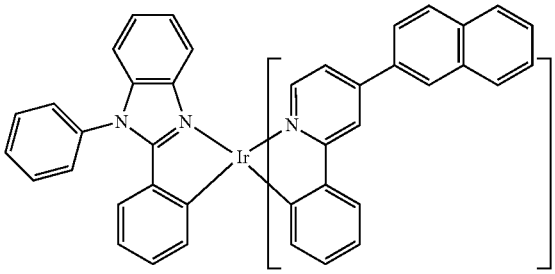
Compound 54
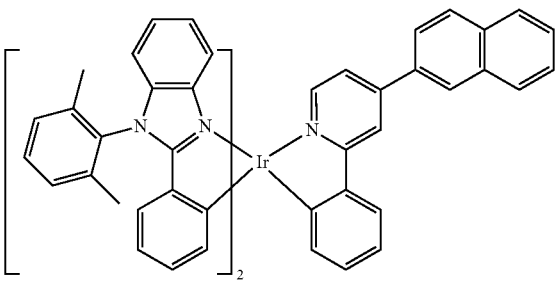
Compound 55
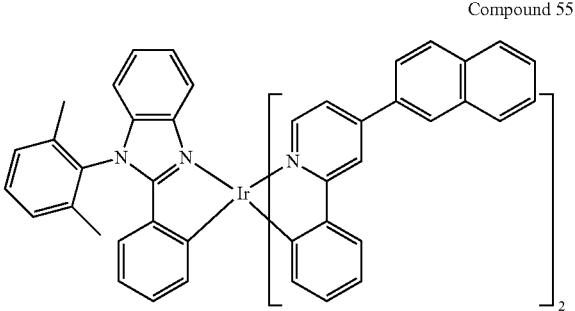

Compound 56
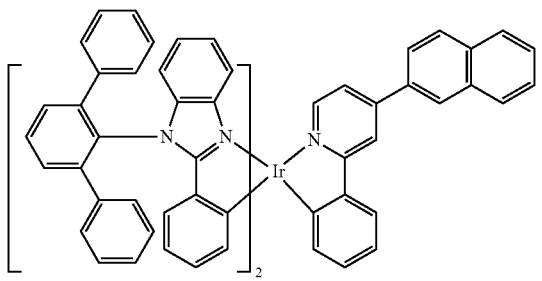
Compound 57
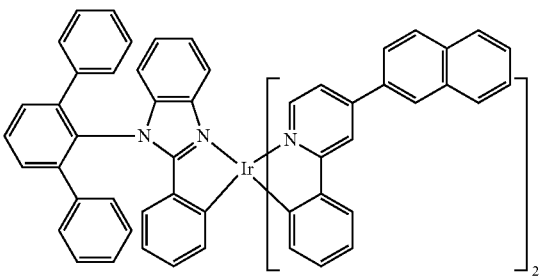
Compound 58
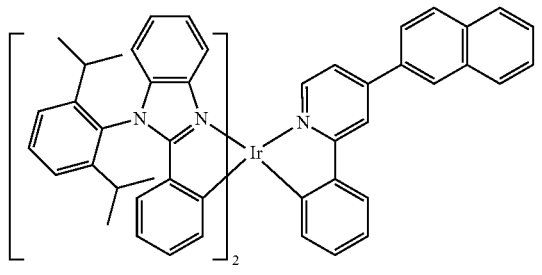
Compound 59
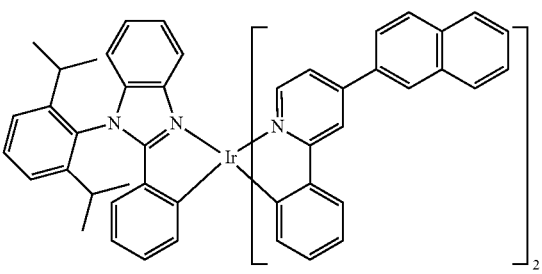
Compound 60
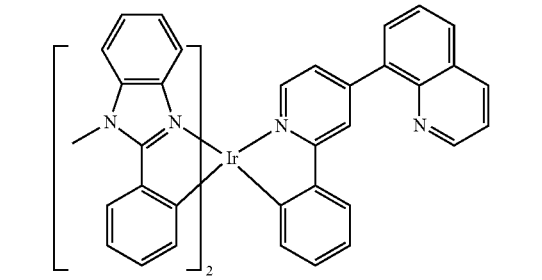
Compound 61
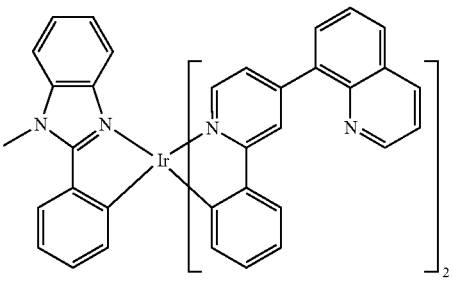
Compound 62
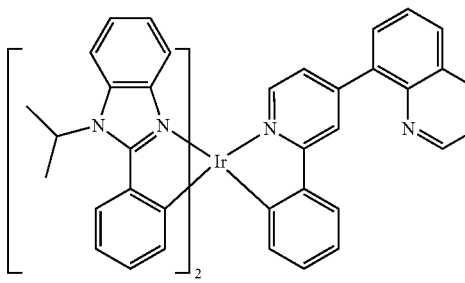
Compound 63
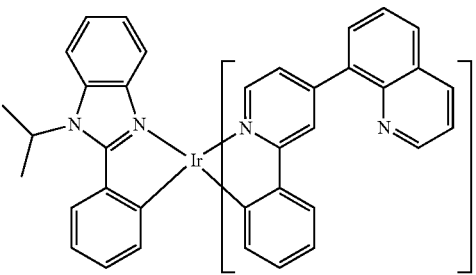
Compound 64
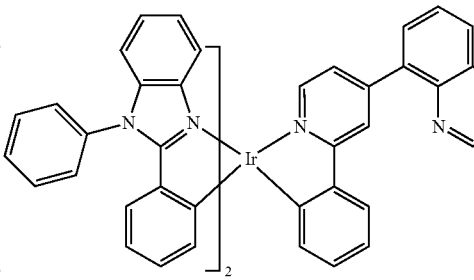
Compound 65
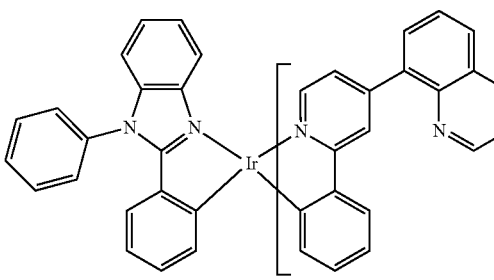

-continued
Compound 66
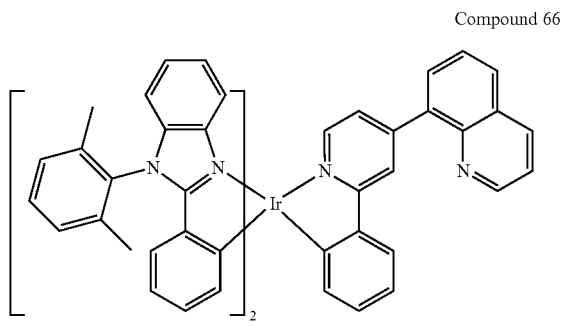
Compound 67
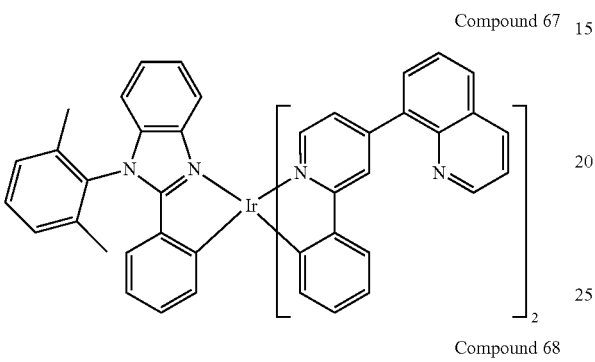
Compound 68
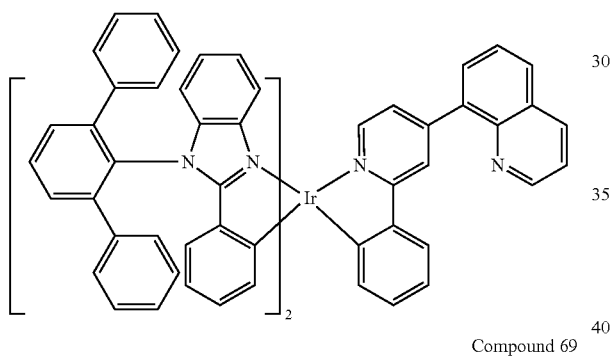
Compound 69
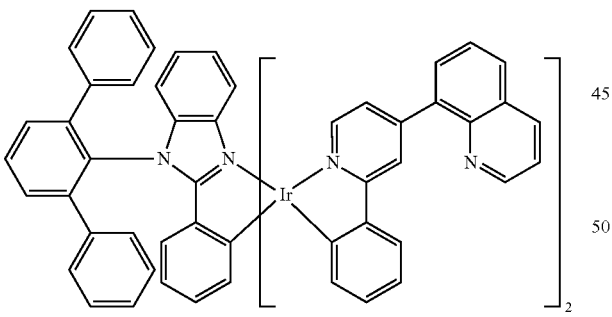
Compound 70
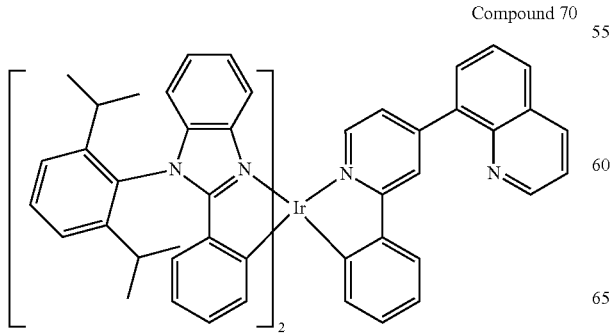
-continued
Compound 71
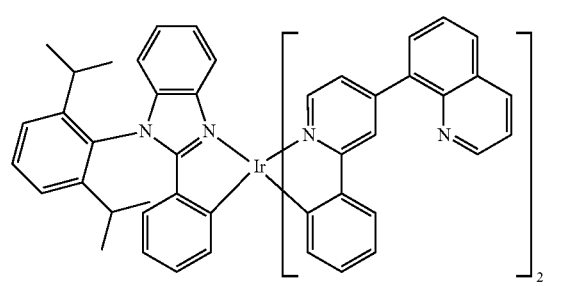
Compound 72
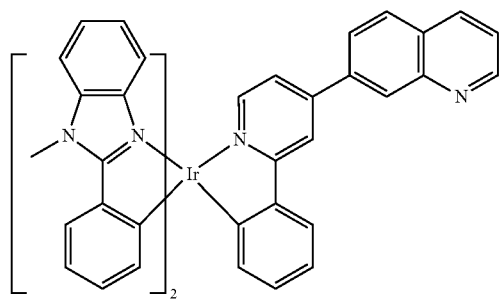
Compound 73
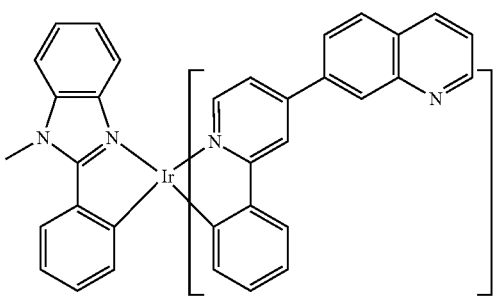
Compound 74
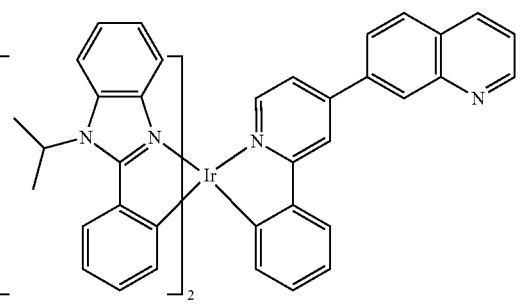
Compound 75
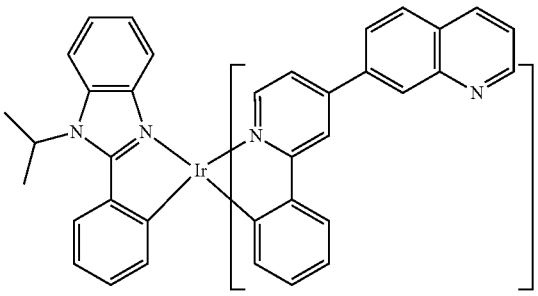

Compound 76
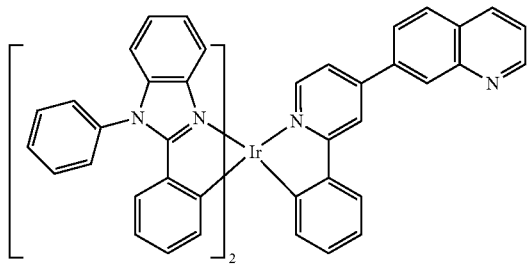
Compound 77
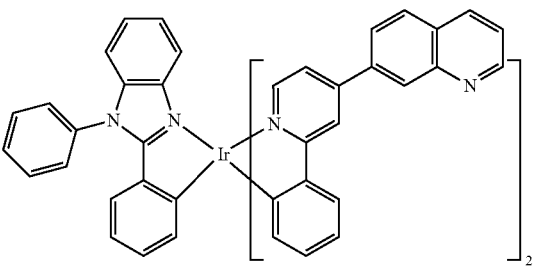
Compound 78
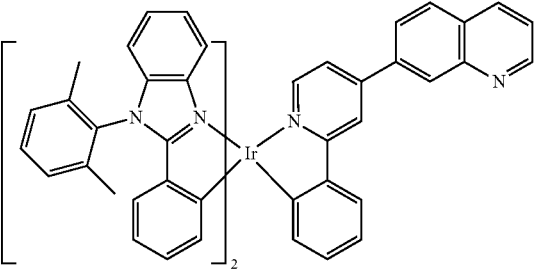
Compound 79
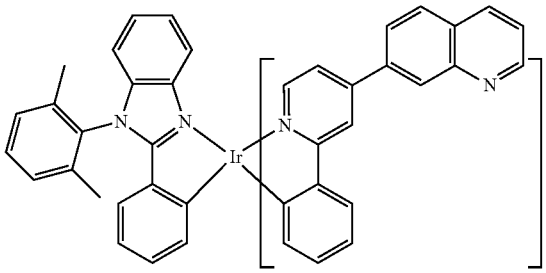
Compound 80
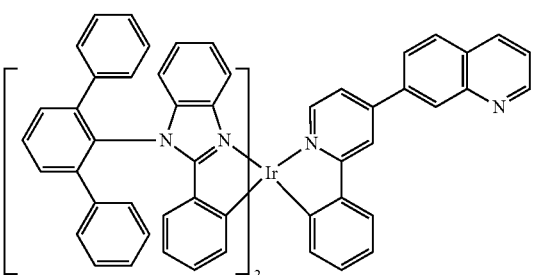
Compound 81
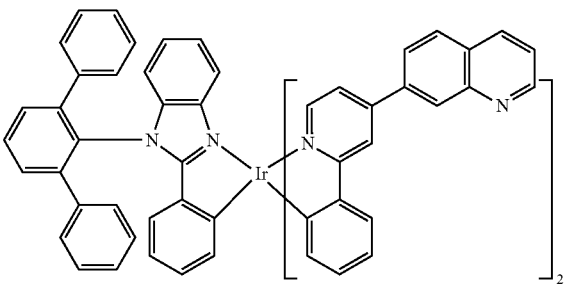
Compound 83
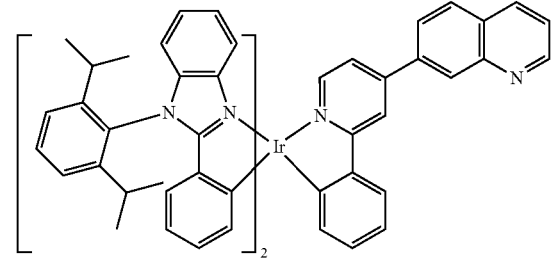
Compound 84
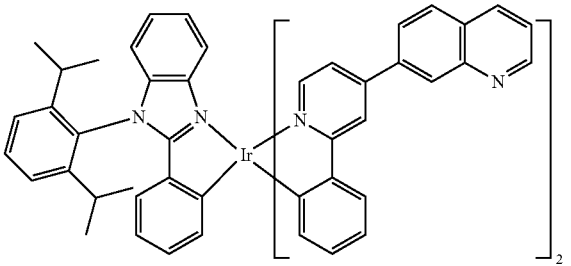
Compound 87
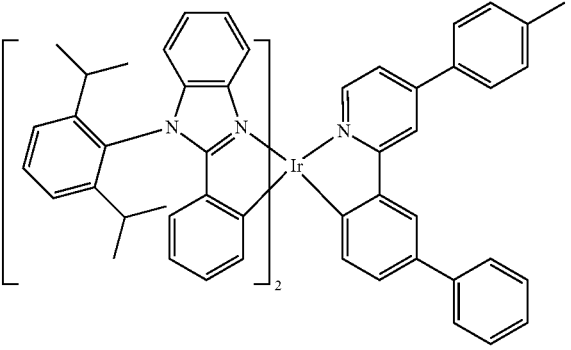
Compound 88
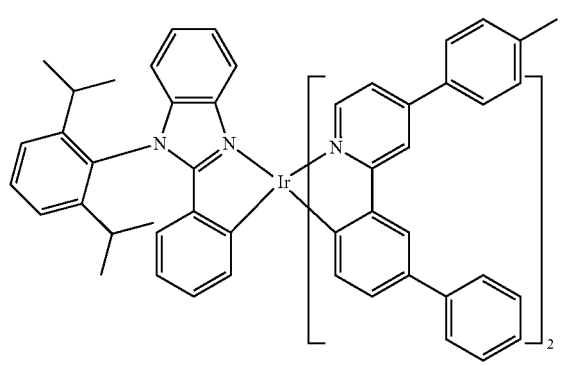

Compound 89
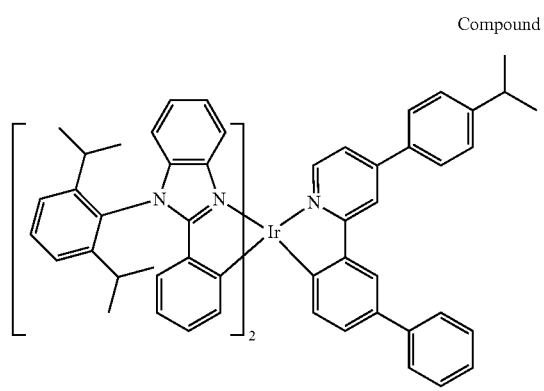
Compound 90
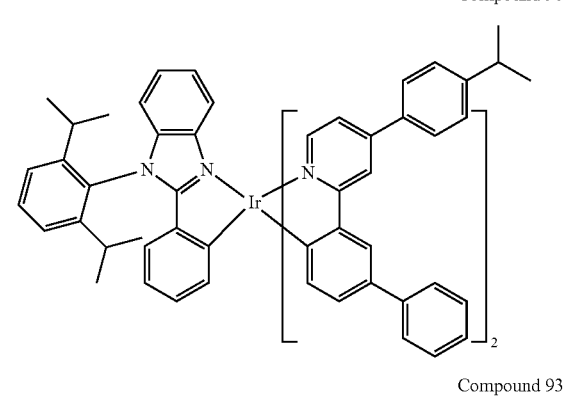
Compound 93
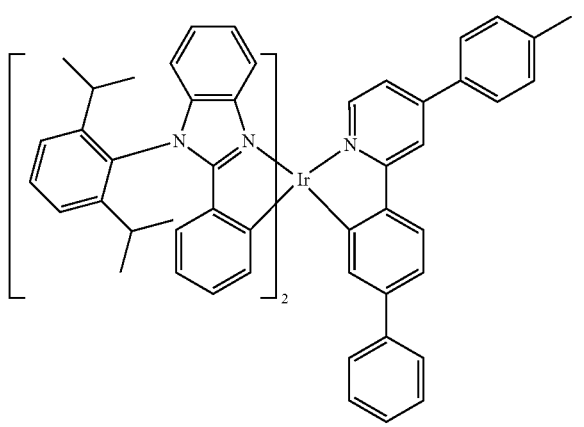
Compound 94
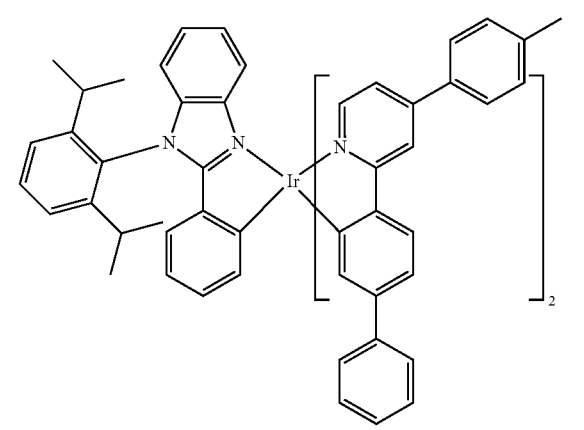
Compound 95
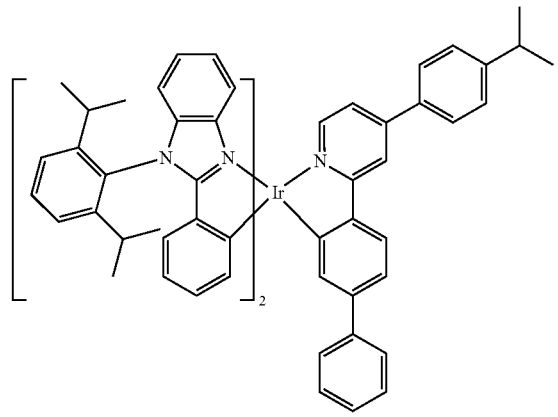
Compound 96
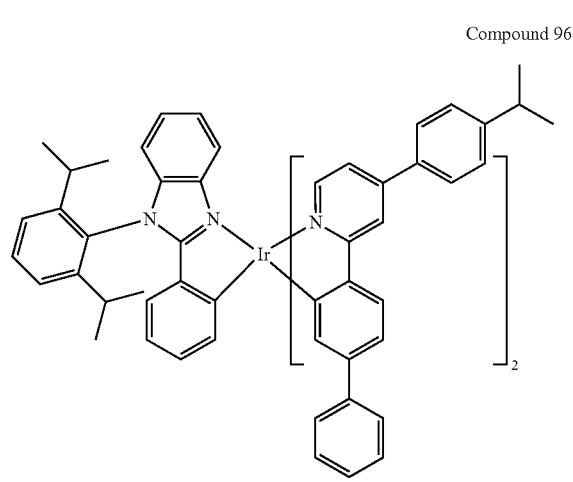
Compound 97
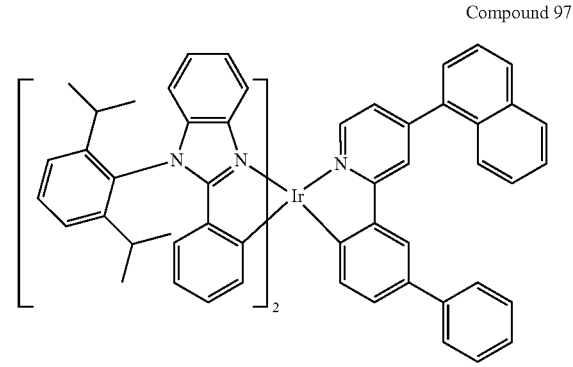
Compound 98
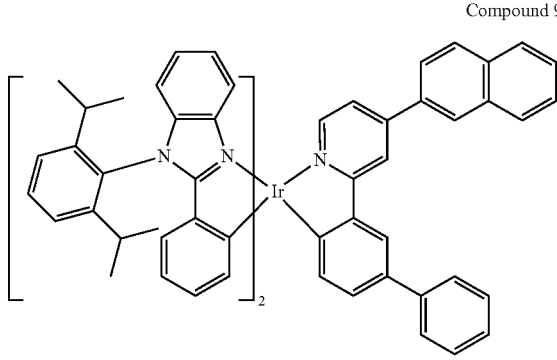

Compound 99

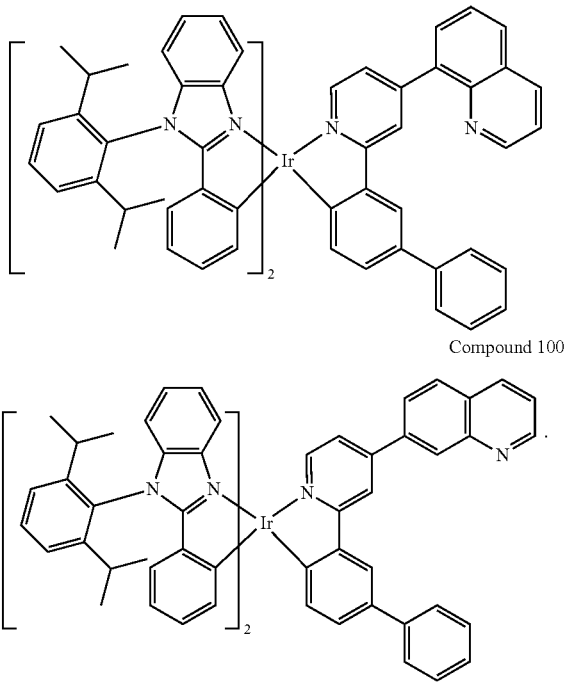

Compound 100

13. A first device comprising a first organic light emitting device, comprising:
an anode;
a cathode; and
an organic layer, disposed between the anode and the cathode, comprising a compound having the formula:

Formula I

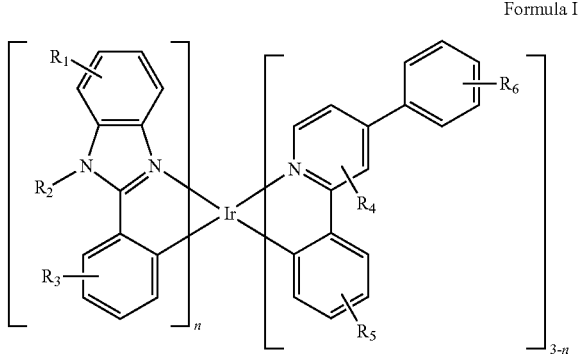

wherein $R_1$, $R_3$, $R_4$, $R_5$, and $R_6$ represent mono-, di-, tri- or tetra-substitution;
wherein $R_1$, $R_2$, $R_3$, $R_4$, $R_5$, and $R_6$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein $R_1$, $R_3$, $R_4$, $R_5$, and $R_6$ are optionally fused and may be further substituted;
wherein (1) $R_6$ is alkyl or heteroalkyl at a position para to a pyridine bonded to iridium, or (2) $R_6$ is fused and, optionally, further substituted, or (3) both conditions (1) and (2) are satisfied; and
wherein n=1 or 2.

14. The first device of claim 13, wherein the organic layer is an emissive layer and the compound is an emissive dopant.
15. The first device of claim 13, wherein the organic layer is an emissive layer and the compound is a non-emissive dopant.
16. The first device of claim 13, wherein the organic layer further comprises a host.
17. The first device of claim 16, wherein the host comprises a triphenylene containing benzo-fused thiophene or benzo-fused furan;
wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1-Ar_2$, $C_nH_{2n}-Ar_1$, or no substitution;
wherein n is from 1 to 10; and
wherein $Ar_1$ and $Ar_2$ are independently selected from the group consisting of benzene, biphenyl, naphthalene, triphenylene, carbazole, and heteroaromatic analogs thereof.
18. The first device of claim 17, wherein the host has the formula:

Compound B

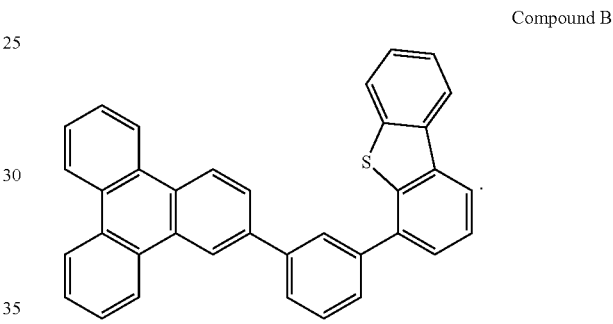

19. The first device of claim 16, wherein the host is a metal complex.
20. The first device of claim 13 wherein the first device is a consumer product.
21. The first device of claim 13, wherein the first device is an organic light-emitting device.
22. The first device of claim 13, wherein the first device further comprises a second emissive dopant having a peak wavelength of between 400 to 500 nanometers.
23. The first device of claim 22, wherein the second emissive dopant is a fluorescent emitter.
24. The first device of claim 22, wherein the second emissive dopant is a phosphorescent emitter.
25. The first device of claim 13, wherein the first device comprises a lighting panel.
26. The first device of claim 13, wherein the first device further comprises a first organic light-emitting device comprising a compound of Formula I and a second light emitting device separate from the first organic light-emitting device comprising an emissive dopant having a peak wavelength of between 400 to 500 nanometers.
27. The first device of claim 13, wherein the first device comprises an organic-light emitting device having a first emissive layer and a second emissive layer;
wherein the first emissive layer comprises a compound of Formula I; and
wherein the second emissive layer comprises an emissive dopant having a peak wavelength of between 400 to 500 nanometers.

* * * * *